US006300482B1

(12) United States Patent
Ciossek et al.

(10) Patent No.: US 6,300,482 B1
(45) Date of Patent: Oct. 9, 2001

(54) MDKI, A NOVEL RECEPTOR TYROSINE KINASE

(75) Inventors: Thomas Ciossek, Munich (DE); Axel Ullrich, Portola Valley; Birgit Millauer, Belmont, both of CA (US)

(73) Assignee: Max-Flanck-Gesellschaft Zuer Forderung Der, Munich (DE)

( * ) Notice: Subject to any disclaimer, the term of this patent is extended or adjusted under 35 U.S.C. 154(b) by 0 days.

(21) Appl. No.: 08/368,776

(22) Filed: Jan. 3, 1995

(51) Int. Cl.[7] ............................ C07H 21/02; C12N 15/00; C12N 1/20; C12P 21/06
(52) U.S. Cl. ................ 536/23.1; 536/24.31; 435/320.1; 435/252.3; 435/69.1
(58) Field of Search .............................. 536/23.1, 24.31, 536/23.01; 435/320.1, 252.3, 69.1

(56) References Cited

U.S. PATENT DOCUMENTS

| | | |
|---|---|---|
| 3,691,016 | 9/1972 | Patel et al. . |
| 3,969,287 | 7/1976 | Jaworek et al. . |
| 4,195,128 | 3/1980 | Hildebrand et al. . |
| 4,229,537 | 10/1980 | Hodgins et al. . |
| 4,247,642 | 1/1981 | Hirohara et al. . |
| 4,330,440 | 5/1982 | Ayers et al. . |
| 4,376,110 | 3/1983 | David et al. . |
| 4,945,050 | 7/1990 | Sanford et al. . |
| 4,946,778 | 8/1990 | Ladner et al. . |
| 5,504,000 * | 4/1996 | Hman et al. .......................... 435/194 |
| 5,521,295 * | 5/1996 | Pacifici et al. ...................... 536/23.4 |
| 5,981,246 * | 11/1999 | Fox et al. ............................. 435/194 |

FOREIGN PATENT DOCUMENTS

| | | |
|---|---|---|
| 93/00425 * | 1/1993 | (WO) . |
| 9323429 | 11/1993 | (WO) . |
| 9323569 | 11/1993 | (WO) . |
| WO 95/28484 * | 10/1995 | (WO) . |

OTHER PUBLICATIONS

Bowie et al (Science, 257:1306–1310), 1990.*
Bork (Genome Research, 10:398–400), 1990.*
Burgess et al (J. Cell Bio, 111:2129–2138, 1990).*
Lazar et al (Mol.Cell. Bio, 1988, 8: 1247–1252).*
Tao et al (J. Immunol, 1989, 143; 2595–2601).*
Aaronson, "Growth Factors and Cancer, " *Science* 254:1146–1153 (1991).
Abe et al., "Molecular Characterization of a Novel Metabotropic Glutamate Receptor mGluR5 Coupled to Inositol Phosphate/$Ca^{2+}$ Signal Transduction, " *J. Biol. Chem.* 267:13361–13368 (1992).
Adelman et al., "In Vitro Deletional Mutagenesis for Bacterial Production of the 20,000–Dalton Form of Human Pituitary Growth Hormone," *DNA* 2(3):183–193 (1983).
Basler and Hafen, "Ubiquitous Expression of sevenless: Position–Dependent Specification of Cell Fate, " *Science* 243:931–934 (1989).

Benoist and Chambon, "In vivo sequence requirements of the SV40 early promoter region, " *Nature* 290:304–310 (1981).
Bird et al., "Single–Chain Antigen–Binding Proteins," *Scinece* 242:423–426 (1988).
Bitter et al., "Expression and Secretion Vectors for Yeast," *Methods in Enzym.* 153:516–544 (1987).
Böhme et al., "PCR mediated detection of a new human receptor–tyrosine–kinase, HEK 2," *Oncogene* 8:2857–2862 (1993).
Brinster et al., "Factors Affecting the Efficiency of Introducing Foreign DNA into Mice by Microinjecting Eggs, " *Proc. Natl. Acad. Sci. USA* 82:4438–4442 (1985).
Capecchi, "Altering the Gonome by Homologous Recombination, "*Science* 244:1288–1292 (1989).
Chabot et al., "The proto–oncogene c–kit encoding a transmembrane tyrosine kinase receptor maps to the mouse W location, " *Nature* 335:88–89 (1988).
Chan and Watt, "*eek and erk*, new members of the *eph* subclass of receptor protein–tyrosine kinases, " *Oncogene* 6:1057–1061 (1991).
Chen and Okayama, "High–Efficiency Transformation of Mammalian Cells by Plasmid DNA, " *Mol. and Cell. Biol.* 7(8):2745–2752 (1987).
Chomczynski and Sacchi, "Single–Step Method of RNA Isolation by Acid Guanidinium Thiocyanate–Phenol–Chloroform Extraction, " *Analytical Biochemistry* 162:156–159 (1987).
Chowdhury et al., "Long–term Improvement of Hypercholesterolemia After *Ex Vivo* Gene Therapy in LDLR–Deficient Rabbits, " *Science* 254:1802–1805 (1991).
Ciossek et al., "Identification of alternatively spliced mRNAs encoding variants of DK1, a novel receptor tyrosine kinase expressed in the murine nervous system, " *Oncogene* 10(1):97–108 (1995).
Colbére–Garapin et al., "A New Dominant Hybrid Selective Marker for Higher Eukaryotic Cells, " *J. Mol. Biol.* 150:1–14 (1981).

(List continued on next page.)

*Primary Examiner*—Susan Ungar
(74) *Attorney, Agent, or Firm*—Foley & Lardner

(57) ABSTRACT

The present invention relates to MDK1 polypeptides, nucleic acids encoding such polypeptides, cells, tissues and animals containing such nucleic acids, antibodies to such polypeptides, assays utilizing such polypeptides, and methods relating to all of the foregoing.

Methods for treatment, diagnosis, and screening are provided for diseases or conditions characterized by an abnormality in a signal transduction disorder. The signal transduction pathway involves an interaction between a MDK1 receptor tyrosine kinase and a receptor for the kinase. The MDK1 receptor tyrosine kinase may be truncated and lack a kinase domain and may be selected from the group consisting of MDK1.T1, MDK1.T2, MDK1.Δ1 and MDK1.Δ2.

14 Claims, 6 Drawing Sheets

OTHER PUBLICATIONS

Cole et al., "The EBV–Hybridoma Technique and its Application to Human Lung Cancer, " pp. 77–96 in *Monoclonal Antibodies and Cancer Therapy* eds. Reisfeld and Sell, Alan R. Liss, Inc., New York, (1983).

Creighton, *Proteins: Structures and Molecular Principles* pp. 79–86, W. H. Freeman and Co., New York (1983).

Cristiano et al., "Hepatic Gene Therapy: Adenovirus Enhancement of Receptor–Mediated Gene Delivery and Expression in Primary Hepatocytes," *Proc. Natl. Acad. Sci. USA* 90:2122–2126 (1993).

Curiel et al., "Adenovirus Enhancement of Epithlial Cells via the Receptor–mediated Endocytosis Pathway," *Am. J. Respir. Cell. Mol. Biol.* 6:247–252 (1992).

Domchek et al., "Inhibition of SH2 Domain/Phosphoprotein Association by a Nonhydrolyzable Phosphonopeptide," *Biochemistry* 31:9865–9870 (1992).

Ellis et al., "Embryo Brain Kinase: a novel gene of the eph/elk receptor XP002002321 tyrosine kinase family," *EMBL Database entry MMBEK*, Accession No. X81466, Sep. 16, 1994).

Fantl et al., "Distinct Phosphotyrosines on a Growth Factor Receptor Bind to Specific Molecules That Mediate Different Signaling Pathways," *Cell* 69:413–423 (1992).

Feinberg and Vogelstein, "A Techique for Radiolabeling DNA Restriction Endonuclease Fragments to High Specific Activity, " *Analytical Biochemistry* 132:6–13 (1983).

Felder et al., "SH2 Domains Exhibit High–Affinity Binding to Tyrosine–Phosphorylated Peptides Yet Also Exhibit Rapid Dissociation and Exchange," *Mol. and Cell. Biol.* 13(3):1449–1455 (1993).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7417 (1987).

Fendly et al., "Characterization of Murine Monoclonal Antibodies Reactive to Either the Human or Epidermal Growth Receptor of HER2/*neu* Gene Product" *Cancer Research* 50:1550–1558 (1990).

Fingl and Woodbury, Chapter 1, pp. 1–46 in *The Pharmacological Basis of Therapeutics* (5th edition),eds. Goodman et al., MacMillian Publishing Co., Inc. New York (1975).

Fry et al., "New insights into protein–tyrosine kinase receptor signaling complexes," *Protein Science* 2:1785–1797 (1993).

Geissler et al., "The Dominant–White Spotting (W) Locus of the Mouse Encodes the c–*kit* Proto–Oncogene, " *Cell* 55:185–192 (1988).

Gilardi–Hebenstreit et al., "An Eph–related receptor protein tyrosine kinase gene segmentally expressed in the developing mouse hindbrain," *Oncogene* 7:2499–2506 (1992).

Hammer and Walling, "Regulation In Vivo of a Cloned Mammalian Gene: Cadmium Induces the Transcription of a Mouse Metallothionein Gene in SV40 Vectors," *J. of Molecular and Applied Genetics* 1:273–288 (1982).

Hammer et al., "Spontaneous Inflammatory Disease in Transgenic Rats Expressing HLA–B27 and Human $\beta_2$m: An Animal Model of HLA–B27–Associated Human Disorders," *Cell* 63:1099–1112 (1990).

Hanks et al., "The Protein Kinase Family: Conserved Features and Deduced Phylogeny of the Catalytic Domains," *Science* 241:42–52 (Jul. 1988).

Hardie, "Roles of Protein Kinases and Phosphatases in Signal Transduction," *Symp. Soc. Exp. Bio.* 44:241–255 (1990).

Hirai et al., "A Novel Putative Tyrosine Kinase Receptor Encoded by the *eph* Gene," *Science* 238:1717–1720 (1987).

Houdebine and Chourrout, "Transgenesis in Fish," *Experientia* 47:891–897 (1991).

Huston et al., "Protein engineering of antibody binding sites: Recovery of specific activity in an anti–digoxin single–chain Fv analogue produced in *Escherichia coli* " *Proc. Natl. Acad. Sci. USA* 85:5879–5883 (1988).

Inouye and Inouye, "Up–promoter mutations in he *Ipp* gene of *Escherichia coli*," *Nucleic Acids Research* 13(9):3100–3111 (1985).

Jansen et al., "Immunotoxins: Hybrid Molecules Combining High Specificity and Potent Cytotoxicity," *Immunological Rev.* 62:185–216 (1982).

Johnston and Hopper, "Isolation of the yeast regulatory gene *GAL*4 and analysis of its dosage effects on the galactose/melibiose regulon," *Proc. Natl. Acad. Sci. USA* 79:6971–6975 (1982).

Joyner et al., "Production of a mutation in mouse *En*–2 gene by homologous recombination in embryonic system cells," *Nature* 338:153–156 (1989).

Kaneda et al., "The Improved Efficient Method for Introducing Macromolecules into Cells Using HVJ (Sendai Virus) Liposomes with angliosides," *Experimental Cell Research* 173:56–69 (1987).

Kaneda et al., "Increased Expression of DNA Cointroduced with Nuclear Proteion in Adult Rat Liver," *Science* 243:375–378 (1989).

Killen and Lindstrom, "Specific Killing of Lymphocytes that Cause Experimental Autoimmune Myasthenia Gravis by Ricin Toxin–Acetylcholine Receptor Conjugates," *J.of Immunology* 133:2549–2553 (1984).

Köhler and Milstein, "Continuous cultures of fused cells secreting antibody of predefined specificity," *Nature* 256:495–496 (1975).

Kozak, "Complication and analysis of sequences upstream from the translational start site in eukaryotic mRNAs," *Nucleic Acids Research*12:857–873 (1984).

Lam et al., "A new type of synthetic peptide library for identifying ligand–binding activity," *Nature* 354:82–84 (1991).

Lammers, "Differential Activities of Proteins Tyrosine Phosphatases in Intact Cells," *J. Biol. Chem.* 268:22456–22462 (1993).

Letwin et al., "Novel protein–tyrosine kinase cDNAs related to *fps/fes* and *eph* cloned using anti–phosphotyrosine antibody," *Oncogene* 3:621–627 (1988).

Lindberg and Hunter, "cDNA Cloning and Characterization of *eck*,and Epithelial Cell Receptor Protein–Tyrosine Kinase in the *eph/elk* Family of Protein Kinases," *Mol. and Cell. Biol.* 10:6316–6324 (1990).

Logan and Shenk, "Adenovirous tripartite leader sequence enchances translation of mRNAs late after infection," *Proc. Natl. Acad. Sci. USA* 81:3655–3659 (1984).

Lowy et al., "Isolation of Transforming DNA: Cloning the Hamster aprt Gen," *Cell* 22:817–823 (1980).

Maher, "Tissue–dependent Regulation of Protein Tyrosine Kinase Activity during Embryonic Development," *J. Cell. Biol.* 112:955–963 (1991).

Maisonpierre et al., "Ehk–1 and Ehk–2: two novel members of the Eph receptor–like tyrosine kinase family with distinctive structures and neuronal expression," *Oncogenme* 8:3277–3288 (1993).

Marasco et al., "Design, intracelluar expression, and activity of a human anti–human immunodeficiency virus type 1 gp120 single–chain antibody," *Proc. Natl. Acad. Sci. USA* 90:7889–7893 (1993).

McKnight, "Functional Relationships between Transcriptional Control Signals of the Thymidine Kinase Gene of Herpes Simplex Virus," *Cell* 31:355–365 (1982).

Millauer, "High Affinity VEGF Binding and Developmental Expression Suggest Flk–1 as a Major Regulator of Vasculogenesis and Angiogenesis," *Cell* 72:835–846 (1993).

Morrison et al., "Chimeric human antibodymolecules: Mouse antigen–binding domains with human constant region domains," *Proc. Natl. Acad. Sci. USA* 81:6851–6855 (1984).

Mulligan and Berg, "Selection for animal cells that express the *Escherichia coli* gene coding for xanthine–guanine phosphoribosyltransferase," *Proc. Natl. Acad. Sci. USA* 78(4):2072–2076 (1981).

Mulligan, "The Basic Science of Gene Therapy," *Science* 260:926–932 (1993).

Nelson et al., "Detection of Acridinium Esters by Chemiluminescence," *Nonisotopic DNA Probe Techniques* ed. L. J. Kricka (San Diego:Academic Press, Inc. pp. 275–310 (1992).

Neuberger et al., "Recombinant antibodies possessing novel functions," *Nature* 312:604–608 (1984).

Nieto et al., "A receptor protein tyrosine kinase implicated in the segmental patterning of the hindbrain and mesoderm," *Development* 116:1137–1150 (1992).

Nocka et al., "Expression of *c–kit* gene products in known cellular targets of *W* mutations in normal and *W* mutant mice –evidence for an impaired *c–kit* kinase in mutant mice," *Genes Dev.* 3:816–826 (1989).

O'Hare et al., "Transformation of mouse fibroblasts to methotrexate by a recombinant plasmid expressing a prokaryotic dihydrofolate reductase," *Proc. Natl. Acad. Sci. USA* 78(3):1527–1531 (1981).

Pasquale, "Indentification of chicken embryo kinase 5, a developmentally regulated receptor–type tyrosine kinase of the Eph family," *J. Neuroscience* 2:523–534 (1991).

Pasquale et al., "Cek5, a Membrane Receptor–Type Tyrosine Kinase, Is in Neurons of the Embryonic and Postnatal Avian Brain," *J. Neuroscience* 12:3956–3967 (1992).

Pasquale and Singer, "Identification of a developmentally regulated protein–tyrosine kinase by using anti–phosphotyrosine antibodies to a screen a cDNA expression library," *Proc. Natl. Acad. Sci. USA* 88:5449–5453 (1989).

Posada and Cooper, "Molecular Signal Integration. Interplay Between Serine, threonine and Tyrosine Phosphorylation," *Mol. Biol. of the Cell* 3:583–592 (1992).

Pursel et al., "Genetic Engineering of Livestock," *Science* 244:1281–1288 (1989).

Raffioni et al., "The Receptors for the Nerve Growth Factor and Other Neurotrophins," *Annu. Rev. Biochem.* 62:823–850 (1993).

Redemann et al., "Anti–Oncogenic Activity of Signalling-–Defective Epidermal Growth Factor Receptor Mutants," *Mol. and Cell. Biol.* 12(2):491–498 (1992).

Rotin et al., "SH2 domains prevent tyrosin dephosphorylation of the EGF receptor: identification of Tyr992 as the high–affinity binding site for SH2 domains of phospholipase Cγ," *The EMBO J.* 11(2):559–567 (1992).

Rüther and Müller–Hill, "Easy Identification of cDNA clones," *EMBO J.* 2(10):1791–1794 (1983).

Sajjadi et al., "Identification of New *eph*–Related Receptor Tyrosine Kinase Gene From Mouse and Chicken That is Developmentally Regulated and Encodes at Least Two Forms of the Receptor," *The New Biologist* 3:769–778 (1993).

Sajjadi and Pasquale, "Five novel avian Eph–related tyrosine kinases are differently expressed, " *Oncogene* 8:1807–1813 (1993).

Sanger et al., "DNA sequencing with chain–terminating inhibitors, " *Proc. Natl. Acad. Sci. USA* 74:5463–5467 (1997).

Santerre et al., "Expression of prokaryotic genes for hygromycin B and G418 resistance as dominant–selection markers in mouse L cells," *Gene* 30:147–156 (1984).

Schlessinger, "Signal transduction by allosteric receptor oligomerization," *Trends Biochem. Sci.* 13:443–447 (1988).

Silver et al., "Amino terminus of the yeast *GAL4* gene product is sufficient for nuclear localiztion," *Proc. Natl. Acad. Sci. USA* 81:5951–5955 (1984).

Skolnik et al., "Cloning of P13 Kinase–Associated p85 Utilizing a Novel Method for Expression/Cloning of Target Proteins for Receptor Tyrosin Kinases," *Cell* 65:83–90 (1991).

Songyang et al., "SH2 Domains Recognize Specific Phosphopeptide Sequences, " *Cell* 72:767–778 (1993).

Sprenger et al., "The *Drosophila* gene *torso*encodes a putative receptor kinase," *Nature* 338:478–483 (1989).

Stephenson et al., "Platelet–derived growth factor receptor α–subunit gene (Pdgfra) is deleted in he mouse patch (Ph) mutation," *Proc. Natl. Acad. Sci. USA* 88:6–10 (1991).

Stryer, Lubert, *Biochemistry* (Third Edition) W. H. Freeman & Company, New York, pp. 7–8 (1988).

Szybalska and Szybalski, "Genetics of Human Cell Lines, IV. DNA–Mediated Heritable Transformation of a Biochemical Trait," *Proc. Natl. Acad. Sci. USA* 48:20262034 (1962).

Takeda et al., "Construction of chimaeric processed immunoglobulin genes containing mouse variable and human constant region sequences," *Nature* 314:452–45 (1985).

Ullrich and Schlessinger, "Signal Trandsuction by Receptors with Tyrosine Kinase Activity," *Cell* 61:203–212 (1990).

Van Heeke and Schuster, "Expression of Human Asparagine Synthetase in *Escherichia coli*, "*J. Biol. Chem.* 264(10):5503–5509 (1989).

Ward et al., "Binding activites of a repertoire of single immunoglobulin variable domains secreted from *Escherichia coli*," *Nature* 341:544–546 (1989).

Wicks et al., "Molecular cloning of *HEK*, the gene encoding a receptor tyrosine kinase expressed by human lymphoids tumor cell lines," *Proc. Natl. Acad. Sci. USA* 89:1611–1615 (1992).

Wigler et al., "Transformation of mammalian cells with amplifable dominant–acting gene," *Proc. Natl. Acad. Sci. USA* 77(6):3567–3570 (1980).

Wigler et al., "Transfer of Purified Herpes Virus Thymidine Kinase Gene to Cultured Mouse Cells," *Cell* 11:223–232 (1977).

Wilson et al., "Clinical Protocol: Ex Vivo Gene Therapy of Familial Hypercholesterolemia," *Human Gene Therapy* 3:179–222 (1991).

Wolff et al., "Direct Gene Transfer into Mouse Muscle In Vivo," *Science* 247:1465–1468 (1990).

Wu and Wu, "Receptor–mediated In Vitro Gene Transformation by a Soluble DNA Carrier System," *J. Biol. Chem.* 262:4429–4432 (1987).

Wu et al., "Characterization and Molecular Cloning of a Putative Binding Protein for Heparin–binding Growth Factors," *J. Biol. Chem.* 266:16778–16785 (1991).

Yang et al., "In Vivo and In Vitro Gene Transfer to Mammalian Somatic Cells by Particle Bombardment," *Proc. Natl. Acad. Sci. USA* 87:9568–9572 (1990).

Zhu et al., "Systemic Gene Expression After Intravenous DNA Delivery into Adult Mice," *Science* 261:209–211 (1993).

\* cited by examiner

FIG. 1A aagcggccggtctgcagtcggagacttgcaggcagcaaacacggtgcgaacgaaccggagggggagagagaaatcaaacagctaagcgt  90
ggagcagacggcctgggacccagaaggggatcgatgcgaggagcgcaataataacaacaataataacccacttcggagcaaacagcatat  180
aaagagctgcgacccaactgcagcctaaaaaaatcaaacctgctcatgcacc  232

```
              10                            20                            30
M  V  V  Q  T  R  F  P  S  W  I  I  L  C  Y  I  W  L  L  G  F  A  H  T  G  E  A  Q  A  A
ATGGTTGTTCAAACTCGGTTCCCTTCGTGGATTATTTTGTGTTACATCTGGCTGCTTGGCTTTGCACACACGGGGGAGGCGCAGGCTGCG  322
              40                            50                            60
K  E  V  L  L  L  D  S  K  A  Q  Q  T  E  L  E  W  I  S  S  P  P  S  G  W  E  E  I  S  G
AAGGAAGTACTATTACTGGACTCGAAAGCACAACAAACAGAATTGGAATGGATTTCCTCTCCACCCAGTGGGTGGGAAGAAATTAGTGGT  412
              70                            80                            90
L  D  E  N  Y  T  P  I  R  T  Y  Q  V  C  Q  V  M  E  P  N  Q  N  N  W  L  R  T  N  W
TTGGATGAGAACTACACTCCGATAAGAACATACCAGGTGTGCCAGGTCATGGAGCCCAACCAGAACAACTGGCTGCGGACTAACTGGATT  502
              100                           110                           120
S  K  G  N  A  Q  R  I  F  V  E  L  K  F  T  L  R  D  C  N  S  L  P  G  V  L  G  T  C  K
TCTAAAGGCAACGCACAAAGGATTTTTTGTAGAATTGAAATTCACCTTGAGGGATTGTAATAGTCTTCCCGGAGTCCTGGGAACTTGCAAG  592
              130                           140                           150
E  T  F  N  L  Y  Y  Y  E  T  D  Y  D  T  G  R  N  I  R  E  N  L  Y  V  K  I  D  T  I  A
GAAACGTTTAATTTGTACTATTATGAAACAGACTACGACACCGGCAGGAATATACGAGAAAACCTTTATGTTAAAATAGACACCATTGCT  682
              160                           170                           180
A  D  E  S  F  T  Q  G  D  L  G  E  R  K  M  K  L  N  T  E  V  R  E  I  G  P  L  S  K  E
GCAGATGAAAGTTTCACACAAGGTGACCTTGGTGAAAGAAAGATGAAGCTGAACACTGAGGTGAGAGAGATTGGACCTTTGTCCAAAAAG  772
              190                           200                           210
G  F  Y  L  A  F  Q  D  V  G  A  C  I  A  L  V  S  V  K  V  Y  Y  K  K  C  W  T  I  V  E
GGATTCTATCTTGCCTTTCAGGATGTAGGGGCTTGCATAGCATTGGTTTCTGTCAAAGTGTACTACAAGAAGTGCTGGACCATTGTTGAG  862
              220                           230                           240
N  L  A  V  F  P  D  T  V  T  G  S  E  F  S  S  L  V  E  V  R  G  T  C  V  S  S  A  E  E
AACTTAGCTGTCTTTCCAGATACAGTGACTGGTTCGGAATTTTCCTCCTTAGTCGAGGTCCGTGGGACATGTGTCAGCAGTGCCGAGGAA  952
              250                           260                           270
E  A  E  N  S  P  R  M  H  C  S  A  E  G  E  W  L  V  P  I  G  K  C  I  C  K  A  G  Y  Q
GAGGCAGAAAATTCCCCCAGAATGCATTGCAGTGCAGAAGGAGAGTGGCTAGTACCCATTGGAAAATGCATCTGCAAAGCAGGCTATCAG  1042
              280                           290                           300
Q  K  G  D  T  C  E  P  C  G  R  R  F  Y  K  S  S  S  Q  D  L  Q  C  S  R  C  P  T  H  S
CAAAAAGGGGACACTTGCGAACCCTGTGGCCGCAGGTTCTACAAATCTTCCTCTCAGGATCTCCAGTGTTCTCGTTGTCCAACCCACAGC  1132
              310                           320                           330
F  S  D  R  E  G  S  S  R  C  E  C  E  D  G  Y  Y  R  A  P  S  D  P  P  Y  V  A  C  T  R
TTCTCTGACCGAGAAGGATCATCCAGGTGTGAATGTGAAGATGGGTACTACAGAGCTCCTTCTGATCCACCATACGTTGCATGCACGAGG  1222
              340                           350                           360
P  P  S  A  P  Q  N  L  I  F  N  I  N  Q  T  T  V  S  L  E  W  S  P  P  A  D  N  G  G  R
CCTCCCTCTGCACCACAGAACCTTATTTTCAATATCAATCAAACGACTGTAAGTTTGGAATGGAGTCCTCCGGCTGACAACGGGGGAAGA  1312
              370                           380                           390
N  D  V  T  Y  R  I  L  C  K  R  C  S  W  E  Q  G  E  C  V  P  C  G  S  N  I  G  Y  M  P
AACGATGTCACCTACAGAATACTGTGTAAGCGGTGCAGTTGGGAACAGGGAGAATGTGCCATGCGGAAGTAACATTGGATACATGCCC  1402
              400                           410                           420
Q  Q  T  G  L  E  D  N  Y  V  T  V  M  D  L  L  A  E  A  N  Y  T  F  E  V  E  A  V  N  G
CAGCAGACGGGATTAGAGGATAACTATGTCACTGTCATGGACCTACTTGCCCATGCAAATTACACTTTCGAAGTTGAAGCTGTAAATGGA  1492
              430                           440                           450
V  S  D  L  S  R  S  Q  R  L  F  A  A  V  S  I  T  T  G  Q  A  A  P  S  Q  V  S  G  V  M
GTTTCGGACTTAAGCAGATCCCAGAGGCTCTTCGCTGCTGTTAGCATCACCACCGGTCAAGCAGCTCCCTCGCAAGTGAGTGGAGTCATG  1582
              460                           470                           480
K  E  R  V  L  Q  R  S  V  Q  L  S  W  Q  E  P  E  E  P  N  G  V  I  T  E  Y  E  I  K  Y
AAGGAGCGAGTACTGCAGCGGAGTGTGCAGCTTTCCTGGCAGGAGCCGGAGCATCCCAATGGAGTCATCACGGAATATGAAATCAAGTAT  1672
              490                           500                           510
Y  E  K  D  Q  R  E  R  T  Y  S  T  L  K  T  K  S  T  S  A  S  I  N  N  L  K  P  G  T  V
TATGAGAAAGATCAACGGGAAAGGACGTACTCAACACTCAAAACCAAGTCCACCTCCGCCTCCATTAATAATCTGAAACCGGGAACAGTG  1762
              520                           530                           540
Y  V  F  Q  I  R  A  V  T  A  A  G  T  G  N  Y  S  P  R  L  D  V  A  T  L  E  E  A  S  G
TACGTCTTTCAGATCCGGGCGGTCACTGCTGCCGGTTATGGAAACTACAGCCCTAGGCTTGATGTTGCCACACTTGAGGAAGCTTCAGGT  1852
```

FIG. 1B

```
                  550                      560                       570
     K M F E A T A V S S E Q N P V I I I A V V A V A G T I I L V
     AAAATGTTTGAAGCGACAGCAGTCTCCAGTGAACAGAATCCTGTCATCATAATTGCTGTAGTGGCTGTAGCAGGGACCATCATCTTGGTG 1942
                  580                      590                       600
     F M V F G F I I G R R H C G Y S K A D Q E G D E E L Y F H F
     TTCATGGTGTTCGGCTTCATCATTGGAAGAAGGCACTGTGGTTATAGCAAGGCTGACCAAGAAGGGGATGAAGAACTCTACTTTCATTTT 2032
                  610                      620                       630
     K F P G T K T Y I D P E T Y E D P N R A V H Q F A K E L D A
     AAATTTCCAGGCACCAAAACCTACATTGACCCTGAAACCTATGAGGACCCAAATAGAGCTGTCCATCAATTCGCCAAGGAGCTAGATGCC 2122
                  640                      650                       660
     S C I K I E R V I G A G E F G E V C S G R L K L P G Q R D V
     TCCTGTATTAAAATTGAGCGTGTGATTGGTGCAGGAGAATTTGGAGAAGTTTGCAGTGGTCGTTTGAAACTTCCGGGCCAGAGAGATGTT 2212
                  670                      680                       690
     A V A I K T L K V G Y T E K Q R R D F L C E A S I M G Q F D
     GCAGTGGCCATAAAAACCCTGAAAGTTGGTTACACAGAAAAGCAAAGGAGGGACTTTTTATGCGAAGCAAGCATCATGGGGCAATTTGAC 2302
                  700                      710                       720
     H P N V V H L E G V V T R G K P V M I V I E F M E N G A L D
     CACCCAAATGTCGTCCATTTGGAAGGGGTTGTTACAAGAGGGAAGCCTGTCATGATTGTGATAGAGTTCATGGAGAATGGAGCCCTGGAT 2392
                  730                      740                       750
     A F L R K H D G Q F T V I Q L V G M L R G I A A G M R Y L A
     GCATTTCTCAGGAAACACGATGGGCAGTTTACAGTCATTCAGTTGGTAGGAATGTTGAGAGGTATTGCCGCTGCCATGCGATACTTGGCT 2482
                  760                      770                       780
     D M G Y V H R D L A A R N I L V N S N L V C K V S D F G L S
     GATATGGGATACGTTCACAGGGACCTTGCAGCGCGCAACATCCTTGTCAACAGCAATCTTGTTTGTAAAGTGTCAGATTTTGGCCTTTCC 2572
                  790                      800                       810
     R V I E D D P E A V Y T T T G G K I P V R W T A P E A I Q Y
     CGGGTTATAGAGGATGATCCCGAAGCTGTCTACACCACGACTGGTGGAAAAATTCCAGTAAGGTGGACTGCACCGGAAGCCATTCAATAC 2662
                  820                      830                       840
     R K F T S A S D V W S Y G I V M W E V M S Y G E R P Y W D M
     CGGAAGTTCACCTCAGCCAGCGATGTGTGGAGCTATGGGATTGTCATGTGGGAAGTGATGTCTTATGGAGAAAGACCTTACTGGGACATG 2752
                  850                      860                       870
     S N Q D V I K A I E E G Y R L P A P M D C P A G L H Q L M L
     TCAAATCAAGATGTCATTAAAGCGATAGAAGAAGGTTATCGTTTGCCGGCGCCCATGGATTGCCCAGCTGGTCTTCACCAGCTAATGCTG 2842
                  880                      890                       900
     D C W Q K D R A E R P K P E Q I V G I L D K M I R N R S S L
     GATTGTTGGCAGAAAGATCGGGCGGAAAGGCCAAAGTTTGAGCAGATAGTCGGAATTCTAGACAAAATGATTCGAAACCCAAGTAGTCTG 2932
                  910                      920                       930
     K T P L G T C S R P L S P L L D Q S T P D F T A F C S V G E
     AAAACACCCCTGGGAACTTGTAGTAGACCCTTAAGCCCTCTTCTGGACCAGAGCACTCCTGACTTCACTGCCTTCTGTTCAGTTGGAGAA 3022
                  940                      950                       960
     W L Q A I K M E R Y K D N F T A A G Y N S L E S V A R M T I
     TGGTTGCAAGCTATTAAAATGGAAAGGTATAAGGACAACTTCACAGCAGCGGGTTACAACTCACTCGAGTCAGTGGCCAGGATGACTATC 3112
                  970                      980                       990
     D D V M S L G I T L V G E Q K K I M S S I Q T M R A Q M L H
     GATGATGTGATGAGTTTAGGGATCACACTGGTTGGCCATCAAAAGAAGATCATGAGCAGCATCCAGACTATGCGGGCACAAATGTTGCAT 3202
     L H G T G I Q V *
     TTACACGGAACAGGCATCCAAGTGTGA                                                                 3229
     cacatcggcctccctcagatgaggcttaagactgcaggagaacagttctggccttcagtatacgcatagaatgctgctagaagacagttg 3319
     atatactgggtccttcctacaagaaagagaagattttagaagcacctccagacttgaactcctaagtgccaccagaatatacaaaaaggg 3409
     aatttaggatccaccactggtggccaggaacacagcagagacaataaacaaagtactacctgaaaaacatcccaacaccttgagctctcg 3499
     aacctccttttttatcttatagacttttaaaaatgtacataaagaatttaagaaagaatatatttgtcaaataaaaatcatgatcttatt 3589
     gttaaaatcaatgaaatattttccttaaaaaaaaaaaa                                                       3628 gttaaaatcaatgaaatattttccttaaaatatgtgatttcagactattcttttccagaaccatctgtgtttattctgcttaaggactt   3679
     gttttagaaagttatttgtagcttttggacctttttagtgttaaatttatgacacgttactacactgggaacctttgaagactctcaaact 3769
     taaaggaaagcaaaactacgcacatagtcgaggatggactttgtccttcatggctttggtatcctggctgtgtcattttgttaaaccagt  3859
     gatgttttcatattgtttgctgattggcaggtagttcaaaattgcaagttgccaagagctctgatatttttaacaggattttttttttct  3949
     ttgtaaaaatcagataacatactaactttcaatgaaaaaaaaaaaaaagaagcaataatgatccataaatactataaggcactttaa     4039
     cagattgtttatagagtgatttactaggcagaatttaataaaaaaaaaagagagatgtcaaattttaggtttatgtgtatatgataaaag  4129
     gctgagcttcgtctgaagatgctggtgaaagcaagactggaagcgaagctctccagctttggctaacccaatccgagcacatcaagagct  4219
     tcagtcttgtgacagtaagaaatttaggaacatagttgacctatattttgtattctttcttgttgaatgcagtccaaatacaaaa       4304
```

FIG. 2A

MDK1'-T1

```
                    570                    580                    590
V  A  V  A  G  T  I  I  L  V  F  M  V  F  G  F  I  I  G  R  R  H  C  G  Y  S  K  A  D  Q
GTGGCTGTAGCAGGGACCATCATCTTGGTGTTGTTCATGGTGTTCGGCTTCATCATTGGAAGAAGGCACTGTGGTTATAGCAAGGCTGACCAA   2002

600                             610
E  G  D  E  E  L  Y  F  H  S  L  V  T  N  E  H  L  S  V  L  *
GAAGGGGATGAAGAAGAACTCTACTTTCATTCTTTAGTAACAAATGAGCACCTGTCAGTTTTATAAccgcaacaataactgttaagacaat       2092
caattttggataaaacaatcaactacagcagaataaatcaagattttaagtcccattttcctttatacacattctgctattttgttgttat        2182
atgtttattttttaaactctgatcttgaatgtgatgatcttgattgaatgtgcagtgttaggctgcagtgtaaatatataaagacattgttctga    2272
gagcagtacgatttcatggaaagattgttgtggctgttgtcttgtcttgaaccaaatgaataagattgattgtgaattgaaatcttgaatattt    2362
attaatataaccaaatatgcctacctatctttgtcttgaaccaaatgaatacttttattgaatactttattgtgaatttgataaag             2452
ttgactgagcatttatgtgttacctgttgttctgggtgcattgaaatatttaacttttaaatgatactatgttgtttcaattttga             2542
ctaccttttgtgaggcatactggtcatacttggtcacgatccagatttagctaagcctttatatgaaaagtttatataaaccattctc          2632
tttcaaatcactgtcatactgtcatacttggtcacgatcccaggaatatttgaattttctaatttactctgcactttgtatatccagcctctc       2722
ccctcaaggtgaatataaaactatgtctttttgaatatttcttttgatgatagcagtccctcatctcttgtactaattttatgta              2812
tatgtcaacagtggttggtctttaaaaataagtaaaaaataaaaaataaaaaaaaaaaaa                                      2901
```

FIG. 2B

MDK1-T2

```
          570              580              590
V A V A G T I I L V F M V F G G F I I G R R H C G Y S K A D Q
GTGGCTGTGTAGCAGGGACCATCATCTTGGTGTTCATGGTGTTCGGCTTCATCATTGGAAGAAGGCACTGTGGTTATAGCAAGGCTGACCAA  2002
                 600              610              620
E G D E E L Y F H S L Y R E R G D G M E K T Q H N K K W M I
GAAGGGGATGAAGAACTCTACTTTCATTCTCTTTACAGGGAAAAGGGGAGACGGGATGGAAAAGACACAGCACAATAAGAAGTGGATGATT  2092

A S C S R L *
GCATCGTGCTCTCGTTTGTAGgtctcttttcctaatcaacactatgattttgaagtacgcgtacacgaagcaaacgggaagagataagga  2182
attagcattgtgaacctgactgtgtaatcctctcttccggaaagagatgagatgctattgcgatgagaatgtacaacttgcacctttgaaatc  2272
ttttttgataattagtgtctcagggagggggggggaagtagagaaagcaaa                                         2323
```

MDKI, A NOVEL RECEPTOR TYROSINE KINASE

FIELD OF THE INVENTION

The present invention relates generally to the field of cellular signal transduction and more specifically to the diagnosis and treatment of various diseases and conditions associated with abnormal cellular signal transduction pathways.

BACKGROUND OF THE INVENTION

The present invention concerns methods for diagnosis and treatment of disorders characterized by abnormal cellular signal transduction. The following is a discussion of relevant art, none of which is admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of tyrosine residues on proteins. The phosphorylation state of a protein is modified through the reciprocal actions of tyrosine kinases (TKs) and tyrosine phosphatases (TPs).

Receptor tyrosine kinases (RTKs) belong to a family of transmembrane proteins and have been implicated in cellular signaling pathways. The predominant biological activity of some RTKs is the stimulation of cell growth and proliferation, while other RTKs are involved in arresting growth and promoting differentiation. In some instances, a single tyrosine kinase can inhibit, or stimulate, cell proliferation depending on the cellular environment in which it is expressed.

RTKs are composed of at least three domains: an extracellular ligand binding domain, a transmembrane domain and a cytoplasmic catalytic domain that can phosphorylate tyrosine residues. Ligand binding to membrane-bound receptors induces the formation of receptor dimers and allosteric changes that activate the intracellular kinase domains and result in the self-phosphorylation (autophosphorylation and/or transphosphorylation) of the receptor on tyrosine residues. Their intrinsic tyrosine kinase is activated upon ligand binding, thereby initiating a complex signal transduction pathway that begins with receptor autophosphorylation and culminates in the tyrosine phosphorylation of a variety of cellular substrates and ultimately in the initiation of nuclear events necessary for the overall cell response. Individual phosphotyrosine residues of the cytoplasmic domains of receptors may serve as specific binding sites that interact with a host of cytoplasmic signaling molecules, thereby activating various signal transduction pathways.

The intracellular, cytoplasmic, non-receptor protein tyrosine kinases do not contain a hydrophobic transmembrane domain or an extracellular domain and share non-catalytic domains in addition to sharing their catalytic kinase domains. Such non-catalytic domains include the SH2 domains (SRC homology domain 2) and SH3 domains (SRC homology domain 3). The non-catalytic domains are thought to be important in the regulation of protein-protein interactions during signal transduction.

A central feature of signal transduction (for reviews, see Posada and Cooper, *Mol. Biol. Cell* 3:583–392, 1992; Hardie, *Symp. Soc. Exp. Biol.* 44:241–255, 1990), is the reversible phosphorylation of certain proteins. Receptor phosphorylation stimulates a physical association of the activated receptor with target molecules. Some of the target molecules such as phospholipase $C_\gamma$ are in turn phosphorylated and activated. Such phosphorylation transmits a signal to the cytoplasm. Other target molecules are not phosphorylated, but assist in signal transmission by acting as adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras.

The secondary signal transducer molecules generated by activated receptors result in a signal cascade that regulates cell functions such as cell division or differentiation. Reviews describing intracellular signal transduction include Aaronson, *Science*, 254:1146–1153, 1991; Schlessinger, *Trends Biochem. Sci.*, 13:443–447, 1988; and Ullrich and Schlessinger, *Cell*, 61:203–212, 1990.

RTKs are important regulators of developmental processes, as reflected by the high level of tyrosine phosphorylation in the early mouse embryo, which decreases with progressing development and is low in adult animal tissues (Pasquale and Singer, *Proc. Natl. Acad. Sci. USA* 88:5449–5453, 1989). For example, the mouse c-kit proto-oncogene plays a key role in the migrational behavior of specific cell types in mouse development (Chabot et al., *Nature* 335:88–89, 1988; Geissler et al., *Cell* 55:185–192, 1988; Nocka et al., *Genes Dev.* 3:816–826, 1989).

Disruption of the platelet-derived growth factor receptor α (PDGF-Rα) gene is responsible for the mouse patch mutation, which is characterized by prominent anatomical abnormalities in homozygotes (Stephenson et al., *Proc. Natl. Acad. Sci. USA* 88:6–10, 1991). Moreover, Flk-1, the cognate receptor for the vascular endothelial growth factor (VEGF), was shown to be a major regulator of vasculogenesis and angiogenesis (Millauer et al., *Cell* 72:835–846, 1993). Finally, in Drosophila, the RTK sevenless has a well established function in the control of photoreceptor cell fate (Basler and Hafen, *Science* 243:931–934, 1989), as does the RTK torso in the formation of terminal structures of Drosophila larva (Sprenger et al., *Nature* 338:478–483, 1989).

Among adult tissues, the brain contains the highest level of protein kinase activity, comparable to that found in embryonic tissues (Maher, P. A., *J. Cell. Biol.* 112:955–963, 1991). Members of the trk family of RTKs have well documented roles in promoting the differentiation and survival of diverse groups of neurons of the central and peripheral nervous systems (reviewed in Raffioni et al., *Annu. Rev. Biochem.* 62:823–850, 1993). The eck/eph RTK subfamily (Hirai et al., *Science* 238:1717–1720, 1987) currently comprises the largest subgroup of RTKs (Sajjadi and Pasquale, *Oncogene* 8:1807–1813, 1993), with most members being expressed in the developing or adult brain.

While RTKs such as eck (Lindberg and Hunter, *Mol. Cell. Biol.* 10:6316–6324, 1990), Hek2 (Böhme et al., *Oncogene* 8:2857–2862, 1993), Cek6, Cek9, and Cek10 (Sajjadi and Pasquale, *Oncogene* 8:1807–1813, 1993) have been reported to be widely expressed in a variety of tissues, Elk and Cek5 transcripts have been found predominantly in the brain (Letwin et al., *Oncogene* 3:621–627, 1988; Pasquale et al., *J. Neuroscience* 12:3956–3967, 1992).

As first noted by Maisonpierre et al. (Maisonpierre et al., *Oncogene* 8:3277–3288, 1993), there is a subclass of RTKs within the eck/eph family which, while being strongly expressed in the brain, are also found in other tissues, especially during embryogenesis. This subfamily includes Ehk-1, Ehk-2, (Maisonpierre et al., *Oncogene* 8:3277–3288, 1993), Mek4, Cek4, Hek (Sajjadi et al., *New Biol.* 3:769–778, 1991; Wicks et al., *Proc. Natl. Acad. Sci. USA* 89:1611–1615, 1992), eek (Chan and Watt, *Oncogene* 6:1057–1061, 1991), Sek (Nieto et al., *Development* 116:1137–1150, 1992; Gilardi-Hebenstreit et al., *Oncogene* 7:2499–2506, 1992), Cek7 and Cek8 (Sajjadi and Pasquale, *Oncogene* 8:1807–1813, 1993), whose members are more related to each other than to either of the above-mentioned kinases.

SUMMARY OF THE INVENTION

The present invention relates to MDK1 polypeptides, nucleic acids encoding such polypeptides, cells, tissues and animals containing such nucleic acids, antibodies to such polypeptides, assays utilizing such polypeptides, and methods relating to all of the foregoing. In particular, this invention relates to methods for diagnosis and treatment of a disorder, most preferably a disorder characterized by an abnormality in a signal transduction pathway, wherein the signal transduction pathway involves the interaction between a MDK1 receptor tyrosine kinase and a MDK1 binding partner.

The present invention is based upon the isolation and characterization of a new member of the subgroup of the eck/eph family of RTKs referred to above, which we have designated mouse developmental kinase 1 (MDK1). MDK1, which was found using a polymerase chain reaction (PCR) based approach, exhibits complex transcriptional regulation and is expressed in at least five different forms. Along with two variants containing amino acid deletions in the membrane-proximal extracellular domain and the juxtamembrane region, we also identified two truncated versions of MDK1 which lack the catalytic kinase domain. Although MDK1 is transcribed in a variety of tissues in early stages of development, it is found exclusively in the brain, spleen, and testes of adult mice. The neuronal expression sites characterized indicate an important role for MDK1 in the development of the nervous system.

In addition, we have determined that disruption or promotion of the interaction between a MDK1 receptor tyrosine kinase and MDK1 binding partner is useful in therapeutic procedures. Thus, we have determined that a kinase, termed MDK1, is involved in a protein-protein interaction of therapeutic importance. This interaction is associated with the basic signalling function of proteins associated with various diseases or conditions. MDK1 polypeptides are involved in various signal transduction pathways and thus the present invention provides several agents and methods useful for diagnosing, treating, and preventing various diseases or conditions associated with abnormalities in these pathways.

Thus, in a first aspect the invention features an isolated, enriched, or purified nucleic acid encoding a MDK1 polypeptide.

By "isolated" in reference to nucleic acid is meant a polymer of 2 (preferably 21, more preferably 39, most preferably 75) or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it and thus is meant to distinguish from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occuring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "a MDK1 polypeptide" is meant 30 or more contiguous amino acids set forth in the full length amino acid sequence of SEQ ID NO:2, or a functional derivative thereof as described herein. The MDK1 polypeptide can be encoded by a full-length nucleic acid sequence or any portion of the full-length nucleic acid sequence, so long as a functional activity of the polypeptide is retained. Examples of partial amino acid sequences are shown in SEQ ID NOS 3 and 5.

In preferred embodiments the isolated nucleic acid comprises, consists essentially of, or consists of a nucleic acid sequence set forth in the full length nucleic acid sequence SEQ ID NO:1, a functional derivative thereof, or at least 27, 30, 35, 40 or 50 contiguous nucleotides thereof; the MDK1 polypeptide comprises, consists essentially of, or consists of at least 9, 10, 15, 20, or 30 contiguous amino acids of a MDK1 polypeptide. The nucleic acid may be isolated from a natural source by cDNA cloning or subtractive hybridization; the natural source may be blood, semen, and tissue of various organisims including eukaryotes, mammals, birds, fish, plants, gorillas, rhesus monkeys, chimpanzees and humans; and the nucleic acid may be synthesized by the triester method or by using an automated DNA synthesizer. In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions. Examples of partial nucleic acid sequences are shown in SEQ ID NOS 4 and 6.

By "conserved nucleic acid regions", are meant regions present on two or more nucleic acids encoding a MDK1 polypeptide, to which a particular nucleic acid sequence can hybridize to under lower stringency conditions. Examples of lower stringency conditions suitable for screening for nucleic acid encoding MDK1 polypeptides are provided in Abe, et al. *J. Biol. Chem.,* 19:13361 (1992) (hereby incorporated by reference herein in its entirety, including any drawings). Preferably, conserved regions differ by no more than 7 out of 20 nucleotides.

By "unique nucleic acid region" is meant a sequence present in a full length nucleic acid coding for a MDK1 polypeptide that is not present in a sequence coding for any other naturally occurring polypeptide. Such regions preferably comprise 12 or 20 contiguous nucleotides present in the full length nucleic acid encoding a MDK1 polypeptide.

The invention also features a nucleic acid probe for the detection of a MDK1 polypeptide or nucleic acid encoding a MDK1 polypeptide in a sample. The nucleic acid probe contains nucleic acid that will hybridize to a sequence set forth in SEQ ID NO:1 or a functional derivative thereof.

In preferred embodiments the nucleic acid probe hybridizes to nucleic acid encoding at least 12, 27, 30, 35, 40 or 50 contiguous amino acids of the full-length sequence set forth in SEQ ID NO:2 or a functional derivitive thereof. Various low or high stringency hybridization conditions may be used depending upon the specificity and selectivity desired. Under stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount MDK1 RNA in a sample by contacting the sample with a nucleic acid probe under conditions such that hybridization occurs and detecting the presence or amount of the probe bound to MDK1 RNA. The nucleic acid duplex formed between the probe and a nucleic acid sequence coding for a MDK1 polypeptide may be used in the identification of the sequence of the nucleic acid detected (for example see, Nelson et al., in *Nonisotopic DNA Probe Techniques,* p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention also features recombinant nucleic acid, preferably in a cell or an organism. The recombinant nucleic acid may contain a sequence set forth in SEQ ID NO:1 or a functional derivative thereof and a vector or a promoter effective to initiate transcription in a host cell. The recombinant nucleic acid can alternatively contain a transcriptional initiation region functional in a cell, a sequence complimentary to an RNA sequence encoding a MDK1 polypeptide and a transcriptional termination region functional in a cell.

In another aspect the invention features an isolated, enriched, or purified MDK1 polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which man has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments the MDK1 polypeptide contains at least 9, 10, 15, 20, or 30 contiguous amino acids of the full-length sequence set forth in SEQ ID NO:2, or a functional derivitive thereof.

In yet another aspect the invention features an antibody (e.g., a monoclonal or polyclonal antibody) having specific binding affinity to a MDK1 polypeptide. The antibody contains a sequence of amino acids that is able to specifically bind to a MDK1 polypeptide. By "specific binding affinity"

is meant that the antibody binds to MDK1 polypeptides with greater affinity than it binds to other polypeptides under specified conditions.

Antibodies having specific binding affinity to a MDK1 polypeptide may be used in methods for detecting the presence and/or amount of a MDK1 polypeptide is a sample by contacting the sample with the antibody under conditions such that an immunocomplex forms and detecting the presence and/or amount of the antibody conjugated to the MDK1 polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a MDK1 polypeptide. By "hybridoma" is meant an immortalized cell line which is capable of secreting an antibody, for example a MDK1 antibody. In preferred embodiments the MDK1 antibody comprises a sequence of amino acids that is able to specifically bind a MDK1 polypeptide.

Another aspect of the invention features a method of detecting the presence or amount of a compound capable of binding to a MDK1 polypeptide. The method involves incubating the compound with a MDK1 polypeptide and detecting the presence or amount of the compound bound to the MDK1 polypeptide.

Thus, in another aspect, the invention features a method for treatment of an organism having a disease or condition characterized by an abnormality in a signal transduction pathway, wherein the signal transduction pathway involves the interaction between a MDK1 receptor tyrosine kinase and a MDK1 binding partner. The disorder may also be characterized by an abnormal level of interaction between MDK1 receptor tyrosine kinase and a MDK1 binding partner. The method includes disrupting or promoting that interaction (or signal) in vivo. The method also involves inhibiting or promoting the activity of the complex formed between MDK1 receptor tyrosine kinase and a MDK1 binding partner.

By "organism" is meant any living creature. The term includes mammals, and specifically humans. Preferred organisms include mice, as the ability to treat or diagnose mice is often predictive of the ability to function in other organisms such as humans.

By "disease or condition" is meant a state in an organism, e.g., a human, which is recognized as abnormal by members of the medical community. The disease or condition may be characterized by an abnormality in one or more signal transduction pathways in a cell, preferably a neuronal, fibroblast, epithelial, blood or cancer cell, wherein one of the components of the signal transduction pathway is a MDK1 receptor tyrosine kinase.

Examples of diseases or conditions to be treated or diagnosed by the present invention include neurodegenerative disorders, neuroproliferative disorders, cancers, hyperproliferative disorders such as psoriasis and neurofibromatosis, inflammatory disorders, Alzheimer's disease, Parkinson's disease, Lou Gehrig's disease (ALS), trauma, damaged or severed nerve injuries, Huntington's chorea, multiple sclerosis, muscular dystrophy, syringomiplia, Tabes Dorsalis, and cardiovascular accidents. These and other diseases or conditions are often characterized by one or more of the following symptoms: tumors, astasia, aphasia, paralysis, paresea, and paralagies.

By "abnormality" is meant a level which is statistically different from the level observed in organisms not suffering from such a disease or condition and may be characterized as either an excess amount, intensity or duration of signal or a deficient amount, intensity or duration of signal. The abnormality in signal transduction may be realized as an abnormality in neuronal or cancer cell function, viability or differentiation state. We have determined that such abnormal interaction in a pathway can be alleviated by action at the MDK1-binding partner interaction site in the pathway.

An abnormal interaction level may also either be greater or less than the normal level and may impair the normal performance or function of the organism. Thus, it is also possible to screen for agents that will be useful for treating a disease or condition, characterized by an abnormality in the signal transduction pathway, by testing compounds for their ability to affect the interaction between a MDK1 receptor tyrosine kinase and a MDK1 binding partner, since the complex formed by such interaction is part of the signal transduction pathway. However, the disease or condition may be characterized by an abnormality in the signal transduction pathway even if the level of interaction between MDK1 receptor tyrosine kinase and a MDK1 binding partner is normal.

By "interact" is meant any physical association between proteins, whether covalent or non-covalent. Examples of non-covalent bonds include electrostatic bonds, hydrogen bonds, and Van der Waals bonds. Stryer, i Biochemistry, 1988, pages 7–8. Furthermore, the interactions between proteins may either be direct or indirect. Another example of an indirect interaction is the independent production, stimulation, or inhibition of both MDK1 receptor tyrosine kinase and a MDK1 binding partner by a regulatory agent. Depending upon the type of interaction present, various methods may be used to measure the level of interaction. For example, the strengths of covalent bonds are often measured in terms of the energy required to break a certain number of bonds (i.e., kcal/mol) Non-covalent interactions are often described as above, and also in terms of the distance between the interacting molecules. Indirect interactions may be described in a number of ways, including the number of intermediary agents involved, or the degree of control exercised over the MDK1 receptor tyrosine kinase relative to the control exercised over the MDK1 binding partner.

By "MDK1 receptor tyrosine kinase" is meant an amino acid sequence substantially similar to the sequence shown in FIG. 1, or fragments thereof and is specifically meant to include human equivalents of MDK1. A sequence that is substantially similar will have at least 70% identity (preferably at least 80% and most preferably 90–100%) to the sequence of FIG. 1 in the ectodomain and at least 85% identity (preferably 90%, most preferably 95–100%) in the intracellular domains.

By "identity" is meant a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements may have a lower degree of identity. MDK1.T1, MDK1.T2, MDK1.Δ1 and MDK1.Δ2 are all examples of sequences with sufficient identity to the sequence of FIG. 1 to be considered a MDK1 receptor tyrosine kinase. Those skilled in the art will recognize that several computer programs are available for determining sequence identity.

By "MDK1 binding partner" is meant an amino acid sequence that interacts with or binds a MDK1 RTK. The term includes ligands and/or substrates for the MDK1 kinase.

By "disrupt" is meant that the interaction between the MDK1 receptor tyrosine kinase and a MDK1 binding partner is reduced either by preventing expression of the MDK1 receptor tyrosine kinase, or by preventing expression of the MDK1 binding partner, or by specifically preventing interaction of the naturally synthesized proteins having these domains or by interfering with the interaction of the proteins.

By "promote" is meant that the interaction between a MDK1 receptor tyrosine kinase and a MDK1 binding partner is increased either by increasing expression of a MDK1 receptor tyrosine kinase, or by increasing expression of a MDK1 binding partner, or by decreasing the dephosphorylating activity of the corresponding regulatory TP (or other phosphatase acting on other phosphorylated signalling components) by promoting interaction of the MDK1 receptor tyrosine kinase and a MDK1 binding partner or by prolonging the duration of the interaction. Many bivalent or polyvalent linking agents are useful in coupling polypeptides, such as an antibody, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, *J. Immunol.* 133:1335–2549; Jansen, F. K., et al. 1982, *Immunological Rev.* 62:185–216; and Vitetta et al., supra).

By "signal transduction pathway" is meant the sequence of events that involves the transmission of a message from an extracellular protein to the cytoplasm through a cell membrane. The signal ultimately will cause the cell to perform a particular function, for example, to uncontrollably proliferate and therefore cause cancer. Various mechanisms for the signal transduction pathway (Fry et al., *Protein Science*, 2:1785–1797, 1993) provide possible methods for measuring the amount or intensity of a given signal. Depending upon the particular disease associated with the abnormality in a signal transduction pathway, various symptoms may be detected. Those skilled in the art recognize those symptoms that are associated with the various other diseases described herein. Furthermore, since some adapter molecules recruit secondary signal transducer proteins towards the membrane, one measure of signal transduction is the concentration and localization of various proteins and complexes. In addition, conformational changes that are involved in the transmission of a signal may be observed using circular dichroism and fluorescence studies.

In a related aspect the invention features a method for screening for an agent useful for treatment of such a disease or condition by assaying potential agents for the ability to disrupt or promote that interaction. The screening may also involve assaying potential agents for the ability to remove or reduce the effect of an abnormality in a signal transduction pathway, wherein the signal transduction pathway contains a MDK1 receptor tyrosine kinase and a MDK1 binding partner.

By "screening" is meant investigating an organism for the presence or absence of a property. The process may include measuring or detecting various properties, including the level of signal transduction and the level of interaction between a MDK1 receptor tyrosine kinase and a MDK1 binding partner.

Useful agents for treatment of such diseases can be identified by standard screening protocols in which measurement of such interaction is determined. For example, such an agent may be a peptide which either comprises, consists of, or consists essentially of a MDK1 receptor tyrosine kinase or, alternatively, a fragment thereof.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In preferred embodiments the screening involves looking for agonists or antagonists of a protein of interest, for example MPK1 or a MDK1 binding partner. The term agonist refers to agents that bind the protein and that maintain the activity of the protein to which they bind. An antagonist competes with the natural ligand for binding the protein, but does not maintain the activity of the protein to which it binds.

Another aspect of the invention features a method for diagnosis of such a disease or condition. The method includes detecting the level of interaction between a MDK1 receptor tyrosine kinase and a MDK1 binding partner.

By "diagnosis" is meant any method of identifying a symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between the MDK1 receptor tyrosine kinases and binding partners for the kinases may form the basis to define and diagnose a newly named disease or condition.

For example, conventional neurological diseases are classified according to the presence of a particular set of symptoms. However, a subset of these symptoms may both be associated with an abnormality in a particular signalling pathway, such as the ras[21] pathway and in the future these diseases may be reclassified as ras[21] pathway diseases regardless of the particular symptoms observed.

In preferred embodiments the MDK1 receptor tyrosine kinase has conserved cysteine residues in the ectodomain and has FN III domains as shown in FIG. 1, is selected from the group consisting of MDK1.T1, MDK1.T2, MDK1.Δ1 and MDK1.Δ2 as shown in FIG. 2, has a tyrosine residue substituted for the phenylanaline residue at position 600, has a molecular weight of 114–120 kD, and has an intracellular domain with a molecular weight of 47 kD. Residues 18–538 defining the extracellular domain are one example of a fragment, as are other smaller or larger sequences. The MDK1 RTK may contain the key amino acids of the catalytic domain that are highlighted in bold italics in FIG. 1 and have a similar three dimensional structure to the sequence given in FIG. 1, but may have various substitutions, deletions, or additions at non-key residues, as long the sequence still binds the binding partner. In other preferred embodiments the agent is therapeutically effective and has an $EC_{50}$ or $IC_{50}$ as described below. An $EC_{50}$ or $IC_{50}$ of less than or equal to 5 $\mu M$ is preferable, and even more preferably less than or equal to 1 $\mu M$, 100 nmolar, 10 nmolar, or 1 nmolar. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness. In addition, the molecule may have an $EC_{50}$ or $IC_{50}$ less than or equal to 5 $\mu M$ at one or more, but not all cells chosen from the group consisting of parathyroid cell, bone osteoclast, juxtaglomerular kidney cell, proximal tubule kidney cell, distal tubule kidney cell, cell of the thick ascending limb of Henle's loop and/or collecting duct, central nervous system cell, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition. Generally, a therapeutically effective amount is between about 1 nmole and 1 $\mu$mole of the molecule, depending on its $EC_{50}$ or $IC_{50}$ and on the age and size of the patient, and the disease associated with the patient.

In a further related aspect, the invention features a method of identifying the receptor tyrosine phosphatase responsible for dephosphorylating the activated MDK1 receptor, thereby regulating the MDK1 receptor signaling pathway. Novel methods of treatment of disorders (e.g., neurological disorders) can be based on modulating this phosphatase activity. Modulation of the RTP activity can be accomplished in a variety of ways including but not limited to the use of compounds or drugs that inhibit or enhance the RTP activity, antisense or ribozyme approaches that "knock out" the RTP activity, or gene therapy approaches to correct defects in the RTP or restore the regulated expression of the RTP. Compounds can be used that specifically modulate the activity of the controlling RTP, thereby prolonging or enhancing signal transduction mediated by the MDK1 receptor.

In another aspect the invention features a method for screening for human cells containing a MDK1 RTK or an equivalent sequence (i.e., one that performs a similar function in humans to that played by MDK1 in mice). The method involves identifying the novel RTK in human cells using techniques that are routine and standard in the art, such as those described herein for identifying MDK1 in mouse cells (e.g., cloning, Southern or Northern blot analysis, in situ hybridization, PCR amplification, etc.).

In preferred embodiments the method features screening cells involved in human neurological functions, such as nerve cells, for the presence of MDK1. The invention also features methods of screening human cells for binding partners of MDK1 RTKs and screening other organisms for MDK1 or the corresponding binding partner. In other preferred embodiments the agent is therapeutically effective and has an $EC_{50}$ or $IC_{50}$ as described herein.

In other aspects, the invention provides transgenic, non-human mammals containing a transgene encoding a MDK1 polypeptide or a gene effecting the expression of a MDK1 polypeptide. Such transgenic nonhuman mammals are particularly useful as an in vivo test system for studying the effects of introducing a MDK1 polypeptide, regulating the expression of a MDK1 polypeptide (i.e., through the introduction of additional genes, antisense nucleic acids, or ribozymes).

A "transgenic animal", is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human MDK1 polypeptide. Native expression in an animal may be reduced by providing an amount of anti-sense RNA or DNA effective to reduce expression of the receptor.

In another aspect, the invention describes a polypeptide comprising a recombinant MDK1 polypeptide or a unique fragment thereof. By "unique fragment," is meant an amino acid sequence present in a full-length MDK1 polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence.

By "recombinant MDK1 polypeptide" is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In another aspect, the invention describes a recombinant cell or tissue containing a purified nucleic acid coding for a MDK1 polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the MDK1 polypeptide.

In another aspect, the invention features a MDK1 polypeptide binding agent able to bind to a MDK1 polypeptide. The binding agent is preferably a purified antibody which recognizes an epitope present on a MDK1 polypeptide. Other binding agents include molecules which bind to the MDK1 polypeptide and analogous molecules which bind to a MDK1 polypeptide.

By "purified" in reference to an antibody is meant that the antibody is distinct from naturally occurring antibody, such as in a purified form. Preferably, the antibody is provided as a homogeneous preparation by standard techniques. Uses of antibodies to the cloned polypeptide include those to be used as therapeutics, or as diagnostic tools.

The summary of the invention described above is non-limiting and other features and advantages of the invention will be apparent from the following description of the preferred embodiments, and from the claims.

BRIEF DESCRIPTION OF THE DRAWINGS

FIG. 1 shows the nucleotide (as set forth in SEQ ID NO: 1) and predicted amino acid sequence (as set forth in SEQ ID NO: 2) of a MDK1 RTK. MDK1 full-length nucleotide (3628 bp) and deduced amino acid sequence (998 amino acids) are shown. The predicted initiating methionine (Kozak, M., *Nucleic Acids Res.* 12:857–872, 1984) and signal peptide (Heijne, G.v., *Nucleic Acids Res.* 14:4683–4690, 1986) are underlined. Although preceded by two putative methionine codons at bases 124 and 226, these codons are followed by in-frame stop codons after 4 and 59 amino acids, respectively. In addition, they are surrounded by weak consensus sequences for initiation sites, while the proposed initiating methionine comprises a strong initiation sequence (Kozak, M., *Nucleic Acids Res.* 12:857–872, 1984) preceded by an in-frame stop codon. The putative transmembrane domain is underlined, the potential N-glycosylation sites boxed and the conserved extracellular cysteines are circled. Key amino acids of the catalytic domain of MDK1 are highlighted in bold italics. The polyadenylation motif(AATAAA) (SEQ. I.D. NO. 7) is underlined, the alternative 3'-untranslated region of MDK1 is given below.

FIG. 2 shows the overview of various forms of MDK1 RTKs. FIG. 2A shows the nucleotide sequence of MDK1.T1 (as set forth in SEQ ID NO: 4) beginning with nucleotide 1913, and FIG. 2B shows the nucleotide sequence of MDK1.T2 (as set forth in SEQ ID NO: 6) beginning with nucleotide 1913. The divergent sequence due to alternative splicing is shown underlined, as is the polyadenylation motif(AATAAA) (SEQ I.D NO: 8) in the sequence of MDK1.T1.

DESCRIPTION OF THE PREFERRED EMBODIMENTS

Figure 2C:
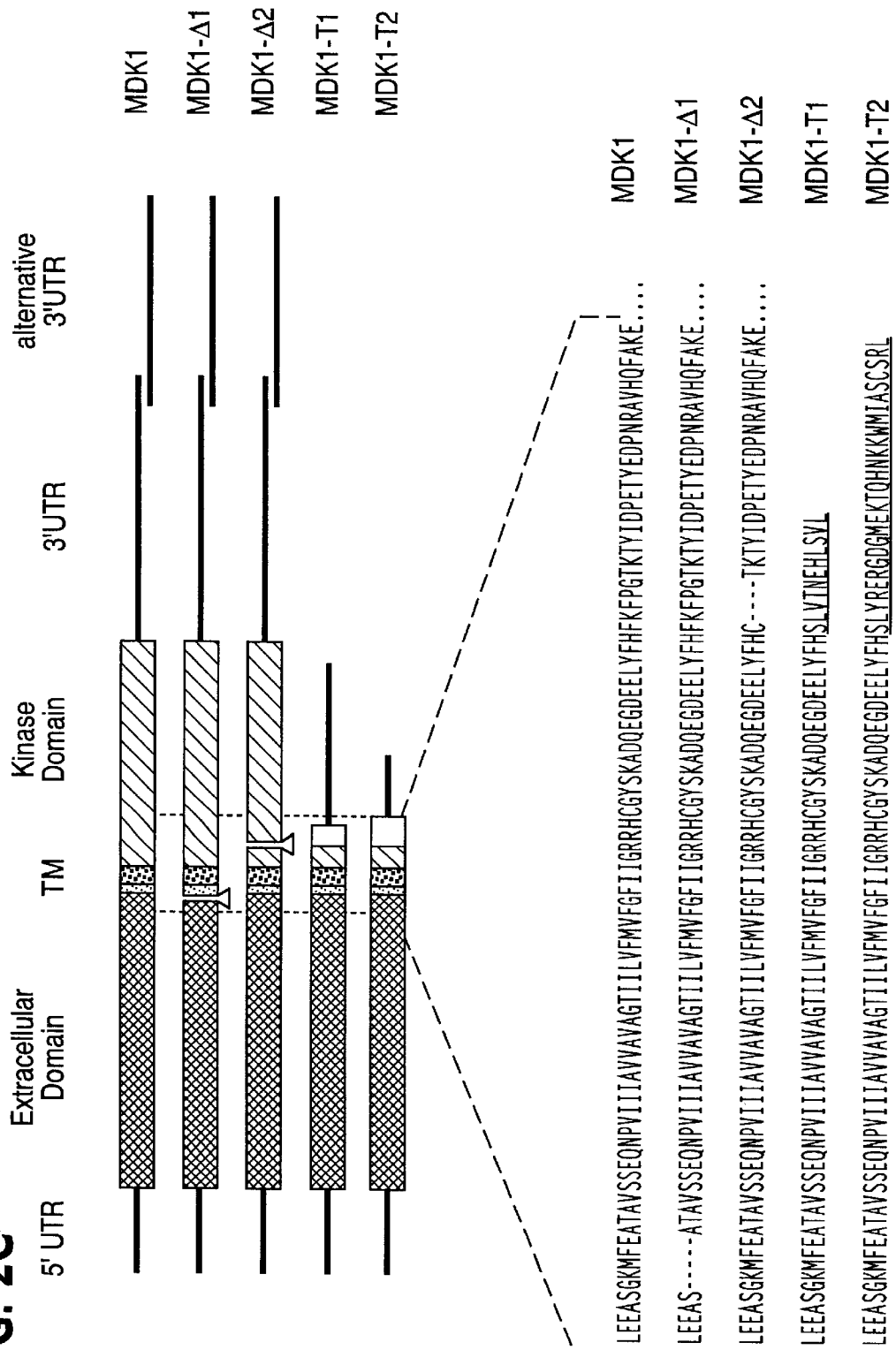
FIG. 2C shows a schematic representation of MDK1 and its variants. The open reading frame is indicated by boxes, the untranslated regions of the MDK1 sequences are given in bold lines. Below, the amino acid sequence variations in the marked region of the different forms of MDK1 are shown. The missing nucleotide stretches are indicated ( - - - ). The sequences shown each begin at amino acid residue number 535 in MDK1 (SEQ ID NO: 2), MDK1.T1 (SEQ ID NO: 3), MDK1.T2 (SEQ ID NO: 5), MDK1.Δ6 (SEQ ID NO: 11), and MDK1.Δ2 (SEQ ID NO: 12).

The present invention relates to MDK1 polypeptides, nucleic acids encoding such polypeptides, cells, tissues and animals containing such nucleic acids, antibodies to such polypeptides, assays utilizing such polypeptides, and methods relating to all of the foregoing.

The present invention is based upon the isolation of MDK1, a new member of the eck/eph family of RTKs. MDK1 was identified and shown to be closely related to Eek, Ehk1/Cek7, Ehk2, Cek4/Mek4/hek, and Sek/Cek8 subfamily. cDNA cloning using adult mouse brains and Northern blot analysis revealed MDK1 mRNA transcripts of 6.8, 5.7, 4.0, 3.2, and 2.6 kb that encode apparent splice variants and indicate that MDK1 is expressed in at least five variant forms, including two full-length receptors that display short amino acid deletions in their extra- and intracellular domains. The existence of multiple receptor forms with short insertion sequences in their juxtamembrane regions and N-terminal of the transmembrane domain has already been described for Ehk-1 (Maisonpierre et al., *Oncogene* 8:3277–3288, 1993), Cek5, Cek6, and Cek10 (Sajjadi and Pasquale, *Oncogene* 8:1807–1813, 1993), other members of the large eck/eph RTK subfamily. Further examination of other RTKs of this family may also reveal the generation of variant mRNAs, as suggested by the identification of a testes-specific transcript for Mek4 (Sajjadi et al., *New Biol.* 3:769–778, 1991). Northern blot and in situ hybridization analysis in the adult mouse indicated that RNA expression is restricted to brain, testes, and spleen. The distinct patterns of MDK1 expression during mouse development suggest an important role for MDK1 in the formation of neuronal structures.

The physiological role of the amino acid deletions in MDK1Δ1 and MDK1Δ2 is currently unclear. However, the amino acid exchange of amino acid 600 from phenylalanine to cysteine in MDK1Δ2 changes the motif $Y^{597}$FHF to $Y^{597}$FHC, which since the first three amino acids following a phosphotyrosine define the binding specificity of src-homology 2 (SH2) domain-containing proteins to activated RTKs (Songyang et al., *Cell* 72:767–778, 1993), may result in redefinition of the MDK1 signal and thereby the response of the cell.

The cDNA cloning and Northern blot analysis demonstrate the existence of two truncated versions of MDK1 that possess the entire ectodomain, the transmembrane domain, and part of the juxtamembrane region, but lack the catalytic tyrosine kinase domain. Similarly, for the closely related RTK MEK4, a putative secreted form has been reported consisting of the ectodomain only, although the expression of a corresponding transcript in any of the tissues examined could not be demonstrated (Sajjadi et al., *New Biol.* 3:769–778, 1991). Analogous truncated forms of RTKs that lack the catalytic domain but are still anchored in the cell membrane have been described for trkB (Klein et al., *Cell* 61:647–656, 1990; Middlemas et al., *Mol. Cell. Biol.* 11:143–153, 1991), trkC (Valenzuela et al., *Neuron* 10:963–974, 1993), the heparin-binding fibroblast growth factor (HBGF) receptor (Hou et al., *Science* 251:665–668, 1991), and ltk (Toyoshima et al., *Proc. Natl. Acad. Sci. USA* 90:5404–5408, 1993). In the case of trkB, expression of this isoform is restricted to the ependymal linings of cerebral ventricles and choroid plexus structures of the mouse forebrain, indicative of a putative role in ligand transport across the blood-brain barrier (Klein et al., *Cell* 61:647–656, 1990).

While similar findings have been reported for the truncated forms of trkC (Valenzuela et al., *Neuron* 10:963–974, 1993), additional interpretations of the physiological role of MDK1.T1 and MDK1.T2 are suggested by their divergence in C-terminal sequences, which may interact differentially with cytoplasmic proteins involved in MDK1 signal transduction. As suggested by experiments with artificially truncated receptors for epidermal growth factor receptor (EGF-R), fibroblast growth factor, and vascular endothelial growth factor, such mutants may impair or modulate signal transduction by the native receptors.

Since RTKs are thought to function as dimers, the formation of heterodimers between a normal and a truncated mutant receptor prevents transphosphorylation and therefore suppresses the activation of receptor signaling functions (Kashles et al., *Mol. Cell. Biol.* 11:1454–1463, 1991; Redemann et al., *Mol. Cell. Biol.* 12:491–498, 1992). Such a modulatory function through dominant negative inhibition for MDK1-T1 and T2 would require expression of dominant negative truncated and the full-length receptors within the same cell. To address this potentially important aspect of MDK1 function, the spatial and temporal expression of MDK1.T1 and MDK1.T2 in comparison with the full-length forms during mouse development can be investigated.

MDK1 RTKs show autophosphorylation after inhibition of cellular phosphotyrosine phosphatases. Its predicted protein sequence possesses all of the important amino acids conserved in the catalytic domain of tyrosine kinases (Hanks et al., *Science* 241:42–52, 1988). MDK1 RTKs migrate as a protein doublet of an apparent molecular weight of approximately 114 kD and 120 kD, the larger band corresponding to the major, glycosylated protein. The lower 114 kD precursor form of MDK1 RTKs is probably due to overloading of the processing enzymes in the transient overexpression system used. The observed sizes are similar to the apparent molecular weights of 120 kD reported for Cek5 (Pasquale, E. B., *Cell Regula.* 2:523–534, 1991), 130 kD for eph (Maru et al., *Oncogene* 5:445–447, 1990), and 130 kD for elk (Lhotak et al., *Mol. Cell. Biol.* 11:2496–2502, 1991). Eck has been described to migrate as a doublet of 125 kD and 130 kD (Lindberg and Hunter, *Mol. Cell. Biol.* 10:6316–6324, 1990).

A prominent protein of an apparent molecular weight of 47 kD found in all immunoprecipitations with antibodies directed against either the C-terminal amino acids of MDK1 RTKs or phosphotyrosines is believed to correspond to the intracellular domain of MDK1 RTKs. It is only found in cells transfected with receptor DNA and is not a substrate of MDK1. Protein bands of approximately 60 kD and 53 kD have been detected in immunoprecipitations of eck (Lindberg and Hunter, *Mol. Cell. Biol.* 10:6316–6324, 1990) and elk (Lhotak et al., *Mol. Cell. Biol.* 11:2496–2502, 1991), respectively.

The situation resembles that found for the colony-stimulating factor 1 receptor (CSF1-R). CSF1-R is downregulated through two entirely different mechanisms, one of which makes use of a protein kinase C (PKC) activated protease. The action of this protease results in an inducible proteolytic cleavage of the CSF1-R near the transmembrane domain, releasing an intracellular fragment containing the kinase domain (Downing et al., *Mol. Cell. Biol.* 9:2890–2896, 1989). Such a specific proteolytic action on RTKs could downmodulate the activity of the kinases. If such a regulation of MDK1 exists it may be important under physiological conditions.

As revealed through Northern blot and in situ hybridization analysis, MDK1 displays a rather wide-spread expression pattern in the early mouse embryo. There is, however, an increasing restriction of MDK1 transcription during embryogenesis, resulting in a predominant expression in the brain of adult mice. Based on its expression sites, MDK1 is likely to be involved in the establishment of the complex neuronal organization of the nervous system, as suggested by its expression in key structures of the central nervous system. MDK1 is found throughout the development of the hippocampal formation and in thalamic structures such as the mammillary body of the hypothalamus and the habenula of the epithalamus, which are important components of the limbic system of the CNS. This system is associated with emotional aspects of behavior related to the survival of the animal and the species, together with visceral responses accompanying these emotions. Additionally, the limbic system is thought to participate in the processes involved in memory formation (Rohen, J. W., *Funktionelle Anatomie des Nervensystems*, Schattauer, N.Y., 1985).

The expression of MDK1 in various sense organs like the ear, the tongue or the vibrissae and in neuronal structures involved in the processing of sensoric signals like the superior colliculus or the trigeminal (V) ganglion could point to an important function of MDK1 in the differentiation of the limbic system, since it is connected to nearly all sensoric organs. Apart from the putative role of MDK1 in the formation of the limbic system, there appears to be a connection between the expression of MDK1 in the Purkinje cell layer of the cerebellum and in the inferior olive of the medulla, since, at least in mammals, this structure is the only source of climbing fibers connecting to the Purkinje cells (Ito, M, *The cerebellum and neuronal control*, Raven Press, New York, 1984).

Figure 3:
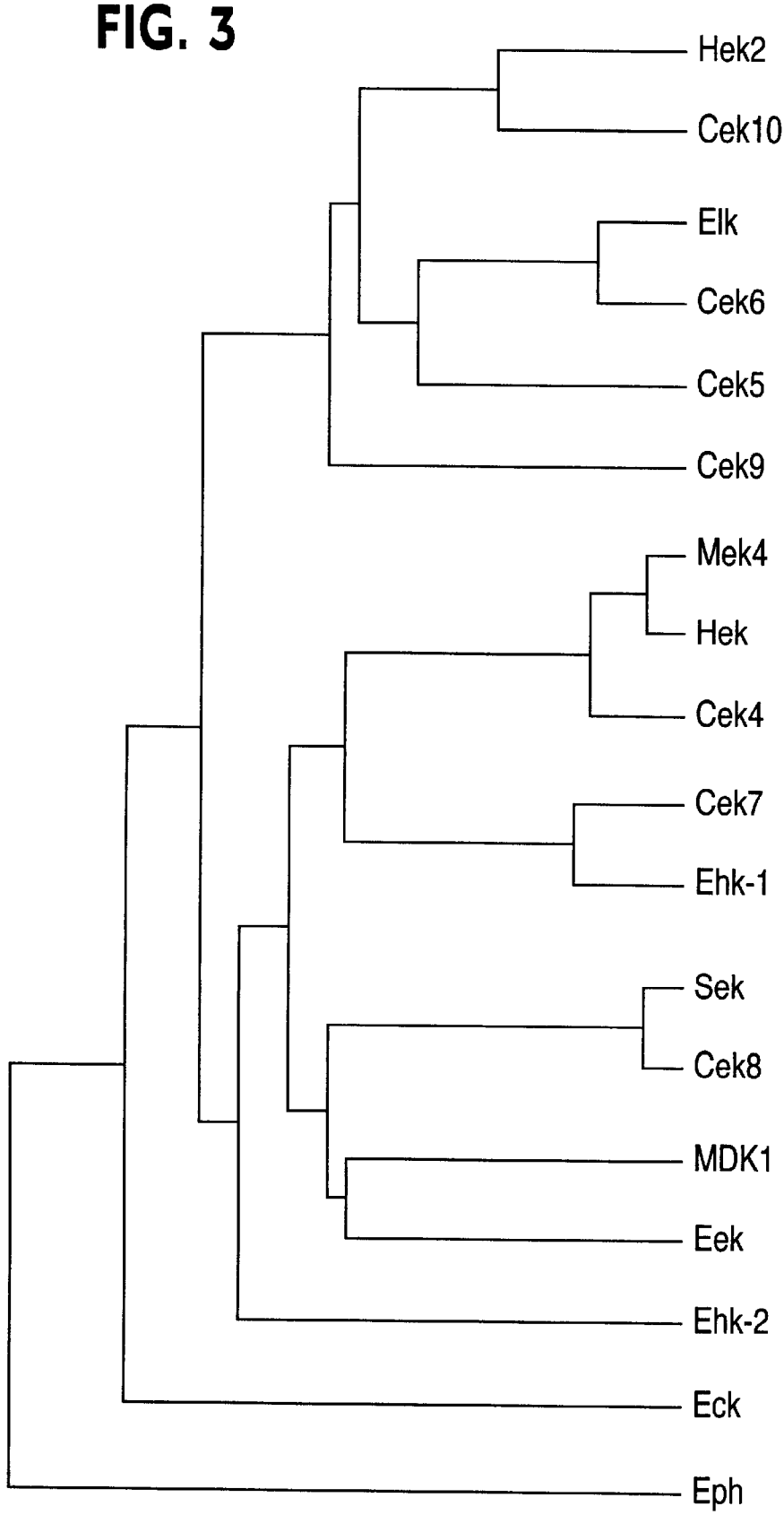
FIG. 3 is a dendrogram for the eck/eph subfamily of RTKs. The predicted protein sequences of MDK1, Hek2 (Böhme et al., 1993), Cek6, 7, 8, 9 and 10 (Sajjadi and Pasquale, *Oncogene* 8:1807–1813, 1993), Elk (Lhotak et al., *Mol. Cell. Biol.* 11:2496–2502, 1991), Cek5 (Pasquale, E. B., *Cell Regula.* 2:523–534, 1991), Mek4, Cek4 (Sajjadi et al., *New Biol.* 3:769–778, 1991 ), Hek (Wicks et al., *Proc. Natl. Acad. Sci. USA* 89:1611–1615, 1992.), Ehk1, Ehk2 (Maisonpierre et al., *Oncogene* 8:3277–3288, 1993), Sek (Gilardi-Hebenstreit et al., *Oncogene* 7:2499–2506, 1992), Eek (Chan and Watt, *Oncogene* 6:1057–1061, 1991), Eck (Lindberg and Hunter, *Mol. Cell. Biol.* 10:6316–6324, 1990) and eph (Hirai et al., *Science* 238:1717–1720, 1987) were aligned using progressive, pairwise alignments according to the method of Higgins and Sharp (Higgins and Sharp, *CABIOS* 5:151–153, 1989). Published sequence data for erk (Chan and Watt, *Oncogene* 6:1057–1061, 1991) and tyrol, 4, 5, 6 and 11 (Lai and Lemke, *Neuron* 6:691–704, 1991) were insufficient for inclusion in the analysis. A tree of sequence similarity generated by use of the Unweighted Pair Group Method with Arithmetic mean algorithm (UPGMA; Sneath and Sokal, in *Numerical Taxonomy*, W. H. Freeman and Company, San Francisco, 1973, pp. 230–234) calculated on basis of the multiple alignment is shown.

MDK1 is a new member of a growing subgroup of eck/eph-like RTKs, which are more related to each other than to any of the remaining eck/eph-like kinases (FIG. 3). In the mouse, the members of this subgroup, MDK1, eek, ehk-1, ehk-2, Mek4, Cek4, Hek, Sek, Cek7, and Cek8, are expressed primarily in the brain, with Cek7 (Sajjadi and Pasquale, *Oncogene* 8:1807–1813, 1993) and eek (Chan and Watt, *Oncogene* 6:1057–1061, 1991) being exclusively expressed in this region. The other kinases are reported to have additional regions of transcription in nonneuronal tissues. Transcripts of Mek4 have been detected at low level in testes (Sajjadi et al., *New Biol.* 3:769–778, 1991). Ehk1 is found faintly in ovary and skin, whereas Ehk2 shows weak signals in skin, skeletal muscle, spleen and thymus (Maisonpierre et al., *Oncogene* 8:3277–3288, 1993). Sek was found to be expressed in specific compartments of the developing hindbrain and in pre-somitic mesoderm and shows supplementary expression in heart, lung and kidney (Gilardi-Hebenstreit et al., *Oncogene* 7:2499–2506, 1992; Nieto et al., *Development* 116:1137–1150, 1992). Cek8 expression is also detectable in kidney, lung, skeletal muscle, and thymus (Sajjadi and Pasquale, *Oncogene* 8:1807–1813, 1993).

The existence of a sub-branch within the eph/eck-family which may have evolved in parallel with the elaboration of diverse cell types in the vertebrate nervous system has already been suggested by Maisonpierre et al. (Maisonpierre et al., *Oncogene* 8:3277–3288, 1993). we believe that this subgroup is likely to grow as further RTKs are identified and will prove to be a diverse family of related kinases involved in the regulation of the development of the central and peripheral nervous systems.

I. Nucleic Acid Encoding a MDK1 Polypeptide

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the MDK1 gene could be synthesized to give a nucleic acid sequence significantly different from that shown in SEQ ID NO: 1. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO: 1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the MDK1 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

II. A Nucleic Acid Probe for the Detection of MDK1

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. Molecular Cloning: A Laboratory Manual, second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, A Guide to Methods and Applications, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. Molecular Cloning: A Laboratory Manual, second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. A Probe Based Method and Kit for Detecting MDK1

One method of detecting the presence of MDK1 in a sample comprises a) contacting said sample with the above-described nucleic acid probe, under conditions such that hybridization occurs, and b) detecting the presence of said probe bound to said nucleic acid molecule. One skilled in the art would select the nucleic acid probe according to techniques known in the an as described above. Samples to be tested include but should not be limited to RNA samples of human tissue.

A kit for detecting the presence of MDK1 in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

IV. DNA Constructs Comprising a MDK1 Nucleic Acid Molecule and Cells Containing These Constructs The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecules. The present invention also relates to a nucleic acid molecule comprising a transcriptional region functional in a cell, a sequence complimentary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule. The peptide may be purified from cells which have been altered to express the peptide. A cell is said to be "altered to express a desired peptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an MDK1 gene may be obtained by the above-described methods. This region may be retained for its transcriptional termination regulatory sequences, such as termination and polyadenylation. Thus, by retaining the 3'-region naturally contiguous to the DNA sequence encoding an MDK1 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an MDK1 sequence) are said to be operably linked if the nature of the linkage between the two DNA sequences does not (1) result in the introduction of a frame-shift mutation, (2) interfere with the ability of the promoter region sequence to direct the transcription of an MDK1 gene sequence, or (3) interfere with the ability of the an MDK1 gene sequence to be transcribed by the promoter region sequence. Thus, a promoter region would be operably linked to a DNA sequence if the promoter were capable of effecting transcription of that DNA sequence. Thus, to express an MDK1 gene, transcriptional and translational signals recognized by an appropriate host are necessary.

The present invention encompasses the expression of the MDK1 gene (or a functional derivative thereof) in either prokaryotic or eukaryotic cells. Prokaryotic hosts are, generally, very efficient and convenient for the production of recombinant proteins and are, therefore, one type of preferred expression system for the MDK1 gene. Prokaryotes most frequently are represented by various strains of E. coli. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as E. coil, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express MDK1 (or a functional derivative thereof) in a prokaryotic cell, it is necessary to operably link the MDK1 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of E. coli, the α-amylase (Ulmanen et at., J. Bacteriol. 162:176–182 (1985)) and the ζ-28-specific promoters of B. subtilis (Gilman et at., Gene sequence 32:11–20(1984)), the promoters of the bacteriophages of Bacillus (Gryczan, In: The Molecular Biology of the Bacilli, Academic Press, Inc., New York (1982)), and Streptomyces promoters (Ward et at., Mol. Gen. Genet. 203:468–478(1986)). Prokaryotic promoters are reviewed by Glick (J. Ind. Microbiot. 1:277–282 (1987)); Cenatiempo (Biochimie 68:505–516(1986)); and Gottesman (Ann. Rev. Genet. 18:415–442 (1984)).

Proper expression in a prokaryotic cell also requires the presence of a ribosome binding site upstream of the gene sequence-encoding sequence. Such ribosome binding sites are disclosed, for example, by Gold et at. (Ann. Rev. Microbiol. 35:365–404(1981)). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the MDK1 peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the *Drosophila larvae*. Using insect cells as hosts, the Drosophila alcohol dehydrogenase promoter can be used. Rubin, Science 240:1453–1459(1988). Alternatively, baculovirus vectors can be engineered to express large amounts of MDK1 in insects cells (Jasny, Science 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of MDK1.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of MDK1 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273–288(1982)); the TK promoter of Herpes virus (McKnight, Cell 31:355–365 (1982)); the SV40 early promoter (Benoist et al., Nature (London) 290:304–310 (1981)); the yeast gal4 gene sequence promoter (Johnston et al., Proc. Natl. Acad. Sci. (USA) 79:6971–6975(1982); Silver et al., Proc. Natl. Acad. Sci. (USA) 81:5951–5955 (1984)).

Translation of eukaryotic mRNA is initiated at the codon which encodes the first methionine. For this reason, it is preferable to ensure that the linkage between a eukaryotic promoter and a DNA sequence which encodes MDK1 (or a functional derivative thereof) does not contain any intervening codons which are capable of encoding a methionine (i.e., AUG). The presence of such codons results either in a formation of a fusion protein (if the AUG codon is in the same reading frame as the MDK1 coding sequence) or a frame-shift mutation (if the AUG codon is not in the same reading frame as the MDK1 coding sequence).

A MDK1 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, Molec. Cell. Biol. 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColEl, pSC101, PACYC 184, πVX. Such plasmids are, for example, disclosed by Sambrook (cf. Molecular Cloning: A Laboratory Manual, second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, New York (1982), pp. 307–329). Suitable Streptomyces plasmids include p1J101 (Kendall et al., J. Bacteriol. 169:4177–4183 (1987)), and streptomyces bacteriophages such as øC31 (Chater et al., In: Sixth International Symposium on Actinomycetales Biology, Akademiai Kaido, Budapest, Hungary (1986), pp. 45–54). Pseudomonas plasmids are reviewed by John et al. (Rev. Infect. Dis. 8:693–704(1986)), and Izaki (Jpn. J. Bacteriol. 33:729–742(1978)).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274(1982); Broach, In: The Molecular Biology of the Yeast 30 Saccharomyces: Life Cycle and Inheritance, Cold Spring Harbor Laboratory, Cold Spring Harbor, N.Y., p. 445–470 (1981); Broach, Cell 28:203–204 (1982); Bollon et at., J. Ctin. Hematol. Oncol. 10:39–48 (1980); Maniatis, In: Cell Biology: A Comprehensive Treatise, Vol. 3, Gene Sequence Expression, Academic Press, New York, pp. 563–608(1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of MDK1 or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

V. Purified MDK1 Polypeptides

A variety of methodologies known in the art can be utilized to obtain the peptide of the present invention. The peptide may be purified from tissues or cells which naturally produce the peptide. Alternatively, the above-described isolated nucleic acid fragments could be used to expressed the MDK1 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

VI. An Antibody Having Binding Affinity to a MDK1 Polypeptide and a Hybridoma Containing the Antibody The present invention relates to an antibody having binding affinity to a MDK1 polypeptide. The polypeptide may have the amino acid sequence set forth in SEQ ID NO:2, or functional derivitive thereof, or at least 9 contiguous amino acids thereof (preferably, at least 10, 15, 20, or 30 contiguous amino acids thereof).

The present invention also relates to an antibody having specific binding affinity to an MDK1 polypeptide. Such an antibody may be isolated by comparing its binding affinity to a MDK1 polypeptide with its binding affinity to another polypeptide. Those which bind selectively to MDK1 would be chosen for use in methods requiring a distinction between MDK1 and other polypeptides. Such methods could include, but should not be limited to, the analysis of altered MDK1 expression in tissue containing other polypeptides such as FAK.

The MDK1 proteins of the present invention can be used in a variety of procedures and methods, such as for the generation of antibodies, for use in identifying pharmaceutical compositions, and for studying DNA/protein interaction.

The MDK1 peptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1–21(1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124 (1988)). Hybridomas secreting the desired antibodies are cloned and the class and subclass is determined using procedures known in the art (Campbell, Monoclonal Antibody Technology: Laboratory Techniques in Biochemistry and Molecular Biology, supra (1984)).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger et al., J. Histochem. Cytochem. 18:315(1970); Bayer et at., Meth. Enzm. 62:308(1979); Engval et al., Immunot. 109:129(1972); Goding, J. Immunol. Meth. 13:215(1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10(1986); Jacoby et al., Meth. Enzym. 34 Academic Press, New York (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W.H. Freeman, New York, pp. 289–307(1992), and Kaspczak et al., Biochemistry 28:9230–8(1989).

Anti-peptide peptides can be generated by replacing the basic amino acid residues found in the MDK1 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VII. An Antibody Based Method and Kit for Detecting MDK1

The present invention encompasses a method of detecting an MDK1 polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. Altered levels of MDK1 in a sample as compared to normal levels may indicate muscular disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

A kit contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

VIII. Isolation of Compounds Which Interact with MDK1

The present invention also relates to a method of detecting a compound capable of binding to a MDK1 polypeptide comprising incubating the compound with MDK1 and detecting the presence of the compound bound to MDK1. The compound may be present within a complex mixture, for example, serum, body fluid, or cell extracts.

The present invention also relates to a method of detecting an agonist or antagonist of MDK1 activity comprising incubating cells that produce MDK1 in the presence of a compound and detecting changes in the level of MDK1 activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing MDK1 associated activity in a mammal comprising administering to said mammal an agonist or antagonist to MDK1 in an amount sufficient to effect said agonism or antagonism. A method of treating diabetes mellitus, skeletal muscle diseases, Alzheimer's disease, or peripheral neuropathies in a mammal with an agonist or antagonist of MDK1 activity comprising administering the agonist or antagonist to a mammal in an amount sufficient to agonize or antagonize MDK1 associated functions is also encompassed in the present application.

IX. Transgenic Animals

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438–4442 (1985)). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47: 897–905 (1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell* 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science* 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel et al., *Science* 244:1281–1288 (1989); and Simms et al., *Bio/Technology* 6:179–183 (1988).

X. Compositions

The present invention relates to removing or reducing an abnormality in a signal transduction pathway, wherein the signal transduction pathway contains a MDK1 receptor tyrosine kinase and a MDK1 binding partner. The present invention also relates to compositions and methods for the treatment of disorders which involve modulating the activity and/or level of individual components, and relates to methods for the identification of agents for such treatments. Additionally, the present invention relates to methods and compositions for prognostic evaluation of such disorders.

Described herein are compositions and methods for the prevention, prognostic evaluation, and treatment of neurodegenerative or neuroproliferative disorders, especially disorders such as Alzheimer's disease, Parkinson's disease, Lou Gehrig's disease (ALS), trauma, damaged or severed nerve injuries, Huntington's chorea, multiple sclerosis, muscular dystrophy, syringomiplia, Tabes Dorsalis, cardiovascular accidents, and other disorders described herein, in which a MDK1 receptor tyrosine kinase may be involved. Also described are compositions and methods for the prevention, prognostic evaluation and treatment of cell proliferative disorders, especially cancer, in which a MDK1 receptor tyrosine kinase is involved.

First, methods and compositions for the treatment of such disorders are described. Such methods and compositions may include, but are not limited to the agents capable of decreasing or inhibiting the interaction between a MDK1 receptor tyrosine kinase and a MDK1 binding partner and agents capable of inhibiting or decreasing the activity of such complexes, agents capable of modulating the activity and/or level of individual components of the proteins, and the use and administration of such agents. Agents capable of modulating the activity and/or level of interaction between MDK1 receptor tyrosine kinase and a MDK1 binding partner include those agents that inhibit or decrease the dephosphorylating activity of tyrosine phosphatases.

Second, methods are described for the identification of such agents. These methods may include, for example, assays to identify agents capable of disrupting or inhibiting or promoting the interaction between components of the complexes (e.g., MDK1:binding partner complexes), and may also include paradigms and strategies for the rational design of drugs capable of disruption and/or inhibition and/or promotion of such complexes.

XI. Binding Partner/Receptor Complexes

The complexes involved in the invention include a MDK1 receptor tyrosine kinase and a MDK1 binding partner or derivatives thereof, as described below. Under standard physiological conditions, the components of such complexes are capable of forming stable, non-covalent attachments with one or more of the other complex components. Methods for the purification and production of such protein complexes, and of cells that exhibit such complexes are described below.

The complexes involved in the invention also include tyrosine phosphatases responsible for dephosphorylating activated MDK1 receptors, thus modulating the ability to bind to a binding partner and other signal transduction components. Identification of such tyrosine phosphatase(s) may be accomplished using techniques known to one skilled in the art.

XII. Disruption of Protein Complexes

Disruption of complexes (e.g., MDK1:binding partner complexes), for example by decreasing or inhibiting or promoting the interactions between component members of such a complex may have differing modulatory effects on the event involved, depending on the individual protein complex. "Disruption", as used here, is meant to refer not only to a physical separation of protein complex components, but also refers to a perturbation of the activity of the complexes, regardless of whether or not such complexes remain able, physically, to form. "Activity", as used here, refers to the function of the protein complex in the signal transduction cascade of the cell in which such a complex is formed, i.e., refers to the function of the complex in effecting or inhibiting a transduction of an extracellular signal into a cell. For example, the effect of complex disruption may augment, reduce, or block a signal normally transduced into the cell. Likewise, depending on the disorder involved, either augmentation, reduction, or blockage of a signal normally transduced into the cell will be desirable for the treatment of the disorder.

A disorder involving a complex may, for example, develop because the presence of such a complex brings about the aberrant inhibition of a normal signal transduction event. In such a case, the disruption of the complex would allow the restoration of the usual signal transduction event. Further, an aberrant complex may bring about an altered subcellular adapter protein localization, which may result in, for example, dysfunctional cellular events. An inhibition of the complex in this case would allow for restoration or maintenance of a normal cellular architecture. Still further, an agent or agents that cause(s) disruption of the complex may bring about the disruption of the interactions among other potential components of a complex.

Nucleotide sequences encoding peptide agents which are to be utilized intracellularly may be expressed in the cells of interest, using techniques which are well known to those of ordinary skill in the art. For example, expression vectors derived from viruses such as retroviruses, vaccinia virus, adenoviruses, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al., 1989, *Molecular Cloning: A Laboratory Manual*, Cold Spring Harbor Laboratory, New York and in Ausubel et al., *Current Protocols in Molecular Biology*, Greene Publishing Associates and Wiley Interscience, New York, 1989. Complex-binding domains can be identified using, for example, techniques such as those described in Rotin et al. (Rotin et al., *EMBO J.* 11:559–567, 1992), Songyang et al. (Songyang et al., *Cell* 72:767–778, 1993), Felder et al., *Mol. Cell. Biol.* 13:1449–1455, 1993), Fantl et al. (*Cell* 69:413–422, 1992), and Domchek et al. (*Biochemistry* 31:9865–9870, 1992).

Alternatively, antibodies capable of interfering with complex formation may be produced as described below and administered for the treatment of disorders involving a component capable of forming a complex with another protein. For example, neutralizing antibodies which are capable of interfering with ligand binding may be administered using standard techniques. Alternatively, nucleotide sequences encoding single-chain antibodies may be expressed within the target cell population by utilizing, for example, techniques such as those described in Marasco et al. (Marasco et al., *Proc. Natl. Acad. Sci. USA* 90:7889–7893, 1993).

Agents which act intracellularly to interfere with the formation and/or activity of the protein complexes of the invention may also be small organic or inorganic compounds. A method for identifying these and other intracellular agents is described below.

XIII. Antibodies to Complexes

Described herein are methods for the production of antibodies which are capable of specifically recognizing a complex or an epitope thereof, or of specifically recognizing an epitope on either of the components of the complex, especially those epitopes which would not be recognized by the antibody when the component is present separate and apart from the complex. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a complex in a biological sample, or, alternatively, as a method for the inhibition of a complex formation, thus inhibiting the development of a disorder.

Polyclonal antibodies are heterogeneous populations of antibody molecules derived from the sera of animals immunized with an antigen, such as a complex, or an antigenic functional derivative thereof. For the production of polyclonal antibodies, various host animals may be immunized by injection with the complex including but not limited to rabbits, mice, rats, etc. Various adjuvants may be used to increase the immunological response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

A monoclonal antibody, which is a substantially homogeneous population of antibodies to a particular antigen, may be obtained by any technique which provides for the production of antibody molecules by continuous cell lines in culture. These include, but are not limited to the hybridoma technique of Kohler and Milstein (*Nature* 256:495–497, 1975) and U.S. Pat. No. 4,376,110), the human B-cell hybridoma technique (Kosbor et al., *Immunology Today* 4:72, 1983; Cole et al., *Proc. Natl. Acad. Sci. USA* 80:2026–2030, 1983), and the EBV-hybridoma technique (Cole et al., *Monoclonal Antibodies And Cancer Therapy*, Alan R. Liss, Inc., 1985, pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mabs in vivo makes this the presently preferred method of production.

In addition, techniques developed for the production of "chimeric antibodies" (Morrison et al., *Proc. Natl. Acad. Sci.*, 81:6851–6855, 1984; Neuberger et al., *Nature*, 312:604–608, 1984; Takeda et al., *Nature*, 314:452–454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423–426, 1988; Huston et al., *Proc. Natl. Acad. Sci. USA* 85:5879–5883, 1988; and Ward et al., *Nature* 334:544–546, 1989) can be adapted to produce complex-specific single chain antibodies. Single chain antibodies are formed by linking the heavy and light chain fragment of the Fv region via an amino acid bridge, resulting in a single chain polypeptide.

Antibody fragments which contain specific binding sites of a complex may be generated by known techniques. For example, such fragments include but are not limited to: the F(ab')₂ fragments which can be produced by pepsin digestion of the antibody molecule and the Fab fragments which can be generated by reducing the disulfide bridges of the F(ab')₂ fragments. Alternatively, Fab expression libraries may be constructed (Huse et al., 1989, Science, 246:1275–1281) to allow rapid and easy identification of monoclonal Fab fragments with the desired specificity to the PTK/adapter complex.

One or more components of a protein complex may be present at a higher than normal cellular level (i.e., higher than the concentration known to usually be present in the cell type exhibiting the protein complex of interest) and/or may exhibit an abnormally increased level of cellular activity (i.e., greater than the activity known to usually be present in the cell type exhibiting the protein complex of interest).

For example, the gene encoding a protein complex component may begin to be overexpressed, or may be amplified (i.e., its gene copy number may be increased) in certain cells, leading to an increased number of component molecules within these cells. Additionally, a gene encoding a protein complex component may begin to express a modified protein product that exhibits a greater than normal level of activity. "Activity", here, refers to the normal cellular function of the component, either enzymatic or structural whose function may include, for example, bringing two or more cellular molecules into the appropriate proximity.

Such an increase in the cellular level and/or activity of a protein complex may lead to the development of a disorder. Treatment of such disorders may, therefore, be effectuated by the administration of agents which decrease the cellular level and/or the activity of the overexpressed and/or overactive protein complex component.

Techniques for decreasing the cellular level and/or the activity of one or more of the protein complex components of interest may include, but are not limited to antisense or ribozyme approaches, and/or gene therapy approaches, each of which is well known to those of skill in the art.

XIV. Antisense and Ribozyme Approaches to Provide or Disrupt the Complexes of the Present Invention Included in the scope of the invention are oligoribonucleotides, including antisense RNA and DNA molecules and ribozymes that function to inhibit translation of one or more components of a protein complex. Anti-sense RNA and DNA molecules act to directly block the translation of mRNA by binding to targeted mRNA and preventing protein translation. With respect to antisense DNA, oligodeoxyribonucleotides derived from the translation initiation site, e.g., between −10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by a endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569.

Both anti-sense RNA and DNA molecules and ribozymes of the invention may be prepared by any method known in the art for the synthesis of RNA molecules. See, Draper, id. hereby incorporated by reference herein. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Gene Therapy

MDK1 or its genetic sequences will also be useful in gene therapy (reviewed in Miller, Nature 35 357:455–460, (1992). Miller states that advances have resulted in practical approaches to human gene therapy that have demonstrated positive initial results. The basic science of gene therapy is described in Mulligan, Science 260:926–931, (1993).

In one preferred embodiment, an expression vector containing the MDK1 coding sequence is inserted into cells, the cells are grown in vitro and then infused in large numbers into patients. In another preferred embodiment, a DNA segment containing a promoter of choice (for example a strong promoter) is transferred into cells containing an endogenous MDK1 in such a manner that the promoter segment enhances expression of the endogenous MDK1 gene (for example, the promoter segment is transferred to the cell such that it becomes directly linked to the endogenous MDK1 gene).

The gene therapy may involve the use of an adenovirus containing MDK1 cDNA targeted to a tumor, systemic MDK1 increase by implantation of engineered cells, injection with MDK1 virus, or injection of naked MDK1 DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant MDK1 protein into the targeted cell population (e.g., tumor cells). Methods which are well known to those skilled in the art can be used to construct recombinant viral vectors containing coding sequences. See, for example, the techniques described in Maniatis et al., *Molecular Cloning: A Laboratory Manual*, Cold Spring Harbor Laboratory, New York (1989), and in Ausubel et al., *Current Protocols in Molecular Biology*, Greene Publishing Associates and Wiley Interscience, New York (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi M R, Cell 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, Mol. Cell Biol. 7:2745–52 (1987)); electroporation, wherein cells are exposed to large voltage pulses to introduce holes into the membrane (Chu G. et al., Nucleic Acids Res., 15:1311–26 (1987)); lipofection/ liposome fusion, wherein DNA is packaged into lipophilic vesicles which fuse with a target cell (Felgner PL., et al., Proc. Natl. Acad. Sci. USA. 84:7413–7 (1987)); and particle bombardment using DNA bound to small projectiles (Yang N S. et al., Proc. Natl. Acad. Sci. 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T et al., Am. J. Respir. Cell. Mol. Biol., 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding MDK1 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

XVI. Pharmaceutical Formulations and Modes of Administration

The particular compound, antibody, antisense or ribozyme molecule that affects the protein complexes and the disorder of interest can be administered to a patient either by themselves, or in pharmaceutical compositions where it is mixed with suitable carriers or excipient(s).

In treating a patient exhibiting an oncogenic disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics*, 1975, Ch. 1 p. 1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physio logically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The nucleic acid sequence encoding MDK1 can be administered prophylactically, or to patients having a disorder listed above, e.g., by exogenous delivery of the nucleic acid sequence encoding MDK1 as naked DNA, DNA associated with specific carriers, or in a nucleic acid expression vector to a desired tissue by means of an appropriate delivery vehicle, e.g., a liposome, by use of iontophoresis, electroporation and other pharmacologically approved methods of delivery. Routes of administration may include intramuscular, intravenous, aerosol, oral (tablet or pill form), topical, systemic, ocular, as a suppository, intraperitoneal and/or intrathecal.

Some methods of delivery that may be used include:

a. encapsulation in liposomes, b. transduction by retroviral vectors, c. localization to nuclear compartment utilizing nuclear targeting site found on most nuclear proteins, d. transfection of cells ex vivo with subsequent reimplantation or administration of the transfected cells, e. a DNA transporter system.

A MDK1 nucleic acid sequence may be administered utilizing an ex vivo approach whereby cells are removed from an animal, transduced with the MDK1 nucleic acid sequence and reimplanted into the animal. The liver can be accessed by an ex vivo approach by removing hepatocytes from an animal, transducing the hepatocytes in vitro with the MDK1 nucleic acid sequence and reimplanting them into the animal (e.g., as described for rabbits by Chowdhury et al, Science 254: 1802–1805, 1991, or in humans by Wilson, Hum. Gene Ther. 3: 179–222, 1992) incorporated herein by reference.

Many nonviral techniques for the delivery of a MDK1 nucleic acid sequence into a cell can be used, including direct naked DNA uptake (e.g., Wolff et al., Science 247: 1465–1468, 1990), receptor-mediated DNA uptake, e.g., using DNA coupled to asialoorosomucoid which is taken up by the asialoglycoprotein receptor in the liver (Wu and Wu, J. Biol. Chem. 262: 4429–4432, 1987; Wu et al., J. Biol. Chem. 266: 14338–14342, 1991), and liposome-mediated delivery (e.g., Kaneda et al., Expt. Cell Res. 173: 56–69, 1987; Kaneda et al., Science 243: 375–378, 1989; Zhu et al., Science 261: 209–211, 1993). Many of these physical methods can be combined with one another and with viral techniques; enhancement of receptor-mediated DNA uptake can be effected, for example, by combining its use with adenovirus (Curiel et al., Proc. Natl. Acad. Sci. USA 88: 8850–8854, 1991; Cristiano et al., Proc. Natl. Acad. Sci. USA 90: 2122–2126, 1993).

The MDK1 or nucleic acid encoding MDK1 may also be administered via an implanted device that provides a support for growing cells. Thus, the cells may remain in the implanted device and still provide the useful and therapeutic agents of the present invention.

XVII. Identification of Agents

The complexes, components of such complexes, functional equivalents thereof, and/or cell lines that express such components and exhibit such protein complexes may be used to screen for additional compounds, antibodies, or other molecules capable of modulating the signal transduction event such complexes are involved in. Methods for purifying and/or producing such complexes, components of the complexes, functional equivalents thereof, and/or cell lines are described herein. The compounds, antibodies, or other molecules identified may, for example, act to disrupt the protein complexes of the invention (i.e., decrease or inhibit interactions between component members of the complexes, thereby causing physical separation of the components, and/or perturbing the activity of the complexes) or may lower the cellular level and/or decrease the activity of one or more of the components of such complexes.

Such compounds may include, but are not limited to, peptides made of D- and/or L-configuration amino acids (in, for example, the form of random peptide libraries; see Lam et al., *Nature* 354:82–84, 1991), phosphopeptides (in, for example, the form of random or partially degenerate, directed phosphopeptide libraries, see Song-yang et al., *Cell* 767–778, 1993), antibodies, and small organic or inorganic molecules. Synthetic compounds, natural products, and other sources of potentially biologically active materials may be screened in a variety of ways, as described herein. The compounds, antibodies, or other molecules identified may be used as oncogenic disorder treatments, as described herein.

Compounds that bind to individual components, or functional portions of the individual components of the complexes (and may additionally be capable of disrupting complex formation) may be identified.

One such method included within the scope of the invention is a method for identifying an agent to be tested for an ability to modulate a signal transduction pathway disorder. The method involves exposing at least one agent to a protein comprising a functional portion of a member of the protein complex for a time sufficient to allow binding of the agent to the functional portion of the member; removing non-bound agents; and determining the presence of the compound bound to the functional portion of the member of the protein complex, thereby identifying an agent to be tested for an ability to modulate a disorder involving a polypeptide complex.

By "signal transduction disorder" is meant any disease or condition associated with an abnormality in a signal transduction pathway. The protein complex referred to below is a physical association of a MDK1 receptor tyrosine kinase and a MDK1 binding partner. The level of interaction between the two components of the complex may be abnormal and thus cause the abnormality in the signal transduction pathway. Alternatively, the level of interaction between the complex components may be normal, but affecting that interaction may effectively treat a signal transduction pathway disorder.

The term "protein" refers to a compound formed of 5–50 or more amino acids joined together by peptide bonds. An "amino acid" is a subunit that is polymerized to form proteins and there are twenty amino acids that are universally found in proteins. The general formula for an amino acid is $H_2N$—CHR—COOH, in which the R group can be anything from a hydrogen atom (as in the amino acid glycine) to a complex ring (as in the amino acid tryptophan).

A functional portion of an individual component of the complexes may be defined here as a protein portion of an individual component of a complex still capable of forming a stable complex with another member of the complex under standard cellular and physiological conditions. For example, a functional portion of a component may include, but is not limited to, a protein portion of MDK1 which is still capable of stably binding a corresponding binding partner domain of an associated protein, and thus is still capable of forming a complex with that protein. Further, in the case of the catalytic domains of the individual components of the invention, a functional portion of a catalytic domain may refer to a protein still capable of stably binding a substrate molecule under standard physiological conditions.

One method utilizing this approach that may be pursued in the isolation of such complex component-binding molecules would include the attachment of a component molecule, or a functional portion thereof, to a solid matrix, such as agarose or plastic beads, microtiter wells, petri dishes, or membranes composed of, for example, nylon or nitrocellulose, and the subsequent incubation of the attached component molecule in the presence of a potential component-binding compound or compounds. Attachment to said solid support may be direct or by means of a component specific antibody bound directly to the solid support. After incubation, unbound compounds are washed away, component-bound compounds are recovered. By utilizing this procedure, large numbers of types of molecules may be simultaneously screened for complex component-binding activity.

The complex components which may be utilized in the above screening method may include, but are not limited to, molecules or functional portions thereof, such as catalytic domains, phosphorylation domains, extracellular domains, or portions of extracellular domains, such as ligand-binding domains, and adaptor proteins, or functional portions thereof. The peptides used may be phosphorylated, e.g., may contain at least one phosphorylated amino acid residue, preferably a phosphorylated Tyr amino acid residue, or may be unphosphorylated. A phosphorylation domain may be defined as a peptide region that is specifically phosphorylated at certain amino acid residues. A functional portion of such a phosphorylation domain may be defined as a peptide capable of being specifically phosphorylated at certain amino acids by a specific protein.

Molecules exhibiting binding activity may be further screened for an ability to disrupt protein complexes. Alternatively, molecules may be directly screened for an ability to promote the complexes. For example, in vitro complex formation may be assayed by, first, immobilizing one component, or a functional portion thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound. In addition, one could look for an increase in binding.

Additionally, complex formation in a whole cell may be assayed by utilizing co-immunoprecipitation techniques well known to those of skill in the art. Briefly, a cell line capable of forming a complex of interest may be exposed to a compound such as one identified as above, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

A preferred method for assessing modulation of complex formation within a cell utilizes a method similar to that described above. Briefly, a cell line capable of forming a complex of interest is exposed to a test compound. The cells are lysed and the lysate contacted with an antibody specific to one component of the complex, said antibody having been previously bound to a solid support. Unbound material is washed away, and the bound material is exposed to a second antibody, said second antibody binding specifically to a second component of the complex. The amount of second antibody bound is easily detected by techniques well known in the art. Cells exposed to an inhibitory test compound will have formed a lesser amount of complex compared to cells not exposed to the test compound, as measured by the amount of second antibody bound. Cells exposed to a test compound that promotes complex formation will have an increased amount of second antibody bound.

The effect of an agent on the differentiation capability of the complex of interest may be directly assayed. Such agents may, but are not required to, include those agents identified by utilizing the above screening technique. For example, an agent or agents may be administered to a cell such as a neuronal cell, capable of forming a complex, for example, which, in the absence of any agent, would not lead to the cell's differentiation. The differentiation state of the cell may then be measured either in vitro or in vivo. One method of measurement may involve observing the amount of neurile growth present.

Agents capable of disrupting complex formation and capable of reducing or inhibiting disorders, which involve the formation of such complexes, or which involve the lack of formation of such complexes, may be used in the treatment of patients exhibiting or at risk for such disorders. A sufficient amount of agent or agents such as those described above may be administered to a patient so that the symptoms of the disease or condition are reduced or eliminated.

XVIII. Purification and Production of Complexes

Described in this Section are methods for the synthesis or recombinant expression of components, or fragments thereof, of the protein complexes of the invention. Also described herein are methods by which cells exhibiting the protein complexes of the invention may be engineered.

XIX. Purification Methods

The complexes of the invention may be substantially purified, i.e., may be purified away from at least 90% (on a weight basis), and from at least 99%, if desired, of other proteins, glycoproteins, and other macromolecules with which it is associated. Such purification can be achieved by utilizing a variety of procedures well known to those of skill in the art, such as subjecting cells, tissue or fluid containing the complex to a combination of standard methods, for example, ammonium sulfate precipitation, molecular sieve chromatography, and/or ion exchange chromatography.

Alternatively, or additionally, a complex may be purified by immunoaffinity chromatography using an immunoadsorbent column to which an antibody is immobilized which is capable of binding to one or more components of the complex. Such an antibody may be monoclonal or polyclonal in origin. Other useful types of affinity purification for the protein complex may utilize, for example, a solid-phase substrate which binds the catalytic kinase domain of a protein, or an immobilized binding site for noncatalytic domains of the components of the complex, which bind in such a manner as to not disrupt the complex. The complex of the present invention may be biochemically purified from a variety of cell or tissue sources.

XX. Synthesis and Expression Methods

Methods for the synthesis of polypeptides or fragments thereof, which are capable of acting as components of the complexes of the present invention, are well-known to those of ordinary skill in the art. See, for example, Creighton, *Proteins: Structures and Molecular Principles*, W.H. Freeman and Co., New York (1983), which is incorporated herein, by reference, in its entirety.

Components of a complex which have been separately synthesized or recombinantly produced, may be reconstituted to form a complex by standard biochemical techniques well known to those skilled in the art. For example, samples containing the components of the complex may be combined in a solution buffered with greater than about 150 mM NaCl, at a physiological pH in the range of 7, at room temperature. For example, a buffer comprising 20 mM Tris-HCl, pH 7.4, 137 mM NaCl, 10% glycerol, 1% Triton X-100, 0.1% SDS, 0.5% deoxycholate and 2 mM EDTA could be used.

Methods for preparing the components of complexes of the invention by expressing nucleic acid encoding proteins are described herein. Methods which are well known to those skilled in the art can be used to construct expression vectors containing protein coding sequences and appropriate transcriptional and translational control signals. These methods include, for example, in vitro recombinant DNA techniques, synthetic techniques and in vivo recombination/genetic recombination. DNA and RNA synthesis may, additionally, be performed using an automated synthesizers. See, for example, the techniques described in Maniatis et al., *Molecular Cloning: A Laboratory Manual*, Cold Spring Harbor Laboratory, New York (1989), and in Ausubel et al., *Current Protocols in Molecular Biology*, Greene Publishing Associates and Wiley Interscience, New York (1989).

A variety of host-expression vector systems may be utilized to express the coding sequences of the components of the complexes of the invention. Such host-expression systems represent vehicles by which the coding sequences of interest may be produced, but also represent cells which may, when transformed or transfected with the appropriate nucleotide coding sequences, exhibit the protein complexes of the invention. These include but are not limited to microorganisms such as bacteria (e.g., *E. coli, B. subtilis*) transformed with recombinant bacteriophage DNA, plasmid DNA or cosmid DNA expression vectors containing protein coding sequences; yeast (e.g., Saccharomyces and Pichia) transformed with recombinant yeast expression vectors containing the protein coding sequences; insect cell systems infected with recombinant virus expression vectors (e.g., *baculovirus*) containing the protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems a number of expression vectors may be advantageously selected depending upon the use intended for the complex being expressed. For example, when large quantities of complex proteins are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., *EMBO J.* 2:1791, 1983), in which the protein coding sequence may be ligated individually into the vector in frame with the lac Z coding region so that a fusion protein is produced; pIN vectors (Inouye and Inouye, *Nucleic acids Res.* 13:3101–3109, 1985; Van Heeke & Schuster, *J. Biol. Chem.* 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned protein can be released from the GST moiety.

In an insect system, *Autographa californica* nuclear polyhedrosis virus (AcNPV) is used as a vector to express foreign genes. The virus grows in *Spodoptera frugiperda* cells. The complex coding sequence may be cloned individually into non-essential regions (for example the polyhedrin gene) of the virus and placed under control of an AcNPV promoter (for example the polyhedrin promoter). Successful insertion of the PTK/adaptor complex coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., *J. Biol.* 46:584, 1983; Smith, U.S. Pat. No. 4,215,051).

In mammalian host cells, a number of viral based expression systems may be utilized. In cases where an adenovirus is used as an expression vector, the complex coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts. (E.g., See Logan & Shenk, *Proc. Natl. Acad. Sci. USA* 81:3655–3659, 1984) Specific initiation signals may also be required for efficient translation of inserted coding sequences. These signals include the ATG initiation codon and adjacent sequences.

In cases where an entire protein gene, including its own initiation codon and adjacent sequences, is inserted into the appropriate expression vector, no additional translational control signals may be needed. However, in cases where only a portion of the coding sequence is inserted, exogenous translational control signals, including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987)

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably coexpress both the proteins may be engineered. Rather than using expression vectors which contain viral origins of replication, host cells can be transformed with the protein encoding DNA independently or coordinately controlled by appropriate expression control elements (e.g., promoter, enhancer, sequences, transcription terminators, polyadenylation sites, etc.), and a selectable marker.

Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the PTK and adaptor protein. Such engineered cell lines are particularly useful in screening and evaluation of compounds that affect signals mediated by the complexes.

A number of selection systems may be used, including but not limited to the herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:2026, 1962), and adenine phosphoribosyltransferase (Lowy et al., *Cell* 22:817, 1980) genes can be employed in tk⁻, hgprt⁻ or aprt⁻ cells, respectively. Also, antimetabolite resistance can be used as the basis of selection for dhfr, which confers resistance to methotrexate (Wigler et al., *Natl. Acad. Sci. USA* 77:3567, 1980; O'Hare et al., *Proc. Natl. Acad. Sci. USA* 78:1527, 1981); gpt, which confers resistance to mycophenolic acid (Mulligan & Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al. *Gene* 30:147, 1984) genes.

New members of the protein families capable of forming the complexes of the invention may be identified and isolated by molecular biological techniques well known in the art. For example, a previously unknown protein encoding gene may be isolated by performing a polymerase chain reaction (PCR) using two degenerate oligonucleotide primer pools designed on the basis of highly conserved sequences within domains common to members of the protein family. The template for the reaction may be cDNA obtained by reverse transcription of mRNA prepared from cell lines or tissue known to express complexes. The PCR product may be subcloned and sequenced to insure that the amplified sequences represent the sequences of a member of the PTK or adaptor subfamily. The PCR fragment may then be used to isolate a full length protein cDNA clone by radioactively labeling the amplified fragment and screening a bacteriophage cDNA library. Alternatively, the labeled fragment may be used to screen a genomic library. For a review of cloning strategies which may be used. See e.g., Maniatis, *Molecular Cloning: A Laboratory Manual*, Cold Springs Harbor Press, New York (1989); and Ausubel et al., *Current Protocols in Molecular Biology*, Green Publishing Associates and Wiley Interscience, New York (1989). A general method for cloning previously unknown proteins has been described by Skolnik (Skolnik, E. Y., *Cell* 65:75, 1991) and Skolnik et al., (U.S. patent application Ser. No. 07/643,237) which are incorporated herein by reference, in their entirety, including drawings.

XXI. Derivatives of Complexes

Also provided herein are functional derivatives of a complex. By "functional derivative" is meant a "chemical derivative," "fragment," "variant," "chimera," or "hybrid" of the complex, which terms are defined below. A functional derivative retains at least a portion of the function of the protein, for example reactivity with an antibody specific for the complex, enzymatic activity or binding activity mediated through noncatalytic domains, which permits its utility in accordance with the present invention.

A "chemical derivative" of the complex contains additional chemical moieties not normally a part of the protein. Covalent modifications of the protein complex or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro erivatives, respectively.

Carboxyl side groups (aspartyl or glutamyl) are electively modified by reaction carbodiimide (R'—N=C=N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are onverted to asparaginyl and glutaminyl residues by eaction with ammonium ions.

Glutaminyl and asparaginyl residues are freuently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the complexes to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[p-azidophenyl]dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W.H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in *Remington's Pharmaceutical Sciences,* 18th ed., Mack Publishing Co., Easton, Pa. (1990).

The term "fragment" is used to indicate a polypeptide derived from the amino acid sequence of the proteins, of the complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence. Fragments of a protein, when present in a complex resembling the naturally occurring complex, are useful for screening for compounds that act to modulate signal transduction, as described below. It is understood that such fragments, when present in a complex may retain one or more characterizing portions of the native complex. Examples of such retained characteristics include: catalytic activity; substrate specificity; interaction with other molecules in the intact cell; regulatory functions; or binding with an antibody specific for the native complex, or an epitope thereof.

Another functional derivative intended to be within the scope of the present invention is a complex comprising at least one "variant" polypeptide which either lack one or more amino acids or contain additional or substituted amino acids relative to the native polypeptide. The variant may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native complex, as described above.

A functional derivative of complexes comprising proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art. The functional derivatives of the complexes typically exhibit the same qualitative biological activity as the native complexes.

Other functional derivatives include mutant, species and allelic variations.

By "mutant variation" is meant a nucleic acid or amino acid molecule that results from any detectable change in the genetic material which may be transmitted to daughter cells giving rise to mutant cells, including nucleic acids or polypeptides having nucleotides or amino acids that are added, deleted, substituted for, inverted, or transposed to new positions with and without inversion. The mutant variation may occur spontaneously or may be induced experimentally by application of mutagens and may result from any (or a combination of) detectable, unnatural change affecting the chemical or physical constitution, mutability, replication, phenotypic function, or recombination of one or more deoxyribonucleotides.

By "species variation" is meant a change in the nucleic acid or amino acid sequence that occurs among species and may be determined by DNA sequencing of the molecule in question.

By "allelic variation" is meant an alternative functional derivation of the typical form of a gene in an organism occupying a given locus on a chromosome.

XXII. Evaluation of Disorders

The protein complexes of the invention involved in disorders may be utilized in developing a prognostic evaluation of the condition of a patient suspected of exhibiting such a disorder. For example, biological samples obtained from patients suspected of exhibiting a disorder involving a protein complex may be assayed for the presence of such complexes. If such a protein complex is normally present, and the development of the disorder is caused by an abnormal quantity of the complex, the assay should compare complex levels in the biological sample to the range expected in normal tissue of the same cell type.

Among the assays which may be undertaken may include, but are not limited to isolation of the protein complex of interest from the biological sample, or assaying for the presence of the complex by exposing the sample to an antibody specific for the complex, but non-reactive to any single, non-complexed component, and detecting whether antibody has specifically bound.

Alternatively, one or more of the components of the protein complex may be present in an abnormal level or in a modified form, relative to the level or form expected is normal, nononcogenic tissue of the same cell type. It is possible that overexpression of both components may indicate a particularly aggressive disorder. Thus, an assessment of the individual and levels of mRNA and protein in diseased tissue cells may provide valuable clues as to the course of action to be undertaken in treatment of such a disorder. Assays of this type are well known to those of skill in the art, and may include, but are not limited to, Northern blot analysis, RNAse protection assays, and PCR for determining mRNA levels. Assays determining protein levels are also well known to those of skill in the art, and may include, but are not limited to, Western blot analysis, immunoprecipitation, and ELISA analysis. Each of these techniques may also reveal potential differences in the form (e.g., the primary, secondary, or tertiary amino acid sequence, and/or post-translational modifications of the sequence) of the component(s).

EXAMPLES

The examples below are non-limiting and are merely representative of various aspects and features of the present invention. The examples below demonstrate the isolation of MDK1, analysis of MDK1 Northern blots, analysis of MDK1 by in situ hybridization, and expression of MDK1 in human 293 fibroblasts.

cDNA Cloning of MDK1

PCR reactions were performed on cDNA prepared with poly(A$^+$) RNA from 13.5 day old mouse embryos using degenerate oligonucleotide primers according to Lai and Lemke (Lai and Lemke, *Neuron* 6:691–704, 1991). These primers correspond to the conserved peptide motifs HRD-LAA (SEQ. I.D. NO. 9) and D(V/M)WS(F/Y)G (SEQ. I.D. NO. 10) of the kinase catalytic domain. One of the isolated PCR fragments coding for 68 amino acids of the catalytic domain of MDK1 was subsequently used in cDNA library screening of a mouse embryo cDNA library (11.5 day embryo, Clontech) and a mouse adult brain library (Clontech).

DNA sequencing was performed according to the dideoxynucleotide chain termination method (Sanger et al., *Proc. Natl. Acad. Sci. USA* 74:5463–5467, 1977) using sequenase enzyme, reagents and protocols supplied by United States Biochemical Corporation. Ambiguous sequences were sequenced using the dITP extension of the sequenase sequencing kit. Comparisons of inferred MDK1 protein sequence with various sequence databases were done using the TFASTA program (Pearson and Lipman, *Proc. Natl. Acad. Sci. USA* 85:2444–2448, 1988) provided with the GCG sequence analysis software package (Genetics Computer Group, Wisconsin).

RNA Extraction and Northern Analysis

Balb/c mice were mated overnight and the morning of vaginal plug detection was defined as 0.5 day of gestation. For Northern blot analysis, RNA was extracted from the frozen embryos according to the acidic phenol method of Chomczynski and Sacchi (Chomczynski and Sacchi, *Analytical Biochemistry* 162:156–159, 1987). Oligo(dT)column chromatography was used for the selection of poly(A$^+$) RNA. Aliquots were electrophoresed in 1.2% agarose formaldehyde (Sambrook et al., *Molecular cloning—A Laboratory Manual.* 2nd ed., Cold Spring Harbor Laboratory Press, New York, 1989) gels and transferred to nitrocellulose membranes. Hybridizations were performed overnight in 50% formamide, 5×SSC (750 mM sodium chloride, 75 mM sodium citrate), 5×Denhardt's (0.1% Ficoll 400, 0.1% polyvinylpyrollidone, 0.1% BSA) and 50 mM NaPO$_4$ (pH6.8) at 42° C. with 1–3×10$^6$ cpm/ml of $^{32}$P-random primed DNA probe, followed by high stringency washes in 0.2×SSC, 0.2% SDS at 50° C. The filters were exposed for 14 days. For repeated use, filters were stripped of any labeled DNA by incubation in destillated water at 95° C. for 10 minutes.

Preparation of Antisera

The C-terminal 110 amino acids of MDK1 were subcloned into the fusion protein expression vector pGEX1 (Smith and Johnson, *Gene* 67:31–40, 1988; Pharmacia). The fusion protein was purified as described and used for immunizing rabbits.

Transient Expression of MDK1 in 293 Cells

Transfection of human embryonic kidney fibroblast 293 cells (ATCC CRL 1573) was performed as described by Chen and Okayama (Chen and Okayama, *Mol. Cell. Biol.* 7:2745–2752, 1987). The cDNA encoding MDK1, MDK1Δ1 or MDK1Δ2 was subcloned into an expression vector under the control of the immediate early cytomegalovirus promoter. CsCl-purified DNA was used for transfections. Treatment and lysis of the cells were performed as described by Lammers et al. (Lammers et al., *J. Biol. Chem.* 268:22456–22462, 1993).

For immunoprecipitations, Protein-A sepharose and either 2 μl of the antiserum against the C-term of MDK1 or 5 μg of the mouse monoclonal anti-phosphotyrosine antibody 5E.2 (Fendly et al., *Cancer Research* 50:1550–1558, 1990) were added to the cell lysate and incubated at 4° C. for 3 hours. The immunoprecipitates were washed with HNTG buffer (20 mM HEPES, pH 7.5, 150 mM NaCl, 10% glycerol, 0.1% Triton X-100, 10 mM NaF, 1 mM sodium orthovanadate), separated on a 7.5% SDS polyacrylamide gel, dried on a vacuum dryer and exposed for 1 day. For deglycosylation of MDK1, the immunoprecipitated proteins were denatured in Denaturing Buffer and incubated with 1,000 units of PNGase F according to the manufacturer's instructions (New England Biolabs).

Preparation of Probes

For Northern blot hybridization, the indicated fragments were isolated and prepared by labeling with α-($^{32}$P)dATP (Amersham) by random hexanucleotide priming (USB, Feinberg and Vogelstein, *Anal. Biochem.* 132:6–13, 1983). A 5'-located 1,565 bp fragment corresponding to amino acids 18 to 538 (nucleotides 282 to 1,847) of the extracellular domain of MDK1 was subcloned into the pBluescript vector (Stratagene) for use as a probe for the in situ hybridization. Single-stranded DNA probes were prepared as described previously (Millauer et al., *Cell* 72:835–846, 1993). Briefly, RNA transcripts were synthesized from the linearized plasmid using T3- or T7 RNA-Polymerase (Boehringer) and the DNA was degraded using DNase (RNase-free preparation, Boehringer). The RNA transcripts were used for a random-primed cDNA synthesis with α-($^{35}$S)dATP (Amersham) by reverse transcription with MMLV reverse transcriptase (BRL), giving small cDNA transcripts of about 100 bp. After hydrolyzation of the RNA the probe was purified with a sephadex-G50 column.

In situ Hybridization

For in situ hybridization, the embryos or the isolated brain of 8-week-old female mice were embedded in Tissue-Tek (Miles), frozen on the surface of liquid nitrogen and stored at −70° C. prior to use. Sectioning, postfixation and hybridization was performed as described previously (Millauer et al., *Cell* 72:835–846, 1993). 10 μm-thick sections were incubated overnight with the $^{35}$S-cDNA probe (final concentration 2×10$^4$ cpm/μl) at 52° C. in a buffer containing 50% formamide, 300 mM NaCl, 10 mM Tris-HCl, 10 mM NaPO$_4$ (pH6.8), 5 mM EDTA, 0.02% Ficoll 400, 0.02% polyvinylpyrolidone, 0.02% BSA, 10 mg/ml yeast RNA, 10% dextran sulfate, and 10 mM DTT. Posthybridization washing was performed at high stringency (50% formamide, 300 mM NaCl, 10 mM Tris-HCl, 10 mM NaPO$_4$ (pH6.8), 5 mM EDTA, 10 mM DTT at 52° C.). Slides were coated with Kodak NTB2 film emulsion and exposed for seven days. After developing, the sections were counterstained with toluidine blue. All sections were analyzed with an Olympus BH2 or SZ-PT microscope using brightfield and darkfield illumination.

Example 1

Isolation of MDK1

Using a PCR-based approach (Wilks et al., *Gene* 85:67–74, 1989; Lai and Lemke, *Neuron* 6:691–704, 1991) with degenerate oligonucleotide primers specific for conserved motifs of receptor tyrosine kinases, we attempted to identify new RTKs displaying developmental regulation. Out of approximately 600 clones obtained through PCR on cDNA from mouse embryos of the stages 9.5 p.c., 11.5 p.c., 13.5 p.c., 15.5 p.c., 17.5 p.c., and 19.5 p.c., we identified three short cDNA sequences coding for subdomains VI to IX of the kinase domain (Hanks et al., 1988) of previously unidentified RTKs.

Using the PCR-amplified MDK1 fragment for screening of an 11.5 day mouse embryo and an adult mouse brain cDNA library, we isolated fifteen independent phage clones, which were sequenced completely. Six clones proved to include the full-length sequence of MDK1. The nucleotide and inferred amino acid sequence is shown in FIG. 1, in which the predicted initiating methionine and the signal peptide according to Kozak (Kozak, M., *Nucleic Acids Res.* 12:857–872, 1984) and Heijne (Heijne, G. v., *Nucleic Acids Res.* 14:4683–4690, 1986) are indicated.

MDK1 is a member of the eck/eph family of RTKs, as evidenced by the complete conservation of cysteine residues in the ectodomain and the presence of tandem fibronectin type III (FN III) homology domains (FIG. 1; Pasquale, E. B., *Cell Regula.* 2:523–534, 1991). Comparison of the ectodomain sequences revealed 61% amino acid identity of MDK1 to Ehk-1 and 59% to Mek4 and Sek, but only 41% to Eph. Comparison of the intracellular domains revealed 76% amino acid identity of MDK1 to Ehk-2, 75% to Sek, and 55% to Eph.

One clone was found to contain an alternative 3'-untranslated region. In this clone, the polyadenylation signal appeared to be bypassed, resulting in a longer MDK1 transcript (FIG. 1). Four sequence variants of MDK1 were identified: three independent clones each were identified encoding most of the open reading frame of MDK1 but lacking five (MDK1Δ1) or four (MDK1Δ2) amino acids (SEQ ID Nos: 11 and 12, respectively) (see FIG. 2C). In MDK1Δ2, the codon of one amino acid 5' of the missing nucleotide stretch was changed, resulting in an amino acid alteration from phenylalanine to cysteine.

In addition, we isolated two clones encoding different truncated forms of MDK1, designated MDK1.T1 and MDK1.T2 (SEQ ID Nos: 3 and 5, respectively) (FIGS. 2A and 2B), whose deduced amino acid sequences comprised the extracellular and transmembrane domains of MDK1 but contained only twenty amino acids of the MDK1 juxtamembrane domain. Their C-termini end with eleven (MDK1.T1) or twenty-seven (MDK1.T2) unique amino acids. MDK1.T1, MDK1.T2, and MDK1Δ2 exhibit a variation of the MDK1 sequence at the same nucleotide position (base 2031), indicating the location of an exon/intron border. A schematic representation of the various forms of MDK1 found by screening the mouse adult brain cDNA library is shown in FIG. 2C.

Example 2

Northern Blot Analysis

Northern blot analysis was performed with different nucleotide probes of the MDK1 and MDK1.T1 cDNA. 4 μg of poly(A$^+$) RNA isolated from 13.5 day mouse embryos were analyzed. Sizes were determined by using the residual 28S and 18S ribosomal RNAs as internal markers and are indicated by arrowheads. The probes used correspond to nucleotides 282–1847 (A), 1847–2082 (B), 2029–2900 (C) and 3758–4304 (D) of MDK1 (as set forth in SEQ ID NO: 1) and nucleotides 2044–2666 (E) of MDK1.T1 (as set forth in SEQ ID NO: 3). Using the extracellular domain of MDK1 as a probe, we identified five transcripts of 6.8, 5.7, 4.0, 3.2, and 2.6 kb in poly(A$^+$) RNA from mouse embryo day 13.5 p.c. The two smallest transcripts were also detected with a probe corresponding to the transmembrane domain, but not with a probe corresponding to the intracellular domain of MDK1, confirming the existence of transcripts encoding variant forms of MDK1 lacking the intracellular kinase domain found by the cDNA library screening. The 3.2 kb transcript corresponds to MDK1.T1, whereas the lowest band probably corresponds to MDK1.T2, since the size of 2.6 kb matches that of the cDNA of MDK1.T2. The upper three bands of 6.8, 5.7, and 4.0 kb are predicted to encode the full-length MDK1 forms, with the 6.8 kb and 5.7 kb transcripts resulting from the use of an alternative polyadenylation site.

To elucidate the developmental regulation of MDK1 transcription during mouse embryology, we performed Northern blot analysis of poly(A$^+$) RNA isolated from embryonic and postnatal stages E10.5 to E18.5 and P1 to P8, respectively.

Northern blot analysis of MDK1 expression throughout mouse development was performed. 4 μg poly(A$^+$) RNA of mouse embryos day 12.5 to 18.5 and of the four postnatal stages day 1, 2, 4 and 8 were fractionated on an 1.2% agarose gel, blotted on nitrocellulose and hybridized with a MDK1 cDNA probe corresponding to bp 282–1,847 (probe A). The positions of the 28S and 18S ribosomal RNA were marked, the mRNA sizes were deduced. Rehybridization of the same blot with a glyceraldehyde-3-phosphate dehydrogenase (GAPDH) probe (Dugaczyk et al., *Biochemistry*, 22:1605–1611, 1983), indicated loading of equal amounts of mRNA.

Northern blot analysis of MDK1 expression in adult mouse tissues was also performed. 10 μg total RNA of the indicated tissues were separated and hybridized with the same probe as above. The origins of the RNAs are as follows: adult stomach, brain, testes, heart, lung, liver, kidney, spleen and muscle. The gel was stained with ethidium bromide before blotting to allow for comparison of equal RNA loading.

MDK1 transcripts were readily detectable as early as embryonic day 10.5. The signal intensity observed for the full-length MDK1 transcripts declined during development and was barely detectable in the postnatal day 8 mouse. The intensity of the transcripts corresponding to the truncated forms of MDK1 remained unchanged.

In adult mouse tissues, MDK1 transcripts were detected in brain and testes and, at lesser intensity, in spleen. In brain, we identified all five MDK1 transcripts with a prominent signal corresponding to MDK1.T1; testes and spleen, however, showed a transcript size of 3.5 kb, indicating the existence of an additional transcript variant with tissue-specific expression.

Example 3

MDK Expression Analysis by In situ Hybridization

To investigate the temporal expression of MDK1 during murine development, we used a MDK1-specific, single-stranded antisense probe corresponding to the extracellular domain (nucleotides 282 to 1,847 of the MDK1 sequence), which recognizes all of the different forms of MDK1. Sagittal and horizontal sections of 12.5, 14.5, 16.5, and 18.5 day embryo and of the adult mouse brain were examined. MDK1 expression was detected in a variety of neuronal tissues and appeared to be very complex.

MDK1 expression in 12.5 p.c. and 14.5 p.c. embryos was studied. In situ hybridization was studied using a ($^{35}$S)-dATP labelled cDNA antisense construct corresponding to the extracellular domain of MDK1 on sagittal and horizontal sections of mouse embryos. Dark-field views of sagittal sections of a 12.5 p.c. and a 14.5 p.c. embryo were obtained. Sections hybridized with the antisense probe, and control hybridization used the sense strand. Dark-field view of a horizontal section of a 12.5 p.c. embryo showed the high expression of MDK1 in the most dorsal part of the epithalamus. Higher magnification of the MDK1 expression in the mesenchyme surrounding the dorsal root ganglia was also studied. Dark-field view of a sagittal section of a 14.5 p.c. embryo showed MDK1 expression in the neuroepithel of the cochlea. Sections that hybridized with the antisense probe include: trigeminal (V) ganglion; inferior olive; lung; dorsal root ganglia.

MDK1 expression in the 16.5 p.c. mouse embryo was also studied. Dark-field and light-field view of sections of a 16.5 p.c. mouse embryo. All sections were hybridized with the MDK1 antisense probe except for a control hybridization. Sagittal section of the head of the embryo and the mouth and the kidney were obtained. MDK1 expression in the superior colliculus (sagittal section) and the subcommisural organ (horizontal section) were observed. Dark-field and light-field views of the trigeminal ganglion were taken. Dark-field and light-field view of a sagittal section through a hindlimb were also taken.

MDK1 expression in the 18.5 p.c. embryo and in the adult central nervous system was also studied. Dark-field view of sections of an 18.5 p.c. embryo and adult brain. Sagittal sections hybridized with the antisense or the sense probe of MDK1. Horizontal section hybridized with the antisense probe showing expression in the inferior olive. Sagittal sections probed for MDK1 expression showing strong transcription in the habenula of the epithalamus and in the mammillary body and the pons. Antisense and control hybridization on a sagittal section of the adult brain. MDK1 expression in the cerebellum was studied. We noted limited expression of MDK1 in the Purkinje cell layer. Horizontal section of the adult brain hybridized with the antisense probe for MDK1. A higher magnification of the subcommisural organ was also observed.

In the central nervous system (CNS), expression of MDK1 persisted during the developmental stages analyzed in the epithalamus, the thalamus, the mammillary body of the hypothalamus, in the developing hippocampus, in the dentate gyrus, and at a low level in the caudate-putamen. MDK1 transcripts were detected throughout the development of the cerebellum, with transcripts in the alar plate of the metencephalon of the 12.5 day embryo and in the cerebellar primordium of the 14.5 day embryo. MDK1 was also found in the tectum, in later stages of development restricted to the superior colliculus. In addition, we observed expression in the frontal and cingulate cortex of the 12.5 day embryo and, starting at 16.5 p.c., in the neopallial cortex and in the ventricular zone of the telencephalon. The embryonic stage E18.5 also displayed MDK1 transcripts in the pyriform cortex. MDK1 expression was found in the pons and the medulla, with a strong signal in the inferior olive. Starting at embryonic stage E14.5, the subcommisural organ appeared as a site of strong MDK1 expression. Additional signals were detected in the striatum of the ganglionic eminence and in the septal nucleus of the 16.5 p.c. embryo.

The adult brain displayed a more restricted pattern of MDK1 transcription. Although there appeared to be a very faint expression of MDK1 in the whole brain, a slightly higher transcription rate was detected in the nucleus caudatus-putamen and in the cortex, especially in the granular cortex and the pyriform cortex. Regions of higher MDK1 expression include the habenula, the mammillary nucleus, the anterior olfactory nucleus and the Purkinje cell layer of the cerebellum. In addition, MDK1 was strongly expressed in the pyramidal cell layer of the hippocampus (CA1, CA2, CA3) as well as in the neurons of the dentate gyrus and in the subcommisural organ. These areas of strong MDK1 expression in the adult brain were detected in all stages of the CNS development.

In the peripheral nervous system, high levels of MDK1 expression were maintained in the trigeminal (V) ganglion and the vestibulocochlear (VIII) ganglion. MDK1 transcripts were abundant in the neuroepithelium of the cochlea.

Particularly in early stages of murine development, MDK1 displayed a variety of expression sites outside the nervous system, which decreased in later stages of development both in intensity and diversity. MDK1 transcripts were found in the kidney and lung, and were restricted to glomeruli and the central mesenchyme, and the segmental bronchi, terminal bronchi and bronchioles, respectively. Strong expression of MDK1 in the limb buds appeared to be restricted to the blastema condensations and the cartilage primordia of the limb buds and, at embryonic day 16.5, to the connective tissue surrounding the joints between the metacarpal or the metatarsal and the phalanges bones. Prominent areas of MDK1 transcription were found in the developing lips, the eyelids, and the tongue, and to a lesser degree in the heart and in the epithelial lining of the liver.

At embryonic stage E12.5, a very strong signal was identified in mesenchymal cells surrounding the spinal cord and the brain, which was reduced through development and undetectable at embryonic day 18.5. We also observed strong expression of MDK1 in the primitive nasal cavity and the nasal septum, in the lateral palatine process and in the maxillary process, and, in addition, a weak signal in the precartilage primordium of the ribs of the 12.5 p.c. embryo. Later in development, new expression sites found in the 14.5 day embryo included the primordia of follicules of fibrissae and the primordia of the incisor and the molar teeth, with low levels of transcription detected in the intestine, at the pinna of the ear, and in the mesenchyme of the nasal capsule and around the oesophagus and the trachea. The embryonic day 16.5 exhibited MDK1 expression in different glands, including the submandibular gland, the mucous palatine glands, the serous glands of the nasal septum and, in the 18.5 day embryo, in the parotid gland. At this stage, there was no expression of MDK1 in the heart, intestine or in the epithelial lining of the liver, a reduced expression level in the lung and the tongue, and predominant expression in the brain.

Example 4

Expression of MDK1 in Human 293 Fibroblasts

To investigate the tyrosine kinase activity of MDK1, we used the human 293 cell transient expression system (Lammers et al., *J. Biol. Chem.* 268:22456–22462, 1993). The different cDNAs were subcloned into a cytomegalovirus promoter-based expression vector and transfected into subconfluent 293 monolayers. Subsequently, the proteins were labelled metabolically by incubating the cells with [$^{35}$S] methionine.

Immunoprecipitation of ($^{35}$S) methionine-labeled MDK1 from 293 cells was performed. 293 cells transiently transfected with MDK1, MDK1Δ1 and MDK1Δ2 expression plasmids were labeled metabolically overnight with ($^{35}$S) methionine. The cells were lysed and the proteins were immunoprecipitated with the indicated antibodies. Separation of the immunoprecipitated proteins was done by SDS-PAGE. Autoradiographs of the gels were obtained and the molecular weights in kDa of the markers were determined. Untransfected 293 cells were used as a control.

Immunoprecipitation with antiserum directed against the C-term of MDK1 was performed. The MDK1 variants were immunoprecipitated as above but treated with 1,000 units of PNGase F prior SDS-PAGE as indicated to remove all asparagine linked carbohydrates. The untreated MDK1 protein was an additional control. Immunoprecipitation with anti-phosphotyrosine antibody 5E.2. was also performed. Cells were treated with 1 mM sodium orthovanadate (NaOVan) to inhibit cellular protein tyrosine phosphatases (+) for 90 min before lysis.

The receptor variants MDK1, MDK1Δ1, and MDK1Δ2 were immunoprecipitated using a polyclonal antibody directed against the carboxy-terminal 110 amino acids of MDK1. Autoradiography of the protein gel shows a doublet of apparent molecular weight of 120 kD and 114 kD. PNGase F treatment and removal of asparagine-linked carbohydrates from immunoprecipitated, [$^{35}$S]methionine-labelled MDK1 indicated that the 120 kD band corresponded to the glycosylated MDK1, which has a calculated molecular weight of 112 kD.

To investigate the ability of MDK1 to autophosphorylate, we treated cells that had been transfected with appropriate vector constructs for 90 min with 1 mM sodium orthovanadate prior to lysis. The [$^{35}$S]methionine-labelled proteins were immunoprecipitated with the antiphosphotyrosine antibody 5E.2 and resolved by SDS-PAGE. The resulting autoradiograph shows a protein doublet of the expected size, indicating strong MDK1 autophosphorylation. Several less intense additional phosphotyrosine-containing protein bands in the immunoprecipitates of sodium orthovanadate-treated cells may be cellular substrates of MDK1 because they could not be identified in untransfected 293 cells.

The identity of the strongly labeled protein band of approximately 47 kD is not clear. This protein was not observed in untransfected cells, and immunoprecipitations of MDK1 from mixed cell lysates of unlabelled cells transfected with MDK1 with [$^{35}$S]methionine-labelled, untransfected control cells demonstrated that this protein was not a coimmunoprecipitated substrate of MDK1. Since its apparent molecular size corresponds to the calculated molecular size of the entire intracellular domain of MDK1 (47 kD), we considered the possibility of the existence of a soluble catalytic kinase domain, either as a specific degradation product or as part of a signal transduction mechanism. Since this band was also detected after solubilizing the cells with hot Laemmli buffer, we can exclude the possibility that it was generated during the experimental procedure.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An isolated, enriched or purified nucleic acid molecule:

(a) encoding a MDK1 polypeptide comprising the amino acid sequence set forth in SEQ ID NO: 2; or (b) a nucleic acid molecule that is completely complementary to the nucleic acid molecule of (a).

2. A recombinant nucleic acid molecule, comprising:

(a) a nucleic acid sequence that, when transcribed, produces a transcript encoding a MDK1 polypeptide comprising the amino acid sequence set forth in SEQ ID NO: 2; or (b) a nucleic acid molecule that is completely complementary to the nucleic acid molecule of (a); and a vector or a promoter effective to initiate transcription in a host cell.

3. A recombinant nucleic acid molecule, comprising:
a transcriptional region functional in a cell comprising a nucleic acid sequence that, when transcribed, produces a transcript
  (a) encoding a MDK1 polypeptide comprising the amino acid sequence set forth in SEQ ID NO: 2; or
  (b) a nucleic acid molecule that is completely complementary to the nucleic acid molecule of (a); and
a translational termination region functional in a cell.

4. The isolated, enriched, or purified nucleic acid of claim 1 comprising the nucleic acid sequence set forth in SEQ ID NO: 1.

5. An isolated, enriched, or purified nucleic acid molecule:
  (a) encoding MDK1.Δ1 set forth in SEQ ID NO:11; or MDK1.Δ2 set forth in SEQ ID NO:12; or
  (b) a nucleic acid molecule that is completely complementary to the nucleic acid molecule of (a).

6. An isolated, enriched, or purified nucleic acid molecule:
  (a) encoding a MDK1 polypeptide comprising the intracellular domain as set forth by amino acids 580 to 998 of SEQ ID NO: 2; or
  (b) a nucleic acid molecule that is completely complementary to the nucleic acid molecule of (a).

7. An isolated, enriched, or purified nucleic acid molecule:
  (a) encoding MDK1 polypeptide comprising the intracellular domain as set forth by amino acids 580 to 998 of SEQ ID NO:2 and at least one MDK1 domains selected from the group consisting of amino acids 18 to 538 of SEQ ID NO:2, or amino acids 555 to 579 of SEQ ID NO:2; or
  (b) a nucleic acid molecule that is completely complementary to the nucleic acid molecule of (a).

8. A host cell which is generically engineered to express the nucleic acid of claim, 5, 6, or 7.

9. A recombinant nucleic acid:
  (a) encoding a MDK1 polypeptide comprising the amino acid sequence set forth in SEQ ID NO:2; or
  (b) a nucleic acid molecule that is completely complementary to the nucleic acid molecule of (a).

10. A recombinant nucleic acid:
  (a) encoding MDK1 polypeptide comprising the intracellular domain as set forth by amino acids 580 to 998 of SEQ ID NO:2; or
  (b) a nucleic acid molecule that is completely complementary to the nucleic acid molecule of (a).

11. A recombinant nucleic acid:
  (a) encoding MDK1.Δ1 set forth in SEQ ID NO.11, or MDK1Δ2 set forth in SEQ ID NO:12 or
  (b) a nucleic acid molecule that is completely complementary to the nucleic acid molecule of(a).

12. A recombinant nucleic acid:
  (a) encoding MDK1 polypeptide comprising the intracellular domain as set forth by amino acids 580 to 998 of SEQ ID NO:2 and at least one MDK1 domains selected from the group consisting of amino acids 18 to 538 of SEQ ID NO:2 or amino acids 555 to 579 of SEQ ID NO:2; or
  (b) a nucleic acid molecule that is completely complementary to the nucleic acid molecule of (a).

13. A host which is generically engineered to express the nucleic acid of claim, 9, 10, 11, or 12.

14. An isolated, enriched, or purified nucleic acid molecule comprising
  (a) the nucleotide sequence set forth in SEQ ID NO:1; or
  (b) a nucleic acid molecule that is completely complementary to the nucleic acid molecule of (a).

* * * * *

```
                          SEQUENCE LISTING (1) GENERAL INFORMATION:

(iii) NUMBER OF SEQUENCES:       12

(2) INFORMATION FOR SEQ ID NO:  1:

(i) SEQUENCE CHARACTERISTICS:
            (A) LENGTH:        4304 base pairs
            (B) TYPE:          nucleic acid
            (C) STRANDEDNESS:    single
            (D) TOPOLOGY:      linear (ii) MOLECULE TYPE:      nucleic (xi) SEQUENCE DESCRIPTION:   SEQ ID NO:   1:

AAGCGGCCGG TCTGCAGTCG GAGACTTGCA GGCAGCAAAC ACGGTGCGAA            50

CGAACCGGAG GGGGGAGAGA GAAATCAAAC AGCTAAGCGT GGAGCAGACG           100

GCCTGGGACC CAGAAGGGGA TCGATGCGAG GAGCGCAATA ATAACAACAA           150

TAATAACCCA CTTCGGAGCA AACAGCATCT AAAGAGCTGC GACCCAACTG           200

CAGCCTAAAA AAATCAAACC TGCTCATGCA CCATGGTTGT TCAAACTCGG           250

TTCCCTTCGT GGATTATTTT GTGTTACATC TGGCTGCTTG GCTTTGCACA           300

CACGGGGGAG GCGCAGGCTG CGAAGGAAGT ACTATTACTG GACTCGAAAG           350

CACAACAAAC AGAATTGGAA TGGATTTCCT CTCCACCCAG TGGGTGGGAA           400
```

```
GAAATTAGTG GTTTGGATGA GAACTACACT CCGATAAGAA CATACCAGGT       450

GTGCCAGGTC ATGGAGCCCA ACCAGAACAA CTGGCTGCGG ACTAACTGGA       500

TTTCTAAAGG CAACGCACAA AGGATTTTTG TAGAATTGAA ATTCACCTTG       550

AGGGATTGTA ATAGTCTTCC CGGAGTCCTG GAACTTGCA  AGGAAACGTT       600

TAATTTGTAC TATTATGAAA CAGACTACGA CACCGGCAGG AATATACGAG       650

AAAACCTTTA TGTTAAAATA GACACCATTG CTGCAGATGA AAGTTTCACA       700

CAAGGTGACC TTGGTGAAAG AAAGATGAAG CTGAACACTG AGGTGAGAGA       750

GATTGGACCT TTGTCCAAAA AGGGATTCTA TCTTGCCTTT CAGGATGTAG       800

GGGCTTGCAT AGCATTGGTT TCTGTCAAAG TGTACTACAA GAAGTGCTGG       850

ACCATTGTTG AGAACTTAGC TGTCTTTCCA GATACAGTGA CTGGTTCGGA       900

ATTTTCCTCC TTAGTCGAGG TCCGTGGGAC ATGTGTCAGC AGTGCCGAGG       950

AAGAGGCAGA AAATTCCCCC AGAATGCATT GCAGTGCAGA AGGAGAGTGG      1000

CTAGTACCCA TTGGAAAATG CATCTGCAAA GCAGGCTATC AGCAAAAAGG      1050

GGACACTTGC GAACCCTGTG GCCGCAGGTT CTACAAATCT TCCTCTCAGG      1100

ATCTCCAGTG TTCTCGTTGT CCAACCCACA GCTTCTCTGA CCGAGAAGGA      1150

TCATCCAGGT GTGAATGTGA AGATGGGTAC TACAGAGCTC CTTCTGATCC      1200

ACCATACGTT GCATGCACGA GGCCTCCCTC TGCACCACAG AACCTTATTT      1250

TCAATATCAA TCAAACGACT GTAAGTTTGG AATGGAGTCC TCCGGCTGAC      1300

AACGGGGAA  GAAACGATGT CACCTACAGA ATACTGTGTA AGCGGTGCAG      1350

TTGGGAACAG GGAGAATGTG TGCCATGCGG AAGTAACATT GGATACATGC      1400

CCCAGCAGAC GGGATTAGAG GATAACTATG TCACTGTCAT GGACCTACTT      1450

GCCCATGCAA ATTACACTTT CGAAGTTGAA GCTGTAAATG GAGTTTCGGA      1500

CTTAAGCAGA TCCCAGAGGC TCTTCGCTGC TGTTAGCATC ACCACCGGTC      1550

AAGCAGCTCC CTCGCAAGTG AGTGGAGTCA TGAAGGAGCG AGTACTGCAG      1600

CGGAGTGTGC AGCTTTCCTG GCAGGAGCCG GAGCATCCCA ATGGAGTCAT      1650

CACGGAATAT GAAATCAAGT ATTATGAGAA AGATCAACGG GAAAGGACGT      1700

ACTCAACACT CAAAACCAAG TCCACCTCCG CCTCCATTAA TAATCTGAAA      1750

CCGGGAACAG TGTACGTCTT TCAGATCCGG GCGGTCACTG CTGCCGGTTA      1800

TGGAAACTAC AGCCCTAGGC TTGATGTTGC CACACTTGAG GAAGCTTCAG      1850

GTAAAATGTT TGAAGCGACA GCAGTCTCCA GTGAACAGAA TCCTGTCATC      1900

ATAATTGCTG TAGTGGCTGT AGCAGGGACC ATCATCTTGG TGTTCATGGT      1950

GTTCGGCTTC ATCATTGGAA GAAGGCACTG TGGTTATAGC AAGGCTGACC      2000

AAGAAGGGGA TGAAGAACTC TACTTTCATT TTAAATTTCC AGGCACCAAA      2050

ACCTACATTG ACCCTGAAAC CTATGAGGAC CCAAATAGAG CTGTCCATCA      2100

ATTCGCCAAG GAGCTAGATG CCTCCTGTAT TAAAATTGAG CGTGTGATTG      2150

GTGCAGGAGA ATTTGGAGAA GTTTGCAGTG GTCGTTTGAA ACTTCCGGGC      2200

CAGAGAGATG TTGCAGTGGC CATAAAAACC CTGAAAGTTG GTTACACAGA      2250

AAAGCAAAGG AGGGACTTTT TATGCGAAGC AAGCATCATG GGGCAATTTG      2300

ACCACCCAAA TGTCGTCCAT TTGGAAGGGG TTGTTACAAG AGGGAAGCCT      2350

GTCATGATTG TGATAGAGTT CATGGAGAAT GGAGCCCTGG ATGCATTTCT      2400
```

| | |
|---|---|
| CAGGAAACAC GATGGGCAGT TTACAGTCAT TCAGTTGGTA GGAATGTTGA | 2450 |
| GAGGTATTGC CGCTGGGATG CGATACTTGG CTGATATGGG ATACGTTCAC | 2500 |
| AGGGACCTTG CAGCGCGCAA CATCCTTGTC AACAGCAATC TTGTTTGTAA | 2550 |
| AGTGTCAGAT TTTGGCCTTT CCCGGGTTAT AGAGGATGAT CCCGAAGCTG | 2600 |
| TCTACACCAC GACTGGTGGA AAAATTCCAG TAAGGTGGAC TGCACCGGAA | 2650 |
| GCCATTCAAT ACCGGAAGTT CACCTCAGCC AGCGATGTGT GGAGCTATGG | 2700 |
| GATTGTCATG TGGGAAGTGA TGTCTTATGG AGAAAGACCT TACTGGGACA | 2750 |
| TGTCAAATCA AGATGTCATT AAAGCGATAG AAGAAGGTTA TCGTTTGCCG | 2800 |
| GCGCCCATGG ATTGCCCAGC TGGTCTTCAC CAGCTAATGC TGGATTGTTG | 2850 |
| GCAGAAAGAT CGGGCGGAAA GGCCAAAGTT TGAGCAGATA GTCGGAATTC | 2900 |
| TAGACAAAAT GATTCGAAAC CCAAGTAGTC TGAAAACACC CCTGGGAACT | 2950 |
| TGTAGTAGAC CCTTAAGCCC TCTTCTGGAC CAGAGCACTC CTGACTTCAC | 3000 |
| TGCCTTCTGT TCAGTTGGAG AATGGTTGCA AGCTATTAAA ATGGAAAGGT | 3050 |
| ATAAGGACAA CTTCACAGCA GCGGGTTACA ACTCACTCGA GTCAGTGGCC | 3100 |
| AGGATGACTA TCGATGATGT GATGAGTTTA GGGATCACAC TGGTTGGCCA | 3150 |
| TCAAAAGAAG ATCATGAGCA GCATCCAGAC TATGCGGGCA CAAATGTTGC | 3200 |
| ATTTACACGG AACAGGCATC CAAGTGTGAC ACATCGGCCT CCCTCAGATG | 3250 |
| AGGCTTAAGA CTGCAGGAGA ACAGTTCTGG CCTTCAGTAT ACGCATAGAA | 3300 |
| TGCTGCTAGA AGACAGTTGA TATACTGGGT CCTTCCTACA AGAAAGAGAA | 3350 |
| GATTTTAGAA GCACCTCCAG ACTTGAACTC CTAAGTGCCA CCAGAATATA | 3400 |
| CAAAAAGGGA ATTTAGGATC CACCACTGGT GGCCAGGAAC ACAGCAGAGA | 3450 |
| CAATAAACAA AGTACTACCT GAAAACATC CCAACACCTT GAGCTCTCGA | 3500 |
| ACCTCCTTTT TATCTTATAG ACTTTTTAAA AATGTACATA AAGAATTTAA | 3550 |
| GAAAGAATAT ATTTGTCAAA TAAAAATCAT GATCTTATTG TTAAAATCAA | 3600 |
| TGAAATATTT TCCTTAAAAT ATGTGATTTC AGACTATTCT TTTCCAGAAC | 3650 |
| CATCTGTGTT TATTCTGCTT AAGGACTTTG TTTTAGAAAG TTATTTGTAG | 3700 |
| CTTTGGACCT TTTTAGTGTT AAATTTATGA CACGTTACTA CACTGGGAAC | 3750 |
| CTTTGAAGAC TCTCAAACTT AAAGGAAAGC AAAACTACGC ACATAGTCGA | 3800 |
| GGATGGACTT TGTCCTTCAT GGCTTTGGTA TCCTGGCTGT GTCATTTTGT | 3850 |
| TAAACCAGTG ATGTTTTCAT ATTGTTTGCT GATTGGCAGG TAGTTCAAAA | 3900 |
| TTGCAAGTTG CCAAGAGCTC TGATATTTTT TAACAGGATT TTTTTTTCTT | 3950 |
| TGTAAAAATC AGATAACATA CTAACTTTTC AATGAAAAAA AAAAAAAAAG | 4000 |
| AAGCAATAAT GATCCATAAA TACTATAAGG CACTTTTAAC AGATTGTTTA | 4050 |
| TAGAGTGATT TACTAGGCAG AATTTAATAA AAAAAAAAGA GAGATGTCAA | 4100 |
| ATTTTAGGTT TATGTGTATA TGATAAAAGG CTGAGCTTCG TCTGAAGATG | 4150 |
| CTGGTGAAAG CAAGACTGGA AGCGAAGCTC TCCAGCTTTG GCTAACCCAA | 4200 |
| TCCGAGCACA TCAAGAGCTT CAGTCTTGTG ACAGTAAGAA ATTTAGGAAC | 4250 |
| ATAGTTGACC TATATTTTGT ATTCTTTCTT GTTGAATGCA GTCCAAATAC | 4300 |
| AAAA | 4304 |

(2) INFORMATION FOR SEQ ID NO: 2:

(i) SEQUENCE CHARACTERISTICS:
        (A) LENGTH:       998 amino acids
        (B) TYPE:         amino acid
        (C) STRANDEDNESS:  single
        (D) TOPOLOGY:     linear (ii) MOLECULE TYPE:     peptide (xi) SEQUENCE DESCRIPTION: SEQ ID NO: 2:

```
Met Val Val Gln Thr Arg Phe Pro Ser Trp Ile Ile Leu Cys Tyr Ile
1               5                   10                  15

Trp Leu Leu Gly Phe Ala His Thr Gly Glu Ala Gln Ala Ala Lys Glu
                20                  25                  30

Val Leu Leu Asp Ser Lys Ala Gln Gln Thr Glu Leu Glu Trp Ile
            35                  40                  45

Ser Ser Pro Pro Ser Gly Trp Glu Glu Ile Ser Gly Leu Asp Glu Asn
50                  55                  60

Tyr Thr Pro Ile Arg Thr Tyr Gln Val Cys Gln Val Met Glu Pro Asn
65                  70                  75                  80

Gln Asn Asn Trp Leu Arg Thr Asn Trp Ile Ser Lys Gly Asn Ala Gln
                85                  90                  95

Arg Ile Phe Val Glu Leu Lys Phe Thr Leu Arg Asp Cys Asn Ser Leu
                100                 105                 110

Pro Gly Val Leu Gly Thr Cys Lys Glu Thr Phe Asn Leu Tyr Tyr Tyr
                115                 120                 125

Glu Thr Asp Tyr Asp Thr Gly Arg Asn Ile Arg Glu Asn Leu Tyr Val
130                 135                 140

Lys Ile Asp Thr Ile Ala Ala Asp Glu Ser Phe Thr Gln Gly Asp Leu
145                 150                 155                 160

Gly Glu Arg Lys Met Lys Leu Asn Thr Glu Val Arg Glu Ile Gly Pro
                165                 170                 175

Leu Ser Lys Lys Gly Phe Tyr Leu Ala Phe Gln Asp Val Gly Ala Cys
                180                 185                 190

Ile Ala Leu Val Ser Val Lys Val Tyr Tyr Lys Lys Cys Trp Thr Ile
                195                 200                 205

Val Glu Asn Leu Ala Val Phe Pro Asp Thr Val Thr Gly Ser Glu Phe
210                 215                 220

Ser Ser Leu Val Glu Val Arg Gly Thr Cys Val Ser Ser Ala Glu Glu
225                 230                 235                 240

Glu Ala Glu Asn Ser Pro Arg Met His Cys Ser Ala Glu Gly Glu Trp
                245                 250                 255

Leu Val Pro Ile Gly Lys Cys Ile Cys Lys Ala Gly Tyr Gln Gln Lys
                260                 265                 270

Gly Asp Thr Cys Glu Pro Cys Gly Arg Arg Phe Tyr Lys Ser Ser Ser
                275                 280                 285

Gln Asp Leu Gln Cys Ser Arg Cys Pro Thr His Ser Phe Ser Asp Arg
                290                 295                 300

Glu Gly Ser Ser Arg Cys Glu Cys Glu Asp Gly Tyr Tyr Arg Ala Pro
305                 310                 315                 320

Ser Asp Pro Pro Tyr Val Ala Cys Thr Arg Pro Pro Ser Ala Pro Gln
                325                 330                 335

Asn Leu Ile Phe Asn Ile Asn Gln Thr Thr Val Ser Leu Glu Trp Ser
                340                 345                 350
```

-continued

```
Pro Pro Ala Asp Asn Gly Gly Arg Asn Asp Val Thr Tyr Arg Ile Leu
        355                 360                 365

Cys Lys Arg Cys Ser Trp Glu Gln Gly Glu Cys Val Pro Cys Gly Ser
        370                 375                 380

Asn Ile Gly Tyr Met Pro Gln Gln Thr Gly Leu Glu Asp Asn Tyr Val
385                 390                 395                 400

Thr Val Met Asp Leu Leu Ala His Ala Asn Tyr Thr Phe Glu Val Glu
                405                 410                 415

Ala Val Asn Gly Val Ser Asp Leu Ser Arg Ser Gln Arg Leu Phe Ala
                420                 425                 430

Ala Val Ser Ile Thr Thr Gly Gln Ala Ala Pro Ser Gln Val Ser Gly
                435                 440                 445

Val Met Lys Glu Arg Val Leu Gln Arg Ser Val Gln Leu Ser Trp Gln
        450                 455                 460

Glu Pro Glu His Pro Asn Gly Val Ile Thr Glu Tyr Glu Ile Lys Tyr
465                 470                 475                 480

Tyr Glu Lys Asp Gln Arg Glu Arg Thr Tyr Ser Thr Leu Lys Thr Lys
                485                 490                 495

Ser Thr Ser Ala Ser Ile Asn Asn Leu Lys Pro Gly Thr Val Tyr Val
                500                 505                 510

Phe Gln Ile Arg Ala Val Thr Ala Ala Gly Tyr Gly Asn Tyr Ser Pro
        515                 520                 525

Arg Leu Asp Val Ala Thr Leu Glu Glu Ala Ser Gly Lys Met Phe Glu
        530                 535                 540

Ala Thr Ala Val Ser Ser Glu Gln Asn Pro Val Ile Ile Ala Val
545                 550                 555                 560

Val Ala Val Ala Gly Thr Ile Ile Leu Val Phe Met Val Phe Gly Phe
                565                 570                 575

Ile Ile Gly Arg Arg His Cys Gly Tyr Ser Lys Ala Asp Gln Glu Gly
                580                 585                 590

Asp Glu Glu Leu Tyr Phe His Phe Lys Phe Pro Gly Thr Lys Thr Tyr
        595                 600                 605

Ile Asp Pro Glu Thr Tyr Glu Asp Pro Asn Arg Ala Val His Gln Phe
610                 615                 620

Ala Lys Glu Leu Asp Ala Ser Cys Ile Lys Ile Glu Arg Val Ile Gly
625                 630                 635                 640

Ala Gly Glu Phe Gly Glu Val Cys Ser Gly Arg Leu Lys Leu Pro Gly
                645                 650                 655

Gln Arg Asp Val Ala Val Ala Ile Lys Thr Leu Lys Val Gly Tyr Thr
                660                 665                 670

Glu Lys Gln Arg Arg Asp Phe Leu Cys Glu Ala Ser Ile Met Gly Gln
        675                 680                 685

Phe Asp His Pro Asn Val Val His Leu Glu Gly Val Val Thr Arg Gly
        690                 695                 700

Lys Pro Val Met Ile Val Ile Glu Phe Met Glu Asn Gly Ala Leu Asp
705                 710                 715                 720

Ala Phe Leu Arg Lys His Asp Gly Gln Phe Thr Val Ile Gln Leu Val
                725                 730                 735

Gly Met Leu Arg Gly Ile Ala Ala Gly Met Arg Tyr Leu Ala Asp Met
                740                 745                 750

Gly Tyr Val His Arg Asp Leu Ala Ala Arg Asn Ile Leu Val Asn Ser
                755                 760                 765

Asn Leu Val Cys Lys Val Ser Asp Phe Gly Leu Ser Arg Val Ile Glu
```

```
                    770             775             780
Asp Asp Pro Glu Ala Val Tyr Thr Thr Thr Gly Gly Lys Ile Pro Val
785             790             795             800

Arg Trp Thr Ala Pro Glu Ala Ile Gln Tyr Arg Lys Phe Thr Ser Ala
                805             810             815

Ser Asp Val Trp Ser Tyr Gly Ile Val Met Trp Glu Val Met Ser Tyr
                820             825             830

Gly Glu Arg Pro Tyr Trp Asp Met Ser Asn Gln Asp Val Ile Lys Ala
                835             840             845

Ile Glu Glu Gly Tyr Arg Leu Pro Ala Pro Met Asp Cys Pro Ala Gly
850             855             860

Leu His Gln Leu Met Leu Asp Cys Trp Gln Lys Asp Arg Ala Glu Arg
865             870             875             880

Pro Lys Phe Glu Gln Ile Val Gly Ile Leu Asp Lys Met Ile Arg Asn
                885             890             895

Pro Ser Ser Leu Lys Thr Pro Leu Gly Thr Cys Ser Arg Pro Leu Ser
                900             905             910

Pro Leu Leu Asp Gln Ser Thr Pro Asp Phe Thr Ala Phe Cys Ser Val
                915             920             925

Gly Glu Trp Leu Gln Ala Ile Lys Met Glu Arg Tyr Lys Asp Asn Phe
930             935             940

Thr Ala Ala Gly Tyr Asn Ser Leu Glu Ser Val Ala Arg Met Thr Ile
945             950             955             960

Asp Asp Val Met Ser Leu Gly Ile Thr Leu Val Gly His Gln Lys Lys
                965             970             975

Ile Met Ser Ser Ile Gln Thr Met Arg Ala Gln Met Leu His Leu His
                980             985             990

Gly Thr Gly Ile Gln Val
            995

(2) INFORMATION FOR SEQ ID NO: 3:

(i) SEQUENCE CHARACTERISTICS:
        (A) LENGTH:       610 amino acids
        (B) TYPE:         amino acid
        (C) STRANDEDNESS: single
        (D) TOPOLOGY:     linear (ii) MOLECULE TYPE:    peptide (xi) SEQUENCE DESCRIPTION: SEQ ID NO: 3:

Met Val Val Gln Thr Arg Phe Pro Ser Trp Ile Ile Leu Cys Tyr Ile
1               5               10              15

Trp Leu Leu Gly Phe Ala His Thr Gly Glu Ala Gln Ala Ala Lys Glu
                20              25              30

Val Leu Leu Leu Asp Ser Lys Ala Gln Gln Thr Glu Leu Glu Trp Ile
                35              40              45

Ser Ser Pro Pro Ser Gly Trp Glu Glu Ile Ser Gly Leu Asp Glu Asn
50              55              60

Tyr Thr Pro Ile Arg Thr Tyr Gln Val Cys Gln Val Met Glu Pro Asn
65              70              75              80

Gln Asn Asn Trp Leu Arg Thr Asn Trp Ile Ser Lys Gly Asn Ala Gln
                85              90              95

Arg Ile Phe Val Glu Leu Lys Phe Thr Leu Arg Asp Cys Asn Ser Leu
                100             105             110

Pro Gly Val Leu Gly Thr Cys Lys Glu Thr Phe Asn Leu Tyr Tyr Tyr
```

-continued

```
            115                 120                 125
Glu Thr Asp Tyr Asp Thr Gly Arg Asn Ile Arg Glu Asn Leu Tyr Val
    130                 135                 140
Lys Ile Asp Thr Ile Ala Ala Asp Glu Ser Phe Thr Gln Gly Asp Leu
145                 150                 155                 160
Gly Glu Arg Lys Met Lys Leu Asn Thr Glu Val Arg Glu Ile Gly Pro
                165                 170                 175
Leu Ser Lys Lys Gly Phe Tyr Leu Ala Phe Gln Asp Val Gly Ala Cys
            180                 185                 190
Ile Ala Leu Val Ser Val Lys Val Tyr Lys Lys Cys Trp Thr Ile
        195                 200                 205
Val Glu Asn Leu Ala Val Phe Pro Asp Thr Val Thr Gly Ser Glu Phe
    210                 215                 220
Ser Ser Leu Val Glu Val Arg Gly Thr Cys Val Ser Ser Ala Glu Glu
225                 230                 235                 240
Glu Ala Glu Asn Ser Pro Arg Met His Cys Ser Ala Glu Gly Glu Trp
                245                 250                 255
Leu Val Pro Ile Gly Lys Cys Ile Cys Lys Ala Gly Tyr Gln Gln Lys
            260                 265                 270
Gly Asp Thr Cys Glu Pro Cys Gly Arg Arg Phe Tyr Lys Ser Ser Ser
        275                 280                 285
Gln Asp Leu Gln Cys Ser Arg Cys Pro Thr His Ser Phe Ser Asp Arg
    290                 295                 300
Glu Gly Ser Ser Arg Cys Glu Cys Glu Asp Gly Tyr Tyr Arg Ala Pro
305                 310                 315                 320
Ser Asp Pro Pro Tyr Val Ala Cys Thr Arg Pro Pro Ser Ala Pro Gln
                325                 330                 335
Asn Leu Ile Phe Asn Ile Asn Gln Thr Thr Val Ser Leu Glu Trp Ser
            340                 345                 350
Pro Pro Ala Asp Asn Gly Gly Arg Asn Asp Val Thr Tyr Arg Ile Leu
        355                 360                 365
Cys Lys Arg Cys Ser Trp Glu Gln Gly Glu Cys Val Pro Cys Gly Ser
    370                 375                 380
Asn Ile Gly Tyr Met Pro Gln Gln Thr Gly Leu Glu Asp Asn Tyr Val
385                 390                 395                 400
Thr Val Met Asp Leu Leu Ala His Ala Asn Tyr Thr Phe Glu Val Glu
                405                 410                 415
Ala Val Asn Gly Val Ser Asp Leu Ser Arg Ser Gln Arg Leu Phe Ala
            420                 425                 430
Ala Val Ser Ile Thr Thr Gly Gln Ala Pro Ser Gln Val Ser Gly
        435                 440                 445
Val Met Lys Glu Arg Val Leu Gln Arg Ser Val Gln Leu Ser Trp Gln
    450                 455                 460
Glu Pro Glu His Pro Asn Gly Val Ile Thr Glu Tyr Glu Ile Lys Tyr
465                 470                 475                 480
Tyr Glu Lys Asp Gln Arg Glu Arg Thr Tyr Ser Thr Leu Lys Thr Lys
                485                 490                 495
Ser Thr Ser Ala Ser Ile Asn Asn Leu Lys Pro Gly Thr Val Tyr Val
            500                 505                 510
Phe Gln Ile Arg Ala Val Thr Ala Ala Gly Tyr Gly Asn Tyr Ser Pro
        515                 520                 525
Arg Leu Asp Val Ala Thr Leu Glu Glu Ala Ser Gly Lys Met Phe Glu
    530                 535                 540
```

```
Ala Thr Ala Val Ser Ser Glu Gln Asn Pro Val Ile Ile Ile Ala Val
545                 550                 555                 560

Val Ala Val Ala Gly Thr Ile Ile Leu Val Phe Met Val Phe Gly Phe
                565                 570                 575

Ile Ile Gly Arg Arg His Cys Gly Tyr Ser Lys Ala Asp Gln Glu Gly
            580                 585                 590

Asp Glu Glu Leu Tyr Phe His Ser Leu Val Thr Asn Glu His Leu Ser
        595                 600                 605

Val Leu
    610

(2) INFORMATION FOR SEQ ID NO: 4:

(i) SEQUENCE CHARACTERISTICS:
        (A) LENGTH:        2901 base pairs
        (B) TYPE:          nucleic acid
        (C) STRANDEDNESS:    single
        (D) TOPOLOGY:      linear (ii) MOLECULE TYPE:    nucleic (xi) SEQUENCE DESCRIPTION: SEQ ID NO: 4:
```

| | | |
|---|---|---|
| AAGCGGCCGG TCTGCAGTCG AGAGACTTGCA GGCAGCAAAC ACGGTGCGAA | | 50 |
| CGAACCGGAG GGGGGAGAGA GAAATCAAAC AGCTAAGCGT GGAGCAGACG | | 100 |
| GCCTGGGACC CAGAAGGGGA TCGATGCGAG GAGCGCAATA TAACAACAA | | 150 |
| TAATAACCCA CTTCGGAGCA ACAGCATCT AAAGAGCTGC GACCCAACTG | | 200 |
| CAGCCTAAAA AAATCAAACC TGCTCATGCA CCATGGTTGT TCAAACTCGG | | 250 |
| TTCCCTTCGT GGATTATTTT GTGTTACATC TGGCTGCTTG GCTTTGCACA | | 300 |
| CACGGGGAG GCGCAGGCTG CGAAGGAAGT ACTATTACTG GACTCGAAAG | | 350 |
| CACAACAAAC AGAATTGGAA TGGATTTCCT CTCCACCCAG TGGGTGGGAA | | 400 |
| GAAATTAGTG GTTTGGATGA GAACTACACT CCGATAAGAA CATACCAGGT | | 450 |
| GTGCCAGGTC ATGGAGCCCA ACCAGAACAA CTGGCTGCGG ACTAACTGGA | | 500 |
| TTTCTAAAGG CAACGCACAA AGGATTTTTG TAGAATTGAA ATTCACCTTG | | 550 |
| AGGGATTGTA ATAGTCTTCC CGGAGTCCTG GGAACTTGCA AGGAAACGTT | | 600 |
| TAATTTGTAC TATTATGAAA CAGACTACGA CACCGGCAGG AATATACGAG | | 650 |
| AAAACCTTTA TGTTAAAATA GACACCATTG CTGCAGATGA AAGTTTCACA | | 700 |
| CAAGGTGACC TTGGTGAAAG AAAGATGAAG CTGAACACTG AGGTGAGAGA | | 750 |
| GATTGGACCT TTGTCCAAAA AGGGATTCTA TCTTGCCTTT CAGGATGTAG | | 800 |
| GGGCTTGCAT AGCATTGGTT TCTGTCAAAG TGTACTACAA GAAGTGCTGG | | 850 |
| ACCATTGTTG AGAACTTAGC TGTCTTTCCA GATACAGTGA CTGGTTCGGA | | 900 |
| ATTTTCCTCC TTAGTCGAGG TCCGTGGGAC ATGTGTCAGC AGTGCCGAGG | | 950 |
| AAGAGGCAGA AAATTCCCCC AGAATGCATT GCAGTGCAGA AGGAGAGTGG | | 1000 |
| CTAGTACCCA TTGGAAAATG CATCTGCAAA GCAGGCTATC AGCAAAAAGG | | 1050 |
| GGACACTTGC GAACCCTGTG GCCGCAGGTT CTACAAATCT TCCTCTCAGG | | 1100 |
| ATCTCCAGTG TTCTCGTTGT CCAACCCACA GCTTCTCTGA CCGAGAAGGA | | 1150 |
| TCATCCAGGT GTGAATGTGA AGATGGGTAC TACAGAGCTC TTCTGATCC | | 1200 |
| ACCATACGTT GCATGCACGA GGCCTCCCTC TGCACCACAG AACCTTATTT | | 1250 |

-continued

```
TCAATATCAA TCAAACGACT GTAAGTTTGG AATGGAGTCC TCCGGCTGAC         1300

AACGGGGGAA GAAACGATGT CACCTACAGA ATACTGTGTA AGCGGTGCAG         1350

TTGGGAACAG GGAGAATGTG TGCCATGCGG AAGTAACATT GGATACATGC        1400

CCCAGCAGAC GGGATTAGAG GATAACTATG TCACTGTCAT GGACCTACTT        1450

GCCCATGCAA ATTACACTTT CGAAGTTGAA GCTGTAAATG GAGTTTCGGA        1500

CTTAAGCAGA TCCCAGAGGC TCTTCGCTGC TGTTAGCATC ACCACCGGTC        1550

AAGCAGCTCC CTCGCAAGTG AGTGGAGTCA TGAAGGAGCG AGTACTGCAG        1600

CGGAGTGTGC AGCTTTCCTG GCAGGAGCCG GAGCATCCCA ATGGAGTCAT        1650

CACGGAATAT GAAATCAAGT ATTATGAGAA AGATCAACGG GAAAGGACGT        1700

ACTCAACACT CAAACCAAG TCCACCTCCG CCTCCATTAA TAATCTGAAA         1750

CCGGGAACAG TGTACGTCTT TCAGATCCGG GCGGTCACTG CTGCCGGTTA        1800

TGGAAACTAC AGCCCTAGGC TTGATGTTGC CACACTTGAG GAAGCTTCAG        1850

GTAAAATGTT TGAAGCGACA GCAGTCTCCA GTGAACAGAA TCCTGTCATC        1900

ATAATTGCTG TAGTGGCTGT AGCAGGGACC ATCATCTTGG TGTTCATGGT        1950

GTTCGGCTTC ATCATTGGAA GAAGGCACTG TGGTTATAGC AAGGCTGACC        2000

AAGAAGGGGA TGAAGAACTC TACTTTCATT CTTTAGTAAC AAATGAGCAC        2050

CTGTCAGTTT TATAAACCGC AACAATAACT GTTTAAGACA ATCAATTTTG        2100

GATAAACAAT CAACTACAGC AGAATAAATC AAGATTTTTA AGTCCCATTT        2150

TCCTTTATAC ATTCTGCTTA TTTTGTTGTT ATATGTTTAT TTTTTAAACT        2200

CTGATCTTGA TTGAATGTGA TACCATAAGC ACAGTTAGGG TGCAGTGTAA        2250

ATATATAAAG ACATTGTTCT GAGAGCAGTA CGATTTCATG GAAAGATTGT        2300

TTGGTGGCTT TGTTAAAATT AATAAAGAAT TTTTAAGGAT ATAGTGTAAT        2350

TTTCTTCATT GCATTAATAT AACCAAATAT GCCTACCTAT CTTTGTCTTG        2400

AACCAAATGA ATAGATTTGG AATACTTTAT TGTAATTGAA TTTGATATAA        2450

AGTTGACTGA GCATTTATGT GTTACCTGCA TGCTTCTGGG TGCATTGAAA        2500

TATTTTAACT TTTAAAATGA TACTATGTTG TTTCAATTTT GACTACCTTT        2550

TGTGAGGCAT ACTGGCTACC TCCTCCTATT AGCTAAGATC TTCCAAAGCC        2600

TTATAATGAA AAGTTTATAT AAACCATTTC TCTTTCAAAT CACTGTCATA        2650

CTTGGTCACG GATCCCAGGA ATATTGTAAA TTTTCTAATT TACTCTGCAC        2700

TTTGTATATC CAGCCTCTAT TACCCTCAAG GTGAATATAA AACTATGTCT        2750

TTTGAATATT TCTCTTTGAT TTGTGATAG  CAGTCCCTCA TATCTTGTAC        2800

TAATTTTATG TATATGTCAA CAGTGGTTGG TCTTTAAAAA TAAATCAAAG        2850

AATAAGTAAA AAAAAAAAA  AAAAAAAAA  AAAATAAAA  AAAAAAAAA         2900

A                                                              2901
```

(2) INFORMATION FOR SEQ ID NO: 5:

(i) SEQUENCE CHARACTERISTICS:
        (A) LENGTH:      626 amino acids
        (B) TYPE:        amino acid
        (C) STRANDEDNESS:   single
        (D) TOPOLOGY:    linear (ii) MOLECULE TYPE:    peptide -continued (xi) SEQUENCE DESCRIPTION: SEQ ID NO: 5:

```
Met Val Val Gln Thr Arg Phe Pro Ser Trp Ile Ile Leu Cys Tyr Ile
1               5                   10                  15

Trp Leu Leu Gly Phe Ala His Thr Gly Glu Ala Gln Ala Ala Lys Glu
            20                  25                  30

Val Leu Leu Leu Asp Ser Lys Ala Gln Gln Thr Glu Leu Glu Trp Ile
        35                  40                  45

Ser Ser Pro Pro Ser Gly Trp Glu Glu Ile Ser Gly Leu Asp Glu Asn
50                  55                  60

Tyr Thr Pro Ile Arg Thr Tyr Gln Val Cys Gln Val Met Glu Pro Asn
65                  70                  75                  80

Gln Asn Asn Trp Leu Arg Thr Asn Trp Ile Ser Lys Gly Asn Ala Gln
                85                  90                  95

Arg Ile Phe Val Glu Leu Lys Phe Thr Leu Arg Asp Cys Asn Ser Leu
            100                 105                 110

Pro Gly Val Leu Gly Thr Cys Lys Glu Thr Phe Asn Leu Tyr Tyr Tyr
        115                 120                 125

Glu Thr Asp Tyr Asp Thr Gly Arg Asn Ile Arg Glu Asn Leu Tyr Val
    130                 135                 140

Lys Ile Asp Thr Ile Ala Ala Asp Glu Ser Phe Thr Gln Gly Asp Leu
145                 150                 155                 160

Gly Glu Arg Lys Met Lys Leu Asn Thr Glu Val Arg Glu Ile Gly Pro
                165                 170                 175

Leu Ser Lys Lys Gly Phe Tyr Leu Ala Phe Gln Asp Val Gly Ala Cys
            180                 185                 190

Ile Ala Leu Val Ser Val Lys Val Tyr Lys Lys Cys Trp Thr Ile
        195                 200                 205

Val Glu Asn Leu Ala Val Phe Pro Asp Thr Val Thr Gly Ser Glu Phe
    210                 215                 220

Ser Ser Leu Val Glu Val Arg Gly Thr Cys Val Ser Ser Ala Glu Glu
225                 230                 235                 240

Glu Ala Glu Asn Ser Pro Arg Met His Cys Ser Ala Glu Gly Glu Trp
                245                 250                 255

Leu Val Pro Ile Gly Lys Cys Ile Cys Lys Ala Gly Tyr Gln Gln Lys
            260                 265                 270

Gly Asp Thr Cys Glu Pro Cys Gly Arg Arg Phe Tyr Lys Ser Ser Ser
        275                 280                 285

Gln Asp Leu Gln Cys Ser Arg Cys Pro Thr His Ser Phe Ser Asp Arg
    290                 295                 300

Glu Gly Ser Ser Arg Cys Glu Cys Glu Asp Gly Tyr Tyr Arg Ala Pro
305                 310                 315                 320

Ser Asp Pro Pro Tyr Val Ala Cys Thr Arg Pro Pro Ser Ala Pro Gln
                325                 330                 335

Asn Leu Ile Phe Asn Ile Asn Gln Thr Thr Val Ser Leu Glu Trp Ser
            340                 345                 350

Pro Pro Ala Asp Asn Gly Gly Arg Asn Asp Val Thr Tyr Arg Ile Leu
        355                 360                 365

Cys Lys Arg Cys Ser Trp Glu Gln Gly Glu Cys Val Pro Cys Gly Ser
    370                 375                 380

Asn Ile Gly Tyr Met Pro Gln Gln Thr Gly Leu Glu Asp Asn Tyr Val
385                 390                 395                 400

Thr Val Met Asp Leu Leu Ala His Ala Asn Tyr Thr Phe Glu Val Glu
                405                 410                 415
```

```
Ala Val Asn Gly Val Ser Asp Leu Ser Arg Ser Gln Arg Leu Phe Ala
            420                 425                 430

Ala Val Ser Ile Thr Thr Gly Gln Ala Ala Pro Ser Gln Val Ser Gly
            435                 440                 445

Val Met Lys Glu Arg Val Leu Gln Arg Ser Val Gln Leu Ser Trp Gln
        450                 455                 460

Glu Pro Glu His Pro Asn Gly Val Ile Thr Glu Tyr Glu Ile Lys Tyr
465                 470                 475                 480

Tyr Glu Lys Asp Gln Arg Glu Arg Thr Tyr Ser Thr Leu Lys Thr Lys
                485                 490                 495

Ser Thr Ser Ala Ser Ile Asn Asn Leu Lys Pro Gly Thr Val Tyr Val
            500                 505                 510

Phe Gln Ile Arg Ala Val Thr Ala Ala Gly Tyr Gly Asn Tyr Ser Pro
        515                 520                 525

Arg Leu Asp Val Ala Thr Leu Glu Glu Ala Ser Gly Lys Met Phe Glu
    530                 535                 540

Ala Thr Ala Val Ser Ser Glu Gln Asn Pro Val Ile Ile Ala Val
545                 550                 555                 560

Val Ala Val Ala Gly Thr Ile Ile Leu Val Phe Met Val Phe Gly Phe
                565                 570                 575

Ile Ile Gly Arg Arg His Cys Gly Tyr Ser Lys Ala Asp Gln Glu Gly
            580                 585                 590

Asp Glu Glu Leu Tyr Phe His Ser Leu Tyr Arg Glu Arg Gly Asp Gly
        595                 600                 605

Met Glu Lys Thr Gln His Asn Lys Lys Trp Met Ile Ala Ser Cys Ser
    610                 615                 620

Arg Leu
625

(2) INFORMATION FOR SEQ ID NO: 6:

(i) SEQUENCE CHARACTERISTICS:
        (A) LENGTH:       2323 base pairs
        (B) TYPE:         nucleic acid
        (C) STRANDEDNESS:    single
        (D) TOPOLOGY:     linear (ii) MOLECULE TYPE:      nucleic (xi) SEQUENCE DESCRIPTION: SEQ ID NO: 6:

AAGCGGCCGG TCTGCAGTCG GAGACTTGCA GGCAGCAAAC ACGGTGCGAA         50

CGAACCGGAG GGGGGAGAGA GAAATCAAAC AGCTAAGCGT GGAGCAGACG        100

GCCTGGGACC AGAAGGGGA TCGATGCGAG GAGCGCAATA ATAACAACAA         150

TAATAACCCA CTTCGGAGCA AACAGCATCT AAAGAGCTGC GACCCAACTG        200

CAGCCTAAAA AAATCAAACC TGCTCATGCA CCATGGTTGT TCAAACTCGG        250

TTCCCTTCGT GGATTATTTT GTGTTACATC TGGCTGCTTG GCTTTGCACA        300

CACGGGGGAG GCGCAGGCTG CGAAGGAAGT ACTATTACTG GACTCGAAAG        350

CACAACAAAC AGAATTGGAA TGGATTTCCT CTCCACCCAG TGGGTGGGAA        400

GAAATTAGTG GTTTGGATGA GAACTACACT CCGATAAGAA CATACCAGGT        450

GTGCCAGGTC ATGGAGCCCA ACCAGAACAA CTGGCTGCGG ACTAACTGGA        500

TTTCTAAAGG CAACGCACAA AGGATTTTTG TAGAATTGAA ATTCACCTTG        550

AGGGATTGTA ATAGTCTTCC CGGAGTCCTG GAACTTGCA AGGAAACGTT         600
```

| | | |
|---|---|---|
| TAATTTGTAC TATTATGAAA CAGACTACGA CACCGGCAGG AATATACGAG | | 650 |
| AAAACCTTTA TGTTAAAATA GACACCATTG CTGCAGATGA AAGTTTCACA | | 700 |
| CAAGGTGACC TTGGTGAAAG AAAGATGAAG CTGAACACTG AGGTGAGAGA | | 750 |
| GATTGGACCT TTGTCCAAAA AGGGATTCTA TCTTGCCTTT CAGGATGTAG | | 800 |
| GGGCTTGCAT AGCATTGGTT TCTGTCAAAG TGTACTACAA GAAGTGCTGG | | 850 |
| ACCATTGTTG AGAACTTAGC TGTCTTTCCA GATACAGTGA CTGGTTCGGA | | 900 |
| ATTTTCCTCC TTAGTCGAGG TCCGTGGGAC ATGTGTCAGC AGTGCCGAGG | | 950 |
| AAGAGGCAGA AAATTCCCCC AGAATGCATT GCAGTGCAGA AGGAGAGTGG | | 1000 |
| CTAGTACCCA TTGGAAAATG CATCTGCAAA GCAGGCTATC AGCAAAAAGG | | 1050 |
| GGACACTTGC GAACCCTGTG GCCGCAGGTT CTACAAATCT TCCTCTCAGG | | 1100 |
| ATCTCCAGTG TTCTCGTTGT CCAACCCACA GCTTCTCTGA CCGAGAAGGA | | 1150 |
| TCATCCAGGT GTGAATGTGA AGATGGGTAC TACAGAGCTC CTTCTGATCC | | 1200 |
| ACCATACGTT GCATGCACGA GGCCTCCCTC TGCACCACAG AACCTTATTT | | 1250 |
| TCAATATCAA TCAAACGACT GTAAGTTTGG AATGGAGTCC TCCGGCTGAC | | 1300 |
| AACGGGGAA GAAACGATGT CACCTACAGA ATACTGTGTA AGCGGTGCAG | | 1350 |
| TTGGAACAG GGAGAATGTG TGCCATGCGG AAGTAACATT GGATACATGC | | 1400 |
| CCCAGCAGAC GGGATTAGAG GATAACTATG TCACTGTCAT GGACCTACTT | | 1450 |
| GCCCATGCAA ATTACACTTT CGAAGTTGAA GCTGTAAATG GAGTTTCGGA | | 1500 |
| CTTAAGCAGA TCCCAGAGGC TCTTCGCTGC TGTTAGCATC ACCACCGGTC | | 1550 |
| AAGCAGCTCC CTCGCAAGTG AGTGGAGTCA TGAAGGAGCG AGTACTGCAG | | 1600 |
| CGGAGTGTGC AGCTTTCCTG GCAGGAGCCG GAGCATCCCA ATGGAGTCAT | | 1650 |
| CACGGAATAT GAAATCAAGT ATTATGAGAA AGATCAACGG GAAAGGACGT | | 1700 |
| ACTCAACACT CAAAACCAAG TCCACCTCCG CCTCCATTAA TAATCTGAAA | | 1750 |
| CCGGGAACAG TGTACGTCTT TCAGATCCGG GCGGTCACTG CTGCCGGTTA | | 1800 |
| TGGAAACTAC AGCCCTAGGC TTGATGTTGC CACACTTGAG GAAGCTTCAG | | 1850 |
| GTAAAATGTT TGAAGCGACA GCAGTCTCCA GTGAACAGAA TCCTGTCATC | | 1900 |
| ATAATTGCTG TAGTGGCTGT AGCAGGGACC ATCATCTTGG TGTTCATGGT | | 1950 |
| GTTCGGCTTC ATCATTGGAA GAAGGCACTG TGGTTATAGC AAGGCTGACC | | 2000 |
| AAGAAGGGGA TGAAGAACTC TACTTTCATT CTCTTTACAG GGAAAGGGGA | | 2050 |
| GACGGGATGG AAAAGACACA GCACAATAAG AAGTGGATGA TTGCATCGTG | | 2100 |
| CTCTCGTTTG TAGGTCTCTT TTCCTAATCA ACACTATGAT TTTGAAGTAC | | 2150 |
| GCGTACACGA AGCAAACGGG AAGAGATAAG GAATTAGCAT TGTGAACCTG | | 2200 |
| ACTGTAATCC TCTCTTCCGG AAAGAGATGA GATGCTATTG CGATGAGAAT | | 2250 |
| GTACAACTTG CACCTTGAAA TCTTTTTTGA TAATTAGTGC TCAGGGAGG | | 2300 |
| GGGGGGGAAG TAGAGAAAGC AAA | | 2323 |

(2) INFORMATION FOR SEQ ID NO: 7:

(i) SEQUENCE CHARACTERISTICS:
        (A) LENGTH:     6 amino acids
        (B) TYPE:       amino acid
        (C) STRANDEDNESS: single
        (D) TOPOLOGY:   linear

```
    (ii) MOLECULE TYPE:        peptide (xi) SEQUENCE DESCRIPTION: SEQ ID NO: 7:

Ala Ala Thr Ala Ala Ala
            5

(2) INFORMATION FOR SEQ ID NO: 8:

(i) SEQUENCE CHARACTERISTICS:
        (A) LENGTH:            6 amino acids
        (B) TYPE:              amino acid
        (C) STRANDEDNESS:      single
        (D) TOPOLOGY:          linear (ii) MOLECULE TYPE:        peptide (xi) SEQUENCE DESCRIPTION: SEQ ID NO: 8:

Ala Ala Thr Ala Ala Ala
            5

(2) INFORMATION FOR SEQ ID NO: 9:

(i) SEQUENCE CHARACTERISTICS:
        (A) LENGTH:            6 amino acids
        (B) TYPE:              amino acid
        (C) STRANDEDNESS:      single
        (D) TOPOLOGY:          linear (ii) MOLECULE TYPE:        peptide (xi) SEQUENCE DESCRIPTION: SEQ ID NO: 9:

His Arg Asp Leu Ala Ala
            5

(2) INFORMATION FOR SEQ ID NO: 10:

(i) SEQUENCE CHARACTERISTICS:
        (A) LENGTH:            6 amino acids
        (B) TYPE:              amino acid
        (C) STRANDEDNESS:      single
        (D) TOPOLOGY:          linear (ii) MOLECULE TYPE:        peptide (ix) FEATURE:
        (D) OTHER INFORMATION: Xaa in position 2 is valine
            or methionine; Xaa in
            position 5 is phenylalanine
            or tyrosine.

(xi) SEQUENCE DESCRIPTION: SEQ ID NO: 10:

Asp Xaa Trp Ser Xaa Gly
            5

(2) INFORMATION FOR SEQ ID NO: 11:

(i) SEQUENCE CHARACTERISTICS:
        (A) LENGTH:            993 amino acids
        (B) TYPE:              amino acid
        (C) STRANDEDNESS:      single
        (D) TOPOLOGY:          linear (ii) MOLECULE TYPE:        peptide (xi) SEQUENCE DESCRIPTION: SEQ ID NO: 11:

Met Val Val Gln Thr Arg Phe Pro Ser Trp Ile Ile Leu Cys Tyr Ile
1               5                  10                  15
Trp Leu Leu Gly Phe Ala His Thr Gly Glu Ala Gln Ala Ala Lys Glu
```

-continued

```
                    20                  25                  30
    Val Leu Leu Leu Asp Ser Lys Ala Gln Gln Thr Glu Leu Glu Trp Ile
                    35                  40                  45

Ser Ser Pro Ser Gly Trp Glu Glu Ile Ser Gly Leu Asp Glu Asn
     50                  55                  60

Tyr Thr Pro Ile Arg Thr Tyr Gln Val Cys Gln Val Met Glu Pro Asn
    65                   70                  75                  80

Gln Asn Asn Trp Leu Arg Thr Asn Trp Ile Ser Lys Gly Asn Ala Gln
                     85                  90                  95

Arg Ile Phe Val Glu Leu Lys Phe Thr Leu Arg Asp Cys Asn Ser Leu
                    100                 105                 110

Pro Gly Val Leu Gly Thr Cys Lys Glu Thr Phe Asn Leu Tyr Tyr Tyr
                    115                 120                 125

Glu Thr Asp Tyr Asp Thr Gly Arg Asn Ile Arg Glu Asn Leu Tyr Val
                    130                 135                 140

Lys Ile Asp Thr Ile Ala Ala Asp Glu Ser Phe Thr Gln Gly Asp Leu
    145                 150                 155                 160

Gly Glu Arg Lys Met Lys Leu Asn Thr Glu Val Arg Glu Ile Gly Pro
                    165                 170                 175

Leu Ser Lys Lys Gly Phe Tyr Leu Ala Phe Gln Asp Val Gly Ala Cys
                    180                 185                 190

Ile Ala Leu Val Ser Val Lys Val Tyr Tyr Lys Lys Cys Trp Thr Ile
                    195                 200                 205

Val Glu Asn Leu Ala Val Phe Pro Asp Thr Val Thr Gly Ser Glu Phe
                    210                 215                 220

Ser Ser Leu Val Glu Val Arg Gly Thr Cys Val Ser Ser Ala Glu Glu
    225                 230                 235                 240

Glu Ala Glu Asn Ser Pro Arg Met His Cys Ser Ala Glu Gly Glu Trp
                    245                 250                 255

Leu Val Pro Ile Gly Lys Cys Ile Cys Lys Ala Gly Tyr Gln Gln Lys
                    260                 265                 270

Gly Asp Thr Cys Glu Pro Cys Gly Arg Arg Phe Tyr Lys Ser Ser Ser
                    275                 280                 285

Gln Asp Leu Gln Cys Ser Arg Cys Pro Thr His Ser Phe Ser Asp Arg
                    290                 295                 300

Glu Gly Ser Ser Arg Cys Glu Cys Glu Asp Gly Tyr Tyr Arg Ala Pro
    305                 310                 315                 320

Ser Asp Pro Pro Tyr Val Ala Cys Thr Arg Pro Ser Ala Pro Gln
                    325                 330                 335

Asn Leu Ile Phe Asn Ile Asn Gln Thr Thr Val Ser Leu Glu Trp Ser
                    340                 345                 350

Pro Pro Ala Asp Asn Gly Gly Arg Asn Asp Val Thr Tyr Arg Ile Leu
                    355                 360                 365

Cys Lys Arg Cys Ser Trp Glu Gln Gly Glu Cys Val Pro Cys Gly Ser
                    370                 375                 380

Asn Ile Gly Tyr Met Pro Gln Gln Thr Gly Leu Glu Asp Asn Tyr Val
    385                 390                 395                 400

Thr Val Met Asp Leu Leu Ala His Ala Asn Tyr Thr Phe Glu Val Glu
                    405                 410                 415

Ala Val Asn Gly Val Ser Asp Leu Ser Arg Ser Gln Arg Leu Phe Ala
                    420                 425                 430

Ala Val Ser Ile Thr Thr Gly Gln Ala Ala Pro Ser Gln Val Ser Gly
                    435                 440                 445
```

-continued

```
Val Met Lys Glu Arg Val Leu Gln Arg Ser Val Gln Leu Ser Trp Gln
    450                 455                 460
Glu Pro Glu His Pro Asn Gly Val Ile Thr Glu Tyr Glu Ile Lys Tyr
465                 470                 475                 480
Tyr Glu Lys Asp Gln Arg Glu Arg Thr Tyr Ser Thr Leu Lys Thr Lys
                485                 490                 495
Ser Thr Ser Ala Ser Ile Asn Asn Leu Lys Pro Gly Thr Val Tyr Val
            500                 505                 510
Phe Gln Ile Arg Ala Val Thr Ala Ala Gly Tyr Gly Asn Tyr Ser Pro
        515                 520                 525
Arg Leu Asp Val Ala Thr Leu Glu Glu Ala Ser Ala Thr Ala Val Ser
    530                 535                 540
Ser Glu Gln Asn Pro Val Ile Ile Ala Val Val Ala Val Ala Ala Gly
545                 550                 555                 560
Thr Ile Ile Leu Val Phe Met Val Phe Gly Phe Ile Ile Gly Arg Arg
                565                 570                 575
His Cys Gly Tyr Ser Lys Ala Asp Gln Glu Gly Asp Glu Glu Leu Tyr
            580                 585                 590
Phe His Phe Lys Phe Pro Gly Thr Lys Thr Tyr Ile Asp Pro Glu Thr
        595                 600                 605
Tyr Glu Asp Pro Asn Arg Ala Val His Gln Phe Ala Lys Glu Leu Asp
    610                 615                 620
Ala Ser Cys Ile Lys Ile Glu Arg Val Ile Gly Ala Gly Glu Phe Gly
625                 630                 635                 640
Glu Val Cys Ser Gly Arg Leu Lys Leu Pro Gly Gln Arg Asp Val Ala
                645                 650                 655
Val Ala Ile Lys Thr Leu Lys Val Gly Tyr Thr Glu Lys Gln Arg Arg
            660                 665                 670
Asp Phe Leu Cys Glu Ala Ser Ile Met Gly Gln Phe Asp His Pro Asn
        675                 680                 685
Val Val His Leu Glu Gly Val Val Thr Arg Gly Lys Pro Val Met Ile
    690                 695                 700
Val Ile Glu Phe Met Glu Asn Gly Ala Leu Asp Ala Phe Leu Arg Lys
705                 710                 715                 720
His Asp Gly Gln Phe Thr Val Ile Gln Leu Val Gly Met Leu Arg Gly
                725                 730                 735
Ile Ala Ala Gly Met Arg Tyr Leu Ala Asp Met Gly Tyr Val His Arg
            740                 745                 750
Asp Leu Ala Ala Arg Asn Ile Leu Val Asn Ser Asn Leu Val Cys Lys
        755                 760                 765
Val Ser Asp Phe Gly Leu Ser Arg Val Ile Glu Asp Asp Pro Glu Ala
    770                 775                 780
Val Tyr Thr Thr Thr Gly Gly Lys Ile Pro Val Arg Trp Thr Ala Pro
785                 790                 795                 800
Glu Ala Ile Gln Tyr Arg Lys Phe Thr Ser Ala Ser Asp Val Trp Ser
                805                 810                 815
Tyr Gly Ile Val Met Trp Glu Val Met Ser Tyr Gly Glu Arg Pro Tyr
            820                 825                 830
Trp Asp Met Ser Asn Gln Asp Val Ile Lys Ala Ile Glu Glu Gly Tyr
        835                 840                 845
Arg Leu Pro Ala Pro Met Asp Cys Pro Ala Gly Leu His Gln Leu Met
    850                 855                 860
```

```
Leu Asp Cys Trp Gln Lys Asp Arg Ala Glu Arg Pro Lys Phe Glu Gln
865                 870                 875                 880

Ile Val Gly Ile Leu Asp Lys Met Ile Arg Asn Pro Ser Ser Leu Lys
                885                 890                 895

Thr Pro Leu Gly Thr Cys Ser Arg Pro Leu Ser Pro Leu Leu Asp Gln
            900                 905                 910

Ser Thr Pro Asp Phe Thr Ala Phe Cys Ser Val Gly Glu Trp Leu Gln
        915                 920                 925

Ala Ile Lys Met Glu Arg Tyr Lys Asp Asn Phe Thr Ala Ala Gly Tyr
    930                 935                 940

Asn Ser Leu Glu Ser Val Ala Arg Met Thr Ile Asp Asp Val Met Ser
945                 950                 955                 960

Leu Gly Ile Thr Leu Val Gly His Gln Lys Lys Ile Met Ser Ser Ile
                965                 970                 975

Gln Thr Met Arg Ala Gln Met Leu His Leu His Gly Thr Gly Ile Gln
            980                 985                 990

Val
```

(2) INFORMATION FOR SEQ ID NO: 12:

(i) SEQUENCE CHARACTERISTICS:
        (A) LENGTH:       994 amino acids
        (B) TYPE:         amino acid
        (C) STRANDEDNESS:  single
        (D) TOPOLOGY:     linear (ii) MOLECULE TYPE:      peptide (xi) SEQUENCE DESCRIPTION: SEQ ID NO: 12:

```
Met Val Val Gln Thr Arg Phe Pro Ser Trp Ile Ile Leu Cys Tyr Ile
1               5                   10                  15

Trp Leu Leu Gly Phe Ala His Thr Gly Glu Ala Gln Ala Ala Lys Glu
            20                  25                  30

Val Leu Leu Leu Asp Ser Lys Ala Gln Gln Thr Glu Leu Glu Trp Ile
        35                  40                  45

Ser Ser Pro Pro Ser Gly Trp Glu Glu Ile Ser Gly Leu Asp Glu Asn
50                  55                  60

Tyr Thr Pro Ile Arg Thr Tyr Gln Val Cys Gln Val Met Glu Pro Asn
65                  70                  75                  80

Gln Asn Asn Trp Leu Arg Thr Asn Trp Ile Ser Lys Gly Asn Ala Gln
                85                  90                  95

Arg Ile Phe Val Glu Leu Lys Phe Thr Leu Arg Asp Cys Asn Ser Leu
            100                 105                 110

Pro Gly Val Leu Gly Thr Cys Lys Glu Thr Phe Asn Leu Tyr Tyr Tyr
        115                 120                 125

Glu Thr Asp Tyr Asp Thr Gly Arg Asn Ile Arg Glu Asn Leu Tyr Val
    130                 135                 140

Lys Ile Asp Thr Ile Ala Ala Asp Glu Ser Phe Thr Gln Gly Asp Leu
145                 150                 155                 160

Gly Glu Arg Lys Met Lys Leu Asn Thr Glu Val Arg Glu Ile Gly Pro
                165                 170                 175

Leu Ser Lys Lys Gly Phe Tyr Leu Ala Phe Gln Asp Val Gly Ala Cys
            180                 185                 190

Ile Ala Leu Val Ser Val Lys Val Tyr Tyr Lys Lys Cys Trp Thr Ile
        195                 200                 205

Val Glu Asn Leu Ala Val Phe Pro Asp Thr Val Thr Gly Ser Glu Phe
```

```
                    210                 215                 220
Ser Ser Leu Val Glu Val Arg Gly Thr Cys Val Ser Ala Glu Glu
225                 230                 235                 240

Glu Ala Glu Asn Ser Pro Arg Met His Cys Ser Ala Glu Gly Glu Trp
                    245                 250                 255

Leu Val Pro Ile Gly Lys Cys Ile Cys Lys Ala Gly Tyr Gln Gln Lys
                    260                 265                 270

Gly Asp Thr Cys Glu Pro Cys Gly Arg Arg Phe Tyr Lys Ser Ser Ser
                    275                 280                 285

Gln Asp Leu Gln Cys Ser Arg Cys Pro Thr His Ser Phe Ser Asp Arg
    290                 295                 300

Glu Gly Ser Ser Arg Cys Glu Cys Glu Asp Gly Tyr Tyr Arg Ala Pro
305                 310                 315                 320

Ser Asp Pro Pro Tyr Val Ala Cys Thr Arg Pro Pro Ser Ala Pro Gln
                    325                 330                 335

Asn Leu Ile Phe Asn Ile Asn Gln Thr Thr Val Ser Leu Glu Trp Ser
                    340                 345                 350

Pro Pro Ala Asp Asn Gly Gly Arg Asn Asp Val Thr Tyr Arg Ile Leu
                    355                 360                 365

Cys Lys Arg Cys Ser Trp Glu Gln Gly Glu Cys Val Pro Cys Gly Ser
    370                 375                 380

Asn Ile Gly Tyr Met Pro Gln Gln Thr Gly Leu Glu Asp Asn Tyr Val
385                 390                 395                 400

Thr Val Met Asp Leu Leu Ala His Ala Asn Tyr Thr Phe Glu Val Glu
                    405                 410                 415

Ala Val Asn Gly Val Ser Asp Leu Ser Arg Ser Gln Arg Leu Phe Ala
                    420                 425                 430

Ala Val Ser Ile Thr Thr Gly Gln Ala Ala Pro Ser Gln Val Ser Gly
                    435                 440                 445

Val Met Lys Glu Arg Val Leu Gln Arg Ser Val Gln Leu Ser Trp Gln
    450                 455                 460

Glu Pro Glu His Pro Asn Gly Val Ile Thr Glu Tyr Glu Ile Lys Tyr
465                 470                 475                 480

Tyr Glu Lys Asp Gln Arg Glu Arg Thr Tyr Ser Thr Leu Lys Thr Lys
                    485                 490                 495

Ser Thr Ser Ala Ser Ile Asn Asn Leu Lys Pro Gly Thr Val Tyr Val
                    500                 505                 510

Phe Gln Ile Arg Ala Val Thr Ala Ala Gly Tyr Gly Asn Tyr Ser Pro
                    515                 520                 525

Arg Leu Asp Val Ala Thr Leu Glu Glu Ala Ser Gly Lys Met Phe Glu
    530                 535                 540

Ala Thr Ala Val Ser Ser Glu Gln Asn Pro Val Ile Ile Ala Val
545                 550                 555                 560

Val Ala Val Ala Gly Thr Ile Ile Leu Val Phe Met Val Phe Gly Phe
                    565                 570                 575

Ile Ile Gly Arg Arg His Cys Gly Tyr Ser Lys Ala Asp Gln Glu Gly
                    580                 585                 590

Asp Glu Glu Leu Tyr Phe His Cys Thr Lys Thr Tyr Ile Asp Pro Glu
                    595                 600                 605

Thr Tyr Glu Asp Pro Asn Arg Ala Val His Gln Phe Ala Lys Glu Leu
    610                 615                 620

Asp Ala Ser Cys Ile Lys Ile Glu Arg Val Ile Gly Ala Gly Glu Phe
625                 630                 635                 640
```

-continued

```
Gly Glu Val Cys Ser Gly Arg Leu Lys Leu Pro Gly Gln Arg Asp Val
                645                 650                 655

Ala Val Ala Ile Lys Thr Leu Lys Val Gly Tyr Thr Glu Lys Gln Arg
            660                 665                 670

Arg Asp Phe Leu Cys Glu Ala Ser Ile Met Gly Gln Phe Asp His Pro
        675                 680                 685

Asn Val Val His Leu Glu Gly Val Val Thr Arg Gly Lys Pro Val Met
    690                 695                 700

Ile Val Ile Glu Phe Met Glu Asn Gly Ala Leu Asp Ala Phe Leu Arg
705                 710                 715                 720

Lys His Asp Gly Gln Phe Thr Val Ile Gln Leu Val Gly Met Leu Arg
                725                 730                 735

Gly Ile Ala Ala Gly Met Arg Tyr Leu Ala Asp Met Gly Tyr Val His
                740                 745                 750

Arg Asp Leu Ala Ala Arg Asn Ile Leu Val Asn Ser Asn Leu Val Cys
            755                 760                 765

Lys Val Ser Asp Phe Gly Leu Ser Arg Val Ile Glu Asp Asp Pro Glu
        770                 775                 780

Ala Val Tyr Thr Thr Thr Gly Gly Lys Ile Pro Val Arg Trp Thr Ala
785                 790                 795                 800

Pro Glu Ala Ile Gln Tyr Arg Lys Phe Thr Ser Ala Ser Asp Val Trp
                805                 810                 815

Ser Tyr Gly Ile Val Met Trp Glu Val Met Ser Tyr Gly Glu Arg Pro
                820                 825                 830

Tyr Trp Asp Met Ser Asn Gln Asp Val Ile Lys Ala Ile Glu Glu Gly
            835                 840                 845

Tyr Arg Leu Pro Ala Pro Met Asp Cys Pro Ala Gly Leu His Gln Leu
    850                 855                 860

Met Leu Asp Cys Trp Gln Lys Asp Arg Ala Glu Arg Pro Lys Phe Glu
865                 870                 875                 880

Gln Ile Val Gly Ile Leu Asp Lys Met Ile Arg Asn Pro Ser Ser Leu
                885                 890                 895

Lys Thr Pro Leu Gly Thr Cys Ser Arg Pro Leu Ser Pro Leu Leu Asp
            900                 905                 910

Gln Ser Thr Pro Asp Phe Thr Ala Phe Cys Ser Val Gly Glu Trp Leu
    915                 920                 925

Gln Ala Ile Lys Met Glu Arg Tyr Lys Asp Asn Phe Thr Ala Ala Gly
    930                 935                 940

Tyr Asn Ser Leu Glu Ser Val Ala Arg Met Thr Ile Asp Asp Val Met
945                 950                 955                 960

Ser Leu Gly Ile Thr Leu Val Gly His Gln Lys Lys Ile Met Ser Ser
                965                 970                 975

Ile Gln Thr Met Arg Ala Gln Met Leu His Leu His Gly Thr Gly Ile
                980                 985                 990

Gln Val
```